US008362328B2

(12) United States Patent
Tanksley et al.

(10) Patent No.: US 8,362,328 B2
(45) Date of Patent: Jan. 29, 2013

(54) POLYNUCLEOTIDES ENCODING PHENYLPROPANOID PATHWAY ENZYMES IN COFFEE

(75) Inventors: Steven D. Tanksley, Dryden, NY (US); Chenwel Lin, Aubumdale, MA (US); Maud Lepelley, Tours (FR); James Gérard McCarthy, Noizay (FR); Vincent Petiard, Tours (FR); Gerald Cheminade, Tours (FR)

(73) Assignee: Nestec, S.A., Vevey (CH)

( * ) Notice: Subject to any disclaimer, the term of this patent is extended or adjusted under 35 U.S.C. 154(b) by 1008 days.

(21) Appl. No.: 12/083,041

(22) PCT Filed: Oct. 10, 2006

(86) PCT No.: PCT/US2006/039618
§ 371 (c)(1),
(2), (4) Date: Feb. 27, 2009

(87) PCT Pub. No.: WO2007/044751
PCT Pub. Date: Apr. 19, 2007

(65) Prior Publication Data
US 2009/0158456 A1  Jun. 18, 2009

Related U.S. Application Data

(60) Provisional application No. 60/724,673, filed on Oct. 7, 2005.

(51) Int. Cl.
*C12N 15/29* (2006.01)
*C12N 15/52* (2006.01)
*C12N 15/82* (2006.01)
(52) U.S. Cl. ...................... 800/317.3; 800/306; 800/312; 800/320.1; 800/320.2; 800/320.3; 536/23.1; 536/23.6; 435/320.1
(58) Field of Classification Search .................. 800/298; 536/23.2, 23.6
See application file for complete search history.

(56) References Cited

U.S. PATENT DOCUMENTS 7,663,023 B2 * 2/2010 Dixon et al. .................. 800/285

FOREIGN PATENT DOCUMENTS

WO  WO 2004/001028 A1  12/2003
WO  WO 2004/035745 A2  4/2004

OTHER PUBLICATIONS

Theor. Appl. Genet (2003) vol. 107; pp. 751-756.*
Hoffman, L. et al. The Plant Cell (Jun. 2004); vol. 16; pp. 1446-1465.*
Hoffmann, L. et al, "Purification, Cloning, ad Properties of an Acyltransferase Controlling Shikimate and Quinate Ester Intermediates in Phenylpropanoid Metabolism," *Journal of Biological Chemistry*, vol. 278, No. 1, Jan. 3, 2003, pp. 95-103, XP009083239 ISSN: 0021-9258, cited in the application figures 1, 5.
Campa, C. et al., "Genetic Mapping of a Caffeoyl-Coenzyme A 3-0-Methyltransferase Gene in Coffee Trees. Impact on Chlorogenic Acid Content," *Theoretical and Applied Genetics*, vol. 107, No. 4, Aug. 2003, pp. 751-756, XP009083044, ISSN: 0040-5752, cited in the application, figure 1.
Hoffmann, L. et al., "Silencing of Hydroxcinnamoy-Coenzyme A Shikimate/Quinate Hydroxycinnamoy 1 Transferase Affects Phenylpropanoid Biosynthesis," *Plant Cell*, vol. 16, No. 6, Jun. 2004, pp. 1446-1465, XP009083263, ISSN: 1040-4651, cited in the application, figure 1.
Niggeweg, R. et al., "Engineering Plants with Increased Levels of the Antioxidant Chlorogenic Acid," *Nature Biotechnology*, vol. 22, No. 6, Jun. 2004, pp. 746-754, XP009087941, ISSN: 1087-0156, the whole document.
Schoch, G. et al., CYP09A3 from *Arabidopsis thaliana* is a 3'-Hydroxylase of Phenolic Esters, a Missing Link in the Phenylpropanoid Pathway,: *Journal of Biological Chemistry*, American Society of Biolochemical Biologists, Birmingham, US., vol. 276, No. 39, Sep. 28, 2001, pp. 36566-36574, XP002223727, ISSN: 0021-9258.
Busam, G. et al., "Isolation of Tobacco cDNA Encoding Caffeoyl-CoA 3-0-Methyltransferase (Accession Nos. Z56282 and Z82982)," *Plant Physiology*, (Rockville), vol. 113, No. 3, 1997, p. 1003, XP009087942, ISSN: 0032-0889, p. 1003, col. 2, paragraph 2.
Database EMBL [Online] Dec. 4, 1995, Busam et al.: "*N. tabacum* mRNA for Caffeoyl-CoA O-methyltransferase," XP002445875, retrieved from EBI accession No. EMBL: Z562852, Database accession No. Z56282 the whole document.
Database UniProt [Online] Nov. 1, 1996, Busam et al. "Caffeoyl-CoA O-Methyltransferase 6 (EC 2.1.1.104) (Trans-caffeoyl-CoA 3-O-methyltransferase 6) (CCoAMT-6) (CCoAOMT-6)," XP002445964, retrieved from EBI Database accession No. Q42945, the whole document.
Database UniProt [Online] Jul. 1, 1997, Busam et al., ,,Caffeoyl-CoA O-methyltransferase 5 (EC 2.1.1.104) (Trans-caffeoyl-CoA 3-O-methyltransferase 5 (CCoAMT-5) (CCoAOMT-5). G XP002445965, retrieved from EBI Database accession No. 004899/.
Lepelley, M. et al., "Chlorogenic Acid Synthesis in Coffee: An Analysis of CGA Content and Real-Time RT-PCR Expression of HCT, HQT, C3H1, and CCoAOMT1 Genes During Grain Development in *C. canephor*," *Plant Science* (Amsterdam, Netherlands), 172(5), 978-996 CODEN: PLSCE4; ISSN: 0168-9452, 2007, XP009083025, the whole document.
Altschul, S. F. et al., "Gapped BLAST and PSI-Blast: a New Generation of Protein Database Search," *Nucleic Acids Res.*, vol. 25, pp. 3389-3402, 1997.
Clifford, M. N., "Chlorogenic Acids, in *Coffee 1*," Chemistry, Ed by Clarke RJ and Macrae R. Elsevier Applied Science, London, pp. 153-202, 1985. Clifford, M. N., and Walker, R., "Chlorogenic Acids—Confounders of Coffee±Serum Cholesterol Relationships," *Food Chem.*, vol. 24: 77-80, 1987.

(Continued)

*Primary Examiner* — Russell Kallis
(74) *Attorney, Agent, or Firm* — Potter Anderson & Corroon, LLP

(57) ABSTRACT

Polynucleotides and polypeptides involved in the biosynthetic pathway of chlorogenic acids in the coffee plant are disclosed. Also disclosed are methods for using these polynucleotides and polypeptides for the manipulation of flavor, aroma, and other features of coffee beans, as well as for the protection of coffee plants against diseases or oxidative stress.

12 Claims, 54 Drawing Sheets

OTHER PUBLICATIONS

Clifford, M. N., "The Nature of Chlorogenic Acids—Are They Advantageous Compounds in Coffee?," in *Dix-Septième Colloque Scientifique International Sur Le Café*. ASIC, Paris, pp. 79-91, 1998.

Clifford, M. N., "Chlorogenic Acids and Other Cinnamates—Nature, Occurrence and Dietary Burden," *J Sci Food Agric.*, vol. 79: 362-372, 1999.

Clifford, M. N., "Chlorogenic Acids and Other Cinnamates—Nature, Occurrence, Dietary Burden, Absorption and Metabolism," *J Sci Food Agric.*, vol. 80: 1033-1043, 2000.

Crouzillat, D. et al., 1996, "*Theobroma cacao* L.: A Genetic Linkage Map and Quantitative Trait Loci Analysis," *Theor Appl Genet.*, vol. 93, pp, 205-214.

Ferrer, J. L. et al. "Crystal Structures of Alfalfa Caffeoyl Coenzyme a 3-O-Methyltransferase," *Plant Physiol.*, vol. 137: 1009-1017, 2005.

Gang, D., et al., "An Investigation of the Storage and Biosynthesis of Phenylpropenes in Sweet Basil," *Plant physiol.*, vol. 125: 539-555, 2001.

Grace, S.C. and Logan, B.A., "Energy Dissipation and Radical Scavenging by the Plant Phenylpropanoid Pathway," *Phil. Trans. R. Soc. Lond. B.* 355:1499-1510, 2000.

Hoffmann L., et al., "Purification, Cloning, and Properties of an Acyltransferase Controlling Shikimate and Quinate Ester Intermediates in Phenylpropanoid Metabolism," *J. Bio. Chem.*, vol. 278(1): 95-103, 2003.

Hoffmann, L., "Silencing of Hydroxycinnamoyl-Coenzyme a Shikimate/Quinate Hydroxycinnamoyltransferase Affects Phenylpropanoid Biosynthesis," *Plant Cell*, vol. 16: 1446-1465, 2004.

Hollman, P. C. H., "Evidence for Health Benefits of Plant Phenols: Local or Systemic Effects?" *J. Sci. Food Agric.*, vol. 81:842-852, 2001.

Inoue K. et al., "Developmental Expression and Substrate Specificities of Alfalfa Caffeic Acid 3-O-Methyltransferase and Caffeoyl Coenzyme A 3-O-Methyltransferase in Relation to Lignification," *Plant Physiol.*, vol. 117: 761-770, 1998.

Ky, C.-L., "Caffeine, Trigonelline, Chlorogenic Acids and Sucrose Diversityin Wild *Coffea arabica* L. and *C. canephora* P. Accessions ,"*Food Chemistry*, vol. 75: 223-230, 2001.

Lee, C. Y., and Jaworski, A. "Phenolic Compounds in White Grapes Grown in New York," *Am. Enol. & Viticul.*, vol. 38: 277-281, 1987.

Leloup, V. et al., "Degradation Mechanisms of Chlorogenic Acids During Roasting," *Compte-rendus du Seizieme Colloque de l'ASIC (Association Scientifique Internationale sur le Café), ASIC Kyoto*, pp. 192-198; 1995.

Maher, E. A. et al. "Increased Disease Susceptibility of Transgenic Tobacco Plants With Suppressed Levels of Preformed Phenylpropanoid Products," *Proc. Natl. Acad. Sci. USA*, vol. 91:7802-7806, 1994.

Marraccini, P. et al., "Molecular Cloning of the Complete 11S Seed Storage Protein Gene of *Coffea arabica* and Promoter Analysis in the Transgenic Tobacco Plants," *Plant Physiol. Biochem.*, vol. 37, pp. 273-282, 1999.

Maury, S. et al., "Tobacco O-Methyltransferases Involved in Phenylpropanoid Metabolism. the Different Caffeoyl-Coenzyme A/5-Hydroxyferuloyl-Coenzyme A 3/5-O-Methyltransferase and Caffeic Acid/5-Hydroxyferulic Acid 3/5-O-Methyltransferase Classes Have Distinct Substrate Specificities and Expression Patterns," *Plant Physiol..* vol. 121: 215-224, 1999.

Mitchell, H.J., et al., "Differential Induction of Cinnamyl Alcohol Dehydrogenase During Defensive Lignification in Wheat (*Triticum aestivum* L.): Characterisation of the Major Inducible Form," *Planta*, vol. 208 : 31-37, 1999.

Montavon, P., et al.,"Evolution of Green Coffee Protein Profiles With Maturation and Relationship to Coffee Cup Quality," *J. Agric. Food Chem.*, vol. 51: 2328-2334, 2003.

Montavon, P., et al., "Changes in Green Coffee Protein Profiles during Roasting," *Food Chem.*, vol. 51: 2335-2343, 2003.

Nair, R., et al., "*Arabidopsis* CYP98A3 Mediating Aromatic 3-Hydroxylation Developmental Regulation of the Gene, and Expression in Yeast ," *Plant Physiol.*, vol. 130: 210-220, 2002.

Natella, F., et al., "Coffee Drinking Influences Plasma Antioxidant Capacity in Humans," *J. Agric. Food Chem.*, vol. 50: 6211-6216, 2002.

Niggeweg, R. et al., "Engineering Plants With Increased Levels of the Antioxidant Chlorogenic Acid," *Nature Biotech.*, vol. 22(6): 746-54, 2004.

Ohnishi, M., et al.,"Inhibitory Effects of Chlorogenic Acids on Linoleic Acid Peroxidation and Haemolysis," *Phytochemistry*, vol. 36 :579-583, 1994.

Olthof, M..R. et al., "Chlorogenic Acid and Caffeic Acid are Absorbed in Humans," *J. Nutr.*, vol. 131 :66-71, 2001.

Parvathi, K. et al., "Substrate Preferences of O-Methyltransferases in Alfalfa Suggest New Pathways for 3-O-Methylation of Monolignols," *Plant Journal*, vol. 25: 193-202, 2001.

Rice-Evans, C. A. et al., "Structure-Antioxidant Activity Relationships of Flavonoids and Phenolic Acids," *Free Rad. Biol. Med.*, vol. 20:933-956, 1996.

Rogers, J., et al., "Changes to the Content of Sugars, Sugar Alcohols, Myo-Inositol, Carboxylic Acids and Inorganic Anions in Developing Grains From Different Varieties of *Robusta* (*Coffea canephora*) and *Arabica* (*C. arabica*) Coffees," *Plant Science,.* vol. 149: 115-123, 1999.

Schoch, G., et al., "CYP98A3 From *Arabidopsis thaliana* is a 3-Hydroxylase of Phenolic Esters, A Missing Link in the Phenylpropanoid Pathway," *J. Bio. Chem.*, vol. 266(39): 36566-36574, 2001.

Shadle, G., et al. "Phenylpropanoid Compounds and Disease Resistance in Transgenic Tobacco With Altered Expression of L-Phenylalanine Ammonia-Lyase," *Phytochemistry*, vol. 64: 153-161, 2003.

Shibata, H., et al. "Natural Antioxidant, Chlorogenic Acid, Protects Against DNA Breakage Caused by Monochloramine," *Biosci. Biotechnol. Biochem.*, vol. 63:1295-1297, 1999.

Tamagnone, T, et al. "Inhibition of Phenolic Acid Metabolism Results in Precocious Cell Death and Altered Cell Morphology in Leaves of Transgenic Tobacco Plants," *Plant Cell*, vol. 10: 1801-1816, 1998.

Voilley, A., et al. Influence Sur L'amertume D'un Café Boisson De Quelques Paramètres D'extraction. *Compte-Rendus Du Huitième Colloque De L'asic (Association Scientifique International Sur Le Café)*, ASIC pp. 192-198251-259, 1977.

Zhong, R., III et al., "Dual Methylation Pathways in lignin Biosynthesis," *Plant Cell*, vol. 10(12), pp. 2033-2046, 1998.

\* cited by examiner (Page 1 of 5)

FIG. 2b
(Page 2 of 5)

FIG. 2b
(Page 3 of 5)

FIG. 2b
(Page 4 of 5)

```
                                          142
                                          209
                                          138 pccsvc22w14m23    T G T C A T T T G A G T T T C T A A A A A A A A A A A A A A A A A A A A A
Race1_CdhCT
pMl1 pccsvc22w14m23    A A A A A A A A A A A A A A A A A A A A A A A A A A A A A A    146
Race1_CdhCT                                                                      209
pMl1                                                                             138
```

FIG. 2b
(Page 5 of 5)

FIG. 3b
(Page 1 of 6)

(Page 2 of 6)

(Page 3 of 6)

(Page 4 of 6)

(Page 5 of 6)

FIG. 3b
(Page 6 of 6)

(Page 1 of 4)

(Page 2 of 4)

(Page 3 of 4)

(Page 4 of 4)

(Page 1 of 5)

(Page 2 of 5)

(Page 3 of 5)

(Page 4 of 5)

FIG. 5b
(Page 5 of 5)

(Page 1 of 4)

(Page 2 of 4)

(Page 3 of 4)

FIG. 6b
(Page 4 of 4)

FIG. 7
(Page 1 of 3)

FIG. 7
(Page 2 of 3)

(Page 3 of 3)

(Page 1 of 4)

(Page 2 of 4)

(Page 3 of 4)

FIG. 9b
(Page 4 of 4)

(Page 1 of 4)

FIG. 10b
(Page 2 of 4)

FIG. 10b
(Page 3 of 4)

FIG. 10b
(Page 4 of 4)

SEQUENCE LISTING

```
<160> NUMBER OF SEQ ID NOS: 90

<210> SEQ ID NO 1
<211> LENGTH: 1388
<212> TYPE: DNA
<213> ORGANISM: Coffea canephora

<400> SEQUENCE: 1
ccatgaaaat cgaggtgaag gaatcgacta tggtgagacc tgcccaagaa actcctggga      60
ggaacttgtg gaactcgaac gtggacttgg tggtgccaaa tttccacacc cctagcgtct     120
acttctatag gccgacggga tcatcgaatt tctttgatgc caaagtgcta aaggacgctt     180
tgagccgagc ccttgtcccg ttctacccaa tggctggtag gttaaagaga gacgaagatg     240
ggcggattga gattgagtgc aatggtgaag gcgtgctttt cgtggaggcc gagtctgatg     300
gagtagttga tgatttcggt gactttgcac caactttaga gcttcgtaga ctcattcctg     360
cagttgatta ttctcaagga atatcaagct acgctctcct agtgctgcag gtgacatatt     420
tcaagtgtgg tggagtctct cttggtgttg gcatgcgaca tcatgcagct gatggatttt     480
caggtcttca tttcatcaat tcatggtctg atatggcccg tggccttgat gtgaccctgc     540
caccattcat agaccgcacc ctcctccgtg cccgcgatcc gccccagcct caattccagc     600
acattgagta ccaacctcct ccagccttaa aagtttcccc gcaaactgca aaatctgact     660
```

```
cagttcctga aactgcggtg tccatcttca agttaaccag ggagcaaatc agtgccctga    720
aagccaagtc caaggaagat ggaaacacca ttagctatag ctcctacgaa atgttggcag    780
gccatgtatg gcgctgtgct tgcaaggcac gaggactcga agttgatcaa ggaacaaaat    840
tgtacattgc tactgatgga cgggcaagac ttaggccttc gctcccacct ggctattttg    900
gcaatgtcat cttcacggca accccgatag ctatagctgg tgaccttgaa ttcaagccag    960
tctggtatgc tgccagtaaa atccacgatg cattggcgag gatggacaac gactacttaa    1020
ggtcagctct tgattacttg gaattacagc ctgatttgaa ggcccggtt cgtggtgccc    1080 atactttcaa gtgtccaaat ctggggatca caagctgggt aaggttaccc atccatgatg    1140
ctgattttgg ctggggtcgg cccatatttta tgggtcctgg tggcatcgct tatgaaggtt    1200
taagctttat attgcctagt ccaaccaatg atggaagcat gtcagtagct atttcattgc    1260
agggcgagca catgaaactc ttccagagtt tcttgtatga catttgaacg ggagcacatc    1320
acatgaattt tcacgcttgt attaatagct ttcggttccg ggccagctat tcatgcggtg    1380
gtggtttc                                                            1388

<210> SEQ ID NO 2
<211> LENGTH: 1388
<212> TYPE: DNA
<213> ORGANISM: Coffea arabica

<400> SEQUENCE: 2
ccatgaaaat cgaggtgaag gaatcgacta tggtgagacc tgcccacgaa actcctagga     60
ggaacttgtg gaactcgaac gtggacttgg tggtgccaaa tttccacacc cctagcgtct    120
acttctatag gccgacggga tcatcgaatt tctttgatgc caaagtgctg aaggacgctt    180
tgagccgagc ccttgtcccg ttctacccaa tggctggtag gttaaagaga gacgaagatg    240
ggcggattga gattgagtgc aatggtgaag gcgtgctttt cgtggaggcc gagtctgatg    300
gagtagttga tgatttcggt gactttgcac caactttaga gcttcgtaga ctcattcctg    360
cagttgatta ttctcaagga atatcaagct acgctctcct agtgctgcag gtgacatatt    420
tcaagtgtgg tggagtctct cttggtgttg gcatgcaaca tcatgcagct gatggatttt    480
caggtcttca tttcatcaat tcatggtctg atatggcccg tggccttgat gtgaccctgc    540
caccattcat agaccgcacc ctcctccgtg cccgcgatcc gccccagccc caattccagc    600
acattgagta ccaaccccct ccaaccttaa aagtttcccc gcaaactgca aaatctgact    660
cagttcctga aactgcagtg tccatcttca agttaaccag ggagcaaatc agtgccctga    720
aagccaagtc caaggaagat ggaaacacca ttagctatag ctcctacgaa atgttggcag    780
gccatgtatg gcgctgtgct tgcaaggcac gaggactcga agttgatcaa ggaacaaaat    840
tgtacattgc tactgatgga cgagcaagac ttaggccttc gctcccgcct ggctattttg    900
gcaatgtcat cttcacggca accctgatag ctatagctgg tgaccttgaa ttcaagccag    960
tctggtatgc tgcaagtaaa atccacgatg cattggcgag gatggacaac gactacttaa    1020
ggtcagctct tgattacttg gaattacagc ctgatttgaa ggcccggtt cgtggtgccc    1080 atactttcaa gtgtccaaat ctggggatca caagctgggt aaggttaccc atccatgatg    1140
ctgattttgg ctggggtcgg cccatatttta tgggtcctgg tggtatcgct tatgaaggtt    1200
taagctttat attgcctagt ccaaccaatg atggaagcat gtcagtagct atttcattgc    1260
agggcgagca catgaaactc ttccagagtt tcctgtatga catttgaatg ggagcacatc    1320
acatgaattt tcacgcttgt attaatagct ttcggttccg ggccagctat tcatgcggtg    1380
```

```
<210> SEQ ID NO 3
<211> LENGTH: 1534
<212> TYPE: DNA
<213> ORGANISM: Coffea canephora

<400> SEQUENCE: 3
cttctccatc ccagctcgtt tctgacaaat ccctttcgtc aatcaacaaa actctttaca      60
tattttctgc taaatctcag cttatttcat cttgtttgat cagcgtggga agcgagaaaa     120
tgaagataac cgtgaaggaa acagcaatgg ttcgtccagc ccaaccaaca cccacaaaga     180
ggctatggaa ctcgaatttg gatcttctgg tagcaagaat tcatatcttg accgtctact     240
tctacaagcc taatggttct gctaatttct ttgatacccg tgtgctcaaa gaagcattga     300
gcaatgttct tgtctctttc taccccatgg ctgggagatt agcaagagat gaagaaggaa     360
ggattgagat cgactgtaac ggtgaaggtg tactctttgt tgaggctgaa tcagactcga     420
gtgtcgatga ttttggtgat tttgcaccaa gtttggagct caggaggctc atcccgaccg     480
tcgattgttc tggtgacatt tcttcttacc ccctcgttat tttccaggta actcgtttca     540
agtgtggagc agcagctctt ggagctgggg tgcagcacaa tttatcagat ggcgtttcat     600
ctctgcactt catcaataca tggtcagaca tagctcgtgg cctcaccatt gctgtccctc     660
cgttcattga ccggacactt atccgtgcta gggaccctcc cgtgcctgta ttcgaacatg     720
tcgaatatta ccgccccct caactaaaat cagattcaag aattcaagaa ctcaaaacag     780
gccctagggc aagtaccaca gctgtactaa aaatcacacc tgaacaactt agccagctta     840
aagctaaggc caacaatgag ggcagcactt atgagatctt agcagcacat atatggcgta     900
ctgcatgcaa agcacgtggc ctcaccaatg atcaatccac caagctgtac gttgccactg     960
atggccggtc taggctgatt cctccccctgc ctcctggcta tctaggtaat gtggtcttca    1020
ctgcaactcc aattgctgaa tccagtaatc ttcaatcaga gcccttgacc aattctgcaa    1080
aaagaatcca caacgccttg caagaatgg ataatgatta cttaagatca gccctggatt    1140
atcttgaaat tcaacctgat ttgtctgctt tggttagagg gcctcggcat tttgctagtc    1200
ctaatttgaa tatcaatagt tggacaaggc ttccgtttca tgatgcagac tttggctggg    1260
gcagacctat tcatataggg ccggcaatca ttctttatga gggtacggta tatgtattgc    1320
caagtccagg caaagacagg actttatcgt tagctgtgtg cttagatgcc gatcacatgc    1380
cactcttcca aaggttcctg tacgatttct gagaaatttt gaaatatcaa caacaatcaa    1440
taatcaagct tctggaagag aatggatgga attaccattt ttagatggta caaatcaagg    1500
cagcctcgtg acacttgtga ttggattggg actc                                1534

<210> SEQ ID NO 4
<211> LENGTH: 1533
<212> TYPE: DNA
<213> ORGANISM: Coffea arabica
<220> FEATURE:
<221> NAME/KEY: misc_feature
<222> LOCATION: (932)..(932)
<223> OTHER INFORMATION: n is a, c, g, or t

<400> SEQUENCE: 4
cttctccatc ccagccgttt ctgacaaatc cctttcgtca atcaacaaaa ctctttacat      60
attttctgct aaatctcagc ttatttcatc ttgtttgatc agcgtgggaa gcgagaaaat     120
gaagataacc gtgaaggaaa cagcaatggt tcgtccagcc caaccaacac ccacaaagag     180
```

```
gctatggaac tcgaatttgg atcttctggt agcaagaatt catatcttga ccatctactt      240
ttacaagcct aatggttctg ctaatttctt tgatacccgt gtgctcaaag aagcattgag      300
caatgttctt gtctctttct accccatggc tgggagatta gcaagagatg aagaaggaag      360
gattgagatc gactgtaacg gtgaaggtgt actctttgtt gaggctgaat cagactcgag      420
tgtcgatgat tttggtgatt ttgcaccaag tttggagctc aggaggctca tcccgaccgt      480
cgattgttct ggtgacattt cttcttaccc cctcgttatt ttccaggtaa ctcgtttcaa      540
gtgtggagca gcagctcttg gagctggggt gcagcacaat ttatcagatg gcgtttcatc      600
tctgcacttc atcaatacat ggtcagacat agctcgtggc ctcaccattg ctgtccctcc      660
gttcattgac cggacactta tccatgctag ggaccctccc gtgcctgtat tcgaacatgt      720
cgaatattat ccgcccctc aactaaaatc agattcaaga attcaagaac tcaaaacagg       780
ccccagggca gtaccacag ctgtactaaa atcactcct gaacaactta gccagcttaa        840
agctaaggcc aacaatgagg gcagcactta tgagatctta gcagcacata tatggcgtac      900
cgcatgcaaa gcacgtggcc ccaccaatga tnaatccacc aagctgtacg ttgccaccga      960
tggccggtct aggctgattc ctcccctgcc tcctggctat ctaggtaatg tggtcttcac     1020
tgcaactcca attgctgaat ccagtgatct tcaatcagag cccttgacca attctgcaaa    1080
aagaatccac aatgccttgg caagaatgga taatgattac ttaagatcag ccctggatta    1140
tcttgaaatt caacctgatt tgtctgcttt ggttagaggg cctcggcatt tgctagtcc     1200 taacttgaat atcaatagtt ggacagggct tccgtttcat gatgcagact ttggctgggg    1260
cagacctatt catatagggc cggcaatcat tctttatgag ggtacggtat atgtattgcc    1320
aggtccaggc aaagacagga ctttatcgtt agctgtgtgc ttagatgccg atcacatgcc    1380
actcttccaa aagttcctgt acgatttctg agaaattttg aaatatcaac aacaatcaat    1440
aatcaagctt ctggaagaga atggatagaa ttaccatttt tagacggtac aaatcaaggc    1500
agcctcgtga cacttgtgat tggattggga ctc                                  1533

<210> SEQ ID NO 5
<211> LENGTH: 1728
<212> TYPE: DNA
<213> ORGANISM: Coffea canephora

<400> SEQUENCE: 5
caaatctcaa accttcgtat taaccaatgg ctctgcttct gatcctcctc ccagttgcct       60
tcatcttcct agcctacagc ctctatgaac gccttagatt caaactgcca cccgggccac      120
ggccaaaacc ggtggtcgga acatttacg acataaaacc ggtgaggttc aagtgctatg       180
cggagtggtc aaaactctat ggtccaatat tttctgtcta cttcggttcc cagctgaata     240
ctgttgtgaa cactgcagaa ctggccaaag aagttcttaa agacaatgat cagcaattgg     300
cagataggta caggagtaga ccctctgcca gaatgagcag aaatggccaa gatttgatat     360
gggctgatta tggtcctcat tatgtgaagg tcagaaaact gtgcaatctt gaactcttca     420
ctccaaaaag actggaaggc cttagacctt aagagagga tgaagttaca gccatggttg      480
attccatctt caaggactgc accaaacctg aaacaaagg caagagtctg ttgatgcgca      540
actacttggg atcagtagca ttcaacaaca ttacaaggct aacatttggg aagaggttca     600
tgaattcaga gggtgtggtt gatgaacaag gccagagagtt taagggcatt gtatcaaatg    660
ggataaggat tggtgcaaaa ctctccgtgg cagatcacat tccttggctt cgttggatgt     720
ttgtaggcga aaatgaggac ctggataagc acaatgcgcg gagagacaaa ctgaccagaa     780
```

```
tgatcatgga agagcacact cttgcaaggc aaaagagtgg caatactaag cagcattttg      840
ttgatgcatt gctcactctt caaaagcaat atgaattgag cgatgacact gtcattggac      900
tcctttggga catgattact gctggcatgg atacaaccac aatctcagta gaatgggcaa      960
tggcagagct ggtgaagaat ccaagggtgc agcaaaaggc gcaagaggaa cttgaccgag     1020
tcattggctc cgatagaatc atgactgaag ctgattttgc aaagctccca tacttacagt     1080
gtgtagctaa ggaagctcta aggctgcacc ctccaactcc actaatgctt cctcatagag     1140
ccaatgccaa tgtgaagatc ggtggttatg acatccctaa agggtctatc gtgcacgtta     1200
acgtctgggc gattgctcgt gatcctgcag cctggaaaaa tccactggaa ttccgacctg     1260
agagattcct ggaggaagat gttgacatca agggccacga ttatcggctc ctgccttttg     1320
gtgctggaag gaggatctgc cctggtgcac aacttgcact caatctggtc acttctatgc     1380
tggggcattt gttgcaccac tttacttggt ctccaccacc tggggtcagg cctgaagaga     1440
ttgacctgga agagagccct ggaacagtta cttatatgag aacccctttg caagctgttg     1500
caacaccaag attgcctgca catttgtaca atcgtgtgcc agtagagctg taatgcttcc     1560
tttctcttgt tactaaattt tcagcttgca agagttgctt cacttccaac tctccatttg     1620
attgtgaaga acttgttgga ttctccgagg tatttgagaa aagctactat ttttctagga     1680 aaataaaat aagggttttc taaaaaaaaa aaaaaaaaa aaaaaaaa                    1728

<210> SEQ ID NO 6
<211> LENGTH: 1144
<212> TYPE: DNA
<213> ORGANISM: Coffea canephora

<400> SEQUENCE: 6
gtctgtccaa agctccctca aactaaaaga gaaagaaaga aaaaaaaagc cccagaaatc       60
taatctccaa acaacaatta tggcccagaa tggagaagga aaggatagcc aaaatctcag      120
gcatcaagaa gtaggccaca aaagccttct gcaaagtgat gcactctacc agtacatcct      180
ggaaaccagc gtgtatccaa gagagccaga gcccatgaaa gagctgagag aactgacagc      240
aaagcatcca tggaatatta tgactacatc tgctgatgaa gggcagttct tgaacatgat      300
tatcaagttg atcaatgcca agaaaaccat ggagattgga gtttacactg gttactcgct      360
tctggctaca gctctcgctc ttccagaaga tgggaagata ttggccatgg atattaacag      420
agaaaactac gaattgggtc tgcccgtgat cgaaagggct ggtgtgtccc ataaaattga      480
cttcagagaa ggccctgctt tgccagtgct tgatgagttg attgaagatg acaagaacca      540
tggaagtttt gatttcatct tcgtggatgc tgacaaggac aactatctca actaccacaa      600
gaggataatc gagttggtca aggttggggg aatgattggg tacgacaaca ccctatggaa      660
cggctccgtg gtggcccac cagatgctcc aatgaggaag tacgtgaggt actacaggga      720
cttcgtcttg gagctcaaca aagccctggc cgctgatccc aggatcgaga tctgcatgct      780
ccccgttggc gacggtatca ccctgtgccg ccgcgtcagc taattaattt ccctactaaa      840
cccctgcgga aagttgggaa tcaaatgcaa atgaaaaata gcccaacacc tacttctttt      900
gcttcctcct cttttttgtt tttgggaccc tttgtatttt actactgcta tttgtttatt      960
ctgtgggaca cgctgttata tttgtaattt tctttgtact gagaataatt attactatat     1020
gaatctccct gtttacggca actagcaagg actagttgct tttaaaaaaa aaaaaaaaa     1080 aaaaaaaaa aaaaaaaaa aaaaaaaaa aaaaaaaaa aaaaaaaaa aaaaaaaaa           1140 aaaa                                                                  1144
```

<210> SEQ ID NO 7
<211> LENGTH: 713
<212> TYPE: DNA
<213> ORGANISM: Coffea arabica

<400> SEQUENCE: 7

| | | | | | |
|---|---|---|---|---|---|
| atggaaaaca | agggattgtt | gcagagtagg | gaactctatc | agtacctcct | ggagactagt | 60 |
| gtctatccac | atgaactgca | gcctctcaag | gagctaaggg | atgttactgc | aagtcatccg | 120 |
| tgggccacta | tggcaactgc | cccagatgct | ggtcagttga | ttgccatgct | cttgaaacta | 180 |
| ataagtgcca | aaaagacaat | agagattggt | gtctttactg | gatactccct | actgcttact | 240 |
| gcccttacaa | taccagatga | tggcaggatt | gtagcaattg | accagaacag | agatacatat | 300 |
| gagatagggc | tgccaattat | aagaaaagct | gcagttgagc | ataagatcga | cttcattgag | 360 |
| tccgaggctc | ttccagttct | tgataaactc | cttgaagaaa | atcttaacca | tgaagccttt | 420 |
| gactttgctt | tcgttgatgc | ggacaaatta | aattatctga | agtaccatga | aaactgttg | 480 |
| aaattgttaa | gcttggtgg | aatagttgta | tacgacaaca | cactttgggg | aggattggtg | 540 |
| gccttgccgg | aagaatctgt | ggctgaggaa | atgaaagcag | gcaggcattt | cacaattgag | 600 |
| ttcaacaaat | tgctagctgc | tgatacccga | gttcaaatat | cccaggttcc | tctgggtgat | 660 |
| gggattacta | tttgtaagcg | tctccactaa | atcttatgct | ggagtactta | ctt | 713 |

<210> SEQ ID NO 8
<211> LENGTH: 727
<212> TYPE: DNA
<213> ORGANISM: Coffea canephora

<400> SEQUENCE: 8

| | | | | | |
|---|---|---|---|---|---|
| atggccaagg | aaggaggttc | taaaatgaag | acaattctcc | agagtgaggc | cctccagaag | 60 |
| tacatcttga | atactagcac | atacccaaaa | gagcatgaac | aactgaagga | gctaagagaa | 120 |
| gagactgcca | ggaaatatgg | tgccagggct | attataggtg | tgccacctga | tgagggctc | 180 |
| ttcctgtcta | tgttttgaa | agtaatgaat | gccaagaaga | cactggagat | tggtgttttt | 240 |
| actggctatt | ctcttcttac | tactgctctt | gcacttcctg | atgatggcca | gatagttgca | 300 |
| atagaccctg | atcaaggagc | atttgaagtt | ggtctgaaat | tcatcaagaa | agctggtgtg | 360 |
| gagaacaaaa | tcaaattcat | caaatcagat | ggcatttctg | ctctaaatga | tttgttgaac | 420 |
| aatgaagcta | gtgaagcaac | attcgacttt | gcatttgtgg | atgcagacaa | gccaagctac | 480 |
| atccagtacc | atgaacaact | aataaagctg | gtgaagattg | aggaattat | cgcttacgat | 540 |
| aatactctat | acggtggata | tgttgtcagt | gaagaaattg | aaatgcacga | aggatccact | 600 |
| gtcaacagaa | aagccatcat | acaattcaac | aactatatag | cctcggatcc | gcgagttgag | 660 |
| atctctcagg | ttcctatagg | agatggtgtt | acattgtgta | ggcgcatcat | cgcttagctg | 720 |
| acatgat | | | | | | 727 |

<210> SEQ ID NO 9
<211> LENGTH: 434
<212> TYPE: PRT
<213> ORGANISM: Coffea canephora

<400> SEQUENCE: 9

Met Lys Ile Glu Val Lys Glu Ser Thr Met Val Arg Pro Ala Gln Glu
1               5                   10                  15

Thr Pro Gly Arg Asn Leu Trp Asn Ser Asn Val Asp Leu Val Val Pro
            20                  25                  30

```
Asn Phe His Thr Pro Ser Val Tyr Phe Tyr Arg Pro Thr Gly Ser Ser
             35                  40                  45

Asn Phe Phe Asp Ala Lys Val Leu Lys Asp Ala Leu Ser Arg Ala Leu
     50                  55                  60

Val Pro Phe Tyr Pro Met Ala Gly Arg Leu Lys Arg Asp Glu Asp Gly
 65                  70                  75                  80

Arg Ile Glu Ile Glu Cys Asn Gly Glu Gly Val Leu Phe Val Glu Ala
                 85                  90                  95

Glu Ser Asp Gly Val Val Asp Phe Gly Asp Phe Ala Pro Thr Leu
                100                 105                 110

Glu Leu Arg Arg Leu Ile Pro Ala Val Asp Tyr Ser Gln Gly Ile Ser
            115                 120                 125

Ser Tyr Ala Leu Leu Val Leu Gln Val Thr Tyr Phe Lys Cys Gly Gly
        130                 135                 140

Val Ser Leu Gly Val Gly Met Arg His His Ala Ala Asp Gly Phe Ser
145                 150                 155                 160

Gly Leu His Phe Ile Asn Ser Trp Ser Asp Met Ala Arg Gly Leu Asp
                165                 170                 175

Val Thr Leu Pro Pro Phe Ile Asp Arg Thr Leu Leu Arg Ala Arg Asp
            180                 185                 190

Pro Pro Gln Pro Gln Phe Gln His Ile Glu Tyr Gln Pro Pro Ala
        195                 200                 205

Leu Lys Val Ser Pro Gln Thr Ala Lys Ser Asp Ser Val Pro Glu Thr
        210                 215                 220

Ala Val Ser Ile Phe Lys Leu Thr Arg Glu Gln Ile Ser Ala Leu Lys
225                 230                 235                 240

Ala Lys Ser Lys Glu Asp Gly Asn Thr Ile Ser Tyr Ser Ser Tyr Glu
                245                 250                 255

Met Leu Ala Gly His Val Trp Arg Cys Ala Cys Lys Ala Arg Gly Leu
            260                 265                 270

Glu Val Asp Gln Gly Thr Lys Leu Tyr Ile Ala Thr Asp Gly Arg Ala
        275                 280                 285

Arg Leu Arg Pro Ser Leu Pro Pro Gly Tyr Phe Gly Asn Val Ile Phe
    290                 295                 300

Thr Ala Thr Pro Ile Ala Ile Ala Gly Asp Leu Glu Phe Lys Pro Val
305                 310                 315                 320

Trp Tyr Ala Ala Ser Lys Ile His Asp Ala Leu Ala Arg Met Asp Asn
                325                 330                 335

Asp Tyr Leu Arg Ser Ala Leu Asp Tyr Leu Glu Leu Gln Pro Asp Leu
        340                 345                 350

Lys Ala Leu Val Arg Gly Ala His Thr Phe Lys Cys Pro Asn Leu Gly
            355                 360                 365

Ile Thr Ser Trp Val Arg Leu Pro Ile His Asp Ala Asp Phe Gly Trp
    370                 375                 380

Gly Arg Pro Ile Phe Met Gly Pro Gly Gly Ile Ala Tyr Glu Gly Leu
385                 390                 395                 400

Ser Phe Ile Leu Pro Ser Pro Thr Asn Asp Gly Ser Met Ser Val Ala
                405                 410                 415

Ile Ser Leu Gln Gly Glu His Met Lys Leu Phe Gln Ser Phe Leu Tyr
        420                 425                 430

Asp Ile

<210> SEQ ID NO 10
```

```
<211> LENGTH: 434
<212> TYPE: PRT
<213> ORGANISM: Coffea arabica

<400> SEQUENCE: 10

Met Lys Ile Glu Val Lys Glu Ser Thr Met Val Arg Pro Ala His Glu
1               5                   10                  15

Thr Pro Arg Arg Asn Leu Trp Asn Ser Asn Val Asp Leu Val Val Pro
            20                  25                  30

Asn Phe His Thr Pro Ser Val Tyr Phe Tyr Arg Pro Thr Gly Ser Ser
        35                  40                  45

Asn Phe Phe Asp Ala Lys Val Leu Lys Asp Ala Leu Ser Arg Ala Leu
    50                  55                  60

Val Pro Phe Tyr Pro Met Ala Gly Arg Leu Lys Arg Asp Glu Asp Gly
65                  70                  75                  80

Arg Ile Glu Ile Glu Cys Asn Gly Glu Gly Val Leu Phe Val Glu Ala
                85                  90                  95

Glu Ser Asp Gly Val Val Asp Asp Phe Gly Asp Phe Ala Pro Thr Leu
            100                 105                 110

Glu Leu Arg Arg Leu Ile Pro Ala Val Asp Tyr Ser Gln Gly Ile Ser
        115                 120                 125

Ser Tyr Ala Leu Leu Val Leu Gln Val Thr Tyr Phe Lys Cys Gly Gly
    130                 135                 140

Val Ser Leu Gly Val Gly Met Gln His His Ala Ala Asp Gly Phe Ser
145                 150                 155                 160

Gly Leu His Phe Ile Asn Ser Trp Ser Asp Met Ala Arg Gly Leu Asp
                165                 170                 175

Val Thr Leu Pro Pro Phe Ile Asp Arg Thr Leu Leu Arg Ala Arg Asp
            180                 185                 190

Pro Pro Gln Pro Gln Phe Gln His Ile Glu Tyr Gln Pro Pro Pro Thr
        195                 200                 205

Leu Lys Val Ser Pro Gln Thr Ala Lys Ser Asp Ser Val Pro Glu Thr
    210                 215                 220

Ala Val Ser Ile Phe Lys Leu Thr Arg Glu Gln Ile Ser Ala Leu Lys
225                 230                 235                 240

Ala Lys Ser Lys Glu Asp Gly Asn Thr Ile Ser Tyr Ser Ser Tyr Glu
                245                 250                 255

Met Leu Ala Gly His Val Trp Arg Cys Ala Cys Lys Ala Arg Gly Leu
            260                 265                 270

Glu Val Asp Gln Gly Thr Lys Leu Tyr Ile Ala Thr Asp Gly Arg Ala
        275                 280                 285

Arg Leu Arg Pro Ser Leu Pro Pro Gly Tyr Phe Gly Asn Val Ile Phe
    290                 295                 300

Thr Ala Thr Leu Ile Ala Ile Ala Gly Asp Leu Glu Phe Lys Pro Val
305                 310                 315                 320

Trp Tyr Ala Ala Ser Lys Ile His Asp Ala Leu Ala Arg Met Asp Asn
                325                 330                 335

Asp Tyr Leu Arg Ser Ala Leu Asp Tyr Leu Glu Leu Gln Pro Asp Leu
            340                 345                 350

Lys Ala Leu Val Arg Gly Ala His Thr Phe Lys Cys Pro Asn Leu Gly
        355                 360                 365

Ile Thr Ser Trp Val Arg Leu Pro Ile His Asp Ala Asp Phe Gly Trp
    370                 375                 380

Gly Arg Pro Ile Phe Met Gly Pro Gly Gly Ile Ala Tyr Glu Gly Leu
385                 390                 395                 400
```

Ser Phe Ile Leu Pro Ser Pro Thr Asn Asp Gly Ser Met Ser Val Ala
                405                 410                 415

Ile Ser Leu Gln Gly Glu His Met Lys Leu Phe Gln Ser Phe Leu Tyr
            420                 425                 430

Asp Ile

<210> SEQ ID NO 11
<211> LENGTH: 430
<212> TYPE: PRT
<213> ORGANISM: Coffea canephora

<400> SEQUENCE: 11

Met Lys Ile Thr Val Lys Glu Thr Ala Met Val Arg Pro Ala Gln Pro
1               5                   10                  15

Thr Pro Thr Lys Arg Leu Trp Asn Ser Asn Leu Asp Leu Leu Val Ala
            20                  25                  30

Arg Ile His Ile Leu Thr Val Tyr Phe Tyr Lys Pro Asn Gly Ser Ala
            35                  40                  45

Asn Phe Phe Asp Thr Arg Val Leu Lys Glu Ala Leu Ser Asn Val Leu
    50                  55                  60

Val Ser Phe Tyr Pro Met Ala Gly Arg Leu Ala Arg Asp Glu Glu Gly
65                  70                  75                  80

Arg Ile Glu Ile Asp Cys Asn Gly Glu Gly Val Leu Phe Val Glu Ala
                85                  90                  95

Glu Ser Asp Ser Ser Val Asp Asp Phe Gly Asp Phe Ala Pro Ser Leu
            100                 105                 110

Glu Leu Arg Arg Leu Ile Pro Thr Val Asp Cys Ser Gly Asp Ile Ser
            115                 120                 125

Ser Tyr Pro Leu Val Ile Phe Gln Val Thr Arg Phe Lys Cys Gly Ala
    130                 135                 140

Ala Ala Leu Gly Ala Gly Val Gln His Asn Leu Ser Asp Gly Val Ser
145                 150                 155                 160

Ser Leu His Phe Ile Asn Thr Trp Ser Asp Ile Ala Arg Gly Leu Thr
                165                 170                 175

Ile Ala Val Pro Pro Phe Ile Asp Arg Thr Leu Ile Arg Ala Arg Asp
            180                 185                 190

Pro Pro Val Pro Val Phe Glu His Val Glu Tyr Tyr Pro Pro Pro Gln
            195                 200                 205

Leu Lys Ser Asp Ser Arg Ile Gln Glu Leu Lys Thr Gly Pro Arg Ala
    210                 215                 220

Ser Thr Thr Ala Val Leu Lys Ile Thr Pro Glu Gln Leu Ser Gln Leu
225                 230                 235                 240

Lys Ala Lys Ala Asn Asn Glu Gly Ser Thr Tyr Glu Ile Leu Ala Ala
                245                 250                 255

His Ile Trp Arg Thr Ala Cys Lys Ala Arg Gly Leu Thr Asn Asp Gln
            260                 265                 270

Ser Thr Lys Leu Tyr Val Ala Thr Asp Gly Arg Ser Arg Leu Ile Pro
            275                 280                 285

Pro Leu Pro Pro Gly Tyr Leu Gly Asn Val Val Phe Thr Ala Thr Pro
    290                 295                 300

Ile Ala Glu Ser Ser Asn Leu Gln Ser Glu Pro Leu Thr Asn Ser Ala
305                 310                 315                 320

Lys Arg Ile His Asn Ala Leu Ala Arg Met Asp Asn Asp Tyr Leu Arg
                325                 330                 335

-continued

Ser Ala Leu Asp Tyr Leu Glu Ile Gln Pro Asp Leu Ser Ala Leu Val
                340                 345                 350

Arg Gly Pro Arg His Phe Ala Ser Pro Asn Leu Asn Ile Asn Ser Trp
            355                 360                 365

Thr Arg Leu Pro Phe His Asp Ala Asp Phe Gly Trp Gly Arg Pro Ile
370                 375                 380

His Ile Gly Pro Ala Ile Ile Leu Tyr Glu Gly Thr Val Tyr Val Leu
385                 390                 395                 400

Pro Ser Pro Gly Lys Asp Arg Thr Leu Ser Leu Ala Val Cys Leu Asp
                405                 410                 415

Ala Asp His Met Pro Leu Phe Gln Arg Phe Leu Tyr Asp Phe
            420                 425                 430

<210> SEQ ID NO 12
<211> LENGTH: 430
<212> TYPE: PRT
<213> ORGANISM: Coffea arabica
<220> FEATURE:
<221> NAME/KEY: MISC_FEATURE
<222> LOCATION: (272)..(272)
<223> OTHER INFORMATION: Xaa is any naturally occuring amino acid,
      preferably a Gln or similar.  A stop codon corresponding to this
      location was found in the nucleic acid sequence but shown to be an
      artifact of cloning.

<400> SEQUENCE: 12

Met Lys Ile Thr Val Lys Glu Thr Ala Met Val Arg Pro Ala Gln Pro
1               5                   10                  15

Thr Pro Thr Lys Arg Leu Trp Asn Ser Asn Leu Asp Leu Leu Val Ala
                20                  25                  30

Arg Ile His Ile Leu Thr Ile Tyr Phe Tyr Lys Pro Asn Gly Ser Ala
            35                  40                  45

Asn Phe Phe Asp Thr Arg Val Leu Lys Glu Ala Leu Ser Asn Val Leu
50                  55                  60

Val Ser Phe Tyr Pro Met Ala Gly Arg Leu Ala Arg Asp Glu Glu Gly
65                  70                  75                  80

Arg Ile Glu Ile Asp Cys Asn Gly Glu Gly Val Leu Phe Val Glu Ala
                85                  90                  95

Glu Ser Asp Ser Ser Val Asp Asp Phe Gly Asp Phe Ala Pro Ser Leu
            100                 105                 110

Glu Leu Arg Arg Leu Ile Pro Thr Val Asp Cys Ser Gly Asp Ile Ser
        115                 120                 125

Ser Tyr Pro Leu Val Ile Phe Gln Val Thr Arg Phe Lys Cys Gly Ala
    130                 135                 140

Ala Ala Leu Gly Ala Gly Val Gln His Asn Leu Ser Asp Gly Val Ser
145                 150                 155                 160

Ser Leu His Phe Ile Asn Thr Trp Ser Asp Ile Ala Arg Gly Leu Thr
                165                 170                 175

Ile Ala Val Pro Pro Phe Ile Asp Arg Thr Leu Ile His Ala Arg Asp
            180                 185                 190

Pro Pro Val Pro Val Phe Glu His Val Glu Tyr Pro Pro Pro Gln
        195                 200                 205

Leu Lys Ser Asp Ser Arg Ile Gln Glu Leu Lys Thr Gly Pro Arg Ala
    210                 215                 220

Ser Thr Thr Ala Val Leu Lys Ile Thr Pro Glu Gln Leu Ser Gln Leu
225                 230                 235                 240

Lys Ala Lys Ala Asn Asn Glu Gly Ser Thr Tyr Glu Ile Leu Ala Ala
                245                 250                 255

His Ile Trp Arg Thr Ala Cys Lys Ala Arg Gly Pro Thr Asn Asp Xaa
            260                 265                 270

Ser Thr Lys Leu Tyr Val Ala Thr Asp Gly Arg Ser Arg Leu Ile Pro
        275                 280                 285

Pro Leu Pro Pro Gly Tyr Leu Gly Asn Val Val Phe Thr Ala Thr Pro
    290                 295                 300

Ile Ala Glu Ser Ser Asp Leu Gln Ser Glu Pro Leu Thr Asn Ser Ala
305                 310                 315                 320

Lys Arg Ile His Asn Ala Leu Ala Arg Met Asp Asn Asp Tyr Leu Arg
                325                 330                 335

Ser Ala Leu Asp Tyr Leu Glu Ile Gln Pro Asp Leu Ser Ala Leu Val
            340                 345                 350

Arg Gly Pro Arg His Phe Ala Ser Pro Asn Leu Asn Ile Asn Ser Trp
        355                 360                 365

Thr Gly Leu Pro Phe His Asp Ala Asp Phe Gly Trp Gly Arg Pro Ile
    370                 375                 380

His Ile Gly Pro Ala Ile Ile Leu Tyr Glu Gly Thr Val Tyr Val Leu
385                 390                 395                 400

Pro Gly Pro Gly Lys Asp Arg Thr Leu Ser Leu Ala Val Cys Leu Asp
                405                 410                 415

Ala Asp His Met Pro Leu Phe Gln Lys Phe Leu Tyr Asp Phe
            420                 425                 430

<210> SEQ ID NO 13
<211> LENGTH: 508
<212> TYPE: PRT
<213> ORGANISM: Coffea canephora

<400> SEQUENCE: 13

Met Ala Leu Leu Leu Ile Leu Leu Pro Val Ala Phe Ile Phe Leu Ala
1               5                   10                  15

Tyr Ser Leu Tyr Glu Arg Leu Arg Phe Lys Leu Pro Pro Gly Pro Arg
            20                  25                  30

Pro Lys Pro Val Val Gly Asn Ile Tyr Asp Ile Lys Pro Val Arg Phe
        35                  40                  45

Lys Cys Tyr Ala Glu Trp Ser Lys Leu Tyr Gly Pro Ile Phe Ser Val
    50                  55                  60

Tyr Phe Gly Ser Gln Leu Asn Thr Val Val Asn Thr Ala Glu Leu Ala
65                  70                  75                  80

Lys Glu Val Leu Lys Asp Asn Asp Gln Gln Leu Ala Asp Arg Tyr Arg
                85                  90                  95

Ser Arg Pro Ser Ala Arg Met Ser Arg Asn Gly Gln Asp Leu Ile Trp
            100                 105                 110

Ala Asp Tyr Gly Pro His Tyr Val Lys Val Arg Lys Leu Cys Asn Leu
        115                 120                 125

Glu Leu Phe Thr Pro Lys Arg Leu Glu Gly Leu Arg Pro Leu Arg Glu
    130                 135                 140

Asp Glu Val Thr Ala Met Val Asp Ser Ile Phe Lys Asp Cys Thr Lys
145                 150                 155                 160

Pro Glu Asn Lys Gly Lys Ser Leu Leu Met Arg Asn Tyr Leu Gly Ser
                165                 170                 175

Val Ala Phe Asn Asn Ile Thr Arg Leu Thr Phe Gly Lys Arg Phe Met
            180                 185                 190

Asn Ser Glu Gly Val Val Asp Glu Gln Gly Gln Glu Phe Lys Gly Ile
        195                 200                 205

-continued

Val Ser Asn Gly Ile Arg Ile Gly Ala Lys Leu Ser Val Ala Asp His
    210                 215                 220

Ile Pro Trp Leu Arg Trp Met Phe Val Gly Glu Asn Glu Asp Leu Asp
225                 230                 235                 240

Lys His Asn Ala Arg Arg Asp Lys Leu Thr Arg Met Ile Met Glu Glu
                245                 250                 255

His Thr Leu Ala Arg Gln Lys Ser Gly Asn Thr Lys Gln His Phe Val
            260                 265                 270

Asp Ala Leu Leu Thr Leu Gln Lys Gln Tyr Glu Leu Ser Asp Asp Thr
        275                 280                 285

Val Ile Gly Leu Leu Trp Asp Met Ile Thr Ala Gly Met Asp Thr Thr
    290                 295                 300

Thr Ile Ser Val Glu Trp Ala Met Ala Glu Leu Val Lys Asn Pro Arg
305                 310                 315                 320

Val Gln Gln Lys Ala Gln Glu Glu Leu Asp Arg Val Ile Gly Ser Asp
                325                 330                 335

Arg Ile Met Thr Glu Ala Asp Phe Ala Lys Leu Pro Tyr Leu Gln Cys
            340                 345                 350

Val Ala Lys Glu Ala Leu Arg Leu His Pro Pro Thr Pro Leu Met Leu
        355                 360                 365

Pro His Arg Ala Asn Ala Asn Val Lys Ile Gly Gly Tyr Asp Ile Pro
    370                 375                 380

Lys Gly Ser Ile Val His Val Asn Val Trp Ala Ile Ala Arg Asp Pro
385                 390                 395                 400

Ala Ala Trp Lys Asn Pro Leu Glu Phe Arg Pro Glu Arg Phe Leu Glu
                405                 410                 415

Glu Asp Val Asp Ile Lys Gly His Asp Tyr Arg Leu Leu Pro Phe Gly
            420                 425                 430

Ala Gly Arg Arg Ile Cys Pro Gly Ala Gln Leu Ala Leu Asn Leu Val
        435                 440                 445

Thr Ser Met Leu Gly His Leu Leu His His Phe Thr Trp Ser Pro Pro
    450                 455                 460

Pro Gly Val Arg Pro Glu Glu Ile Asp Leu Glu Glu Ser Pro Gly Thr
465                 470                 475                 480

Val Thr Tyr Met Arg Thr Pro Leu Gln Ala Val Ala Thr Pro Arg Leu
                485                 490                 495

Pro Ala His Leu Tyr Asn Arg Val Pro Val Glu Leu
            500                 505

<210> SEQ ID NO 14
<211> LENGTH: 247
<212> TYPE: PRT
<213> ORGANISM: Coffea canephora

<400> SEQUENCE: 14

Met Ala Gln Asn Gly Glu Gly Lys Asp Ser Gln Asn Leu Arg His Gln
1               5                   10                  15

Glu Val Gly His Lys Ser Leu Leu Gln Ser Asp Ala Leu Tyr Gln Tyr
            20                  25                  30

Ile Leu Glu Thr Ser Val Tyr Pro Arg Glu Pro Glu Pro Met Lys Glu
        35                  40                  45

Leu Arg Glu Leu Thr Ala Lys His Pro Trp Asn Ile Met Thr Thr Ser
    50                  55                  60

Ala Asp Glu Gly Gln Phe Leu Asn Met Ile Ile Lys Leu Ile Asn Ala
65                  70                  75                  80

Lys Lys Thr Met Glu Ile Gly Val Tyr Thr Gly Tyr Ser Leu Leu Ala
                85                  90                  95

Thr Ala Leu Ala Leu Pro Glu Asp Gly Lys Ile Leu Ala Met Asp Ile
            100                 105                 110

Asn Arg Glu Asn Tyr Glu Leu Gly Leu Pro Val Ile Glu Arg Ala Gly
            115                 120                 125

Val Ser His Lys Ile Asp Phe Arg Glu Gly Pro Ala Leu Pro Val Leu
        130                 135                 140

Asp Glu Leu Ile Glu Asp Asp Lys Asn His Gly Ser Phe Asp Phe Ile
145                 150                 155                 160

Phe Val Asp Ala Asp Lys Asp Asn Tyr Leu Asn Tyr His Lys Arg Ile
                165                 170                 175

Ile Glu Leu Val Lys Val Gly Gly Met Ile Gly Tyr Asp Asn Thr Leu
            180                 185                 190

Trp Asn Gly Ser Val Val Ala Pro Pro Asp Ala Pro Met Arg Lys Tyr
            195                 200                 205

Val Arg Tyr Tyr Arg Asp Phe Val Leu Glu Leu Asn Lys Ala Leu Ala
        210                 215                 220

Ala Asp Pro Arg Ile Glu Ile Cys Met Leu Pro Val Gly Asp Gly Ile
225                 230                 235                 240

Thr Leu Cys Arg Arg Val Ser
                245

<210> SEQ ID NO 15
<211> LENGTH: 229
<212> TYPE: PRT
<213> ORGANISM: Coffea arabica

<400> SEQUENCE: 15

Met Glu Asn Lys Gly Leu Leu Gln Ser Arg Glu Leu Tyr Gln Tyr Leu
1               5                   10                  15

Leu Glu Thr Ser Val Tyr Pro His Glu Leu Gln Pro Leu Lys Glu Leu
            20                  25                  30

Arg Asp Val Thr Ala Ser His Pro Trp Ala Thr Met Ala Thr Ala Pro
        35                  40                  45

Asp Ala Gly Gln Leu Ile Ala Met Leu Leu Lys Leu Ile Ser Ala Lys
    50                  55                  60

Lys Thr Ile Glu Ile Gly Val Phe Thr Gly Tyr Ser Leu Leu Leu Thr
65                  70                  75                  80

Ala Leu Thr Ile Pro Asp Asp Gly Arg Ile Val Ala Ile Asp Gln Asn
                85                  90                  95

Arg Asp Thr Tyr Glu Ile Gly Leu Pro Ile Ile Arg Lys Ala Ala Val
            100                 105                 110

Glu His Lys Ile Asp Phe Ile Glu Ser Glu Ala Leu Pro Val Leu Asp
        115                 120                 125

Lys Leu Leu Glu Glu Asn Leu Asn His Glu Ala Phe Asp Phe Ala Phe
    130                 135                 140

Val Asp Ala Asp Lys Leu Asn Tyr Leu Lys Tyr His Glu Lys Leu Leu
145                 150                 155                 160

Lys Leu Leu Lys Leu Gly Gly Ile Val Val Tyr Asp Asn Thr Leu Trp
                165                 170                 175

Gly Gly Leu Val Ala Leu Pro Glu Glu Ser Val Ala Glu Glu Met Lys
            180                 185                 190

Ala Gly Arg His Phe Thr Ile Glu Phe Asn Lys Leu Leu Ala Ala Asp
        195                 200                 205

```
Thr Arg Val Gln Ile Ser Gln Val Pro Leu Gly Asp Gly Ile Thr Ile
    210                 215                 220

Cys Lys Arg Leu His
225
```

<210> SEQ ID NO 16
<211> LENGTH: 238
<212> TYPE: PRT
<213> ORGANISM: Coffea canephora

<400> SEQUENCE: 16

```
Met Ala Lys Glu Gly Gly Ser Lys Met Lys Thr Ile Leu Gln Ser Glu
1               5                   10                  15

Ala Leu Gln Lys Tyr Ile Leu Asn Thr Ser Thr Tyr Pro Lys Glu His
            20                  25                  30

Glu Gln Leu Lys Glu Leu Arg Glu Glu Thr Ala Arg Lys Tyr Gly Ala
        35                  40                  45

Arg Ala Ile Ile Gly Val Pro Pro Asp Glu Gly Leu Phe Leu Ser Met
    50                  55                  60

Phe Leu Lys Val Met Asn Ala Lys Lys Thr Leu Glu Ile Gly Val Phe
65                  70                  75                  80

Thr Gly Tyr Ser Leu Leu Thr Thr Ala Leu Ala Leu Pro Asp Asp Gly
                85                  90                  95

Gln Ile Val Ala Ile Asp Pro Asp Gln Gly Ala Phe Glu Val Gly Leu
            100                 105                 110

Lys Phe Ile Lys Lys Ala Gly Val Glu Asn Lys Ile Lys Phe Ile Lys
        115                 120                 125

Ser Asp Gly Ile Ser Ala Leu Asn Asp Leu Leu Asn Asn Glu Ala Ser
    130                 135                 140

Glu Ala Thr Phe Asp Phe Ala Phe Val Asp Ala Asp Lys Pro Ser Tyr
145                 150                 155                 160

Ile Gln Tyr His Glu Gln Leu Ile Lys Leu Val Lys Ile Gly Gly Ile
                165                 170                 175

Ile Ala Tyr Asp Asn Thr Leu Tyr Gly Gly Tyr Val Val Ser Glu Glu
            180                 185                 190

Ile Glu Met His Glu Gly Ser Thr Val Asn Arg Lys Ala Ile Ile Gln
        195                 200                 205

Phe Asn Asn Tyr Ile Ala Ser Asp Pro Arg Val Glu Ile Ser Gln Val
    210                 215                 220

Pro Ile Gly Asp Gly Val Thr Leu Cys Arg Arg Ile Ile Ala
225                 230                 235
```

<210> SEQ ID NO 17
<211> LENGTH: 209
<212> TYPE: DNA
<213> ORGANISM: Coffea canephora
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (196)..(197)
<223> OTHER INFORMATION: n is a, c, g, or t

<400> SEQUENCE: 17

```
tacaactttc aaccatgaaa atcgaggtga aggaatcgac tatggtgaga cctgcccaag      60
aaactcctgg gaggaacttg tggaactcga acgtggactt ggtggtgcca aatttccaca    120
```

-continued

| cccctagcgt ctacttctat aggccgacgg gatcatcgaa tttctttgat gccaaagtgc | 180 |
| taanggacgc tttganncga gcccttgtc | 209 |

<210> SEQ ID NO 18
<211> LENGTH: 1465
<212> TYPE: DNA
<213> ORGANISM: Coffea canephora

<400> SEQUENCE: 18

| ggatcatcga atttctttga tgccaaagtg ctaaaggacg ctttgagccg agcccttgtc | 60 |
| ccgttctacc caatggctgg taggttaaag agagacgaag atgggcggat tgagattgag | 120 |
| tgcaatggtg aaggcgtgct tttcgtggag gccgagtctg atggagtagt tgatgatttc | 180 |
| ggtgactttg caccaacttt agagcttcgt agactcattc ctgcagttga ttattctcaa | 240 |
| ggaatatcaa gctacgctct cctagtgctg caggtgacat atttcaagtg tggtggagtc | 300 |
| tctcttggtg ttggcatgca acatcatgca gctgatggat tttcaggtct tcatttcatc | 360 |
| aattcatggt ctgatatggc ccgtggcctt gatgtgaccc tgccaccatt catagaccgc | 420 |
| accctcctcc gtgcccgcga tccgccccag cctcaattcc agcacattga gtaccaacct | 480 |
| cctccagcct taaaagtttc cccgcaaact gcaaaatctg actcagttcc tgaaactgcg | 540 |
| gtgtccatct tcaagttaac cagggagcaa atcagtgccc tgaaagccaa gtccaaggaa | 600 |
| gatggaaaca ccattagcta tagctcctac gaaatgttgg caggccatgt atggcgctgt | 660 |
| gcttgcaagg cacgaggact cgaagttgat caaggaacaa aattgtacat tgctactgat | 720 |
| ggacgggcaa gacttaggcc ttcgctccca cctggctatt ttggcaatgt catcttcacg | 780 |
| gcaaccccga tagctatagc tggtgacctt gaattcaagc cagtctggta tgctgcaagt | 840 |
| aaaatccacg atgcattggc gaggatggac aacgactact taaggtcagc tcttgattac | 900 |
| ttggaattac agcctgattt gaaggccctg gttcgtggtg cccatacttt caagtgtcca | 960 |
| aatctgggga tcacaagctg ggtcaggtta cccatccatg atgctgattt tggctggggt | 1020 |
| cggcccatat ttatgggtcc tggtggcatc gcttatgaag gtttaagctt tatattgcct | 1080 |
| agtccaacca atgatggaag catgtcagta gctatttcat tgcagggcga gcacatgaaa | 1140 |
| ctcttccaga gtttcttgta tgacatttga acgggagcac atcacatgaa ttttcacgct | 1200 |
| tgtattaata gctttcggtt ccgggccagc tattcatgcg gtggtggttt cttgagtaat | 1260 |
| tgtttaagct tatgaagaac cactgttctg ttttgtacct atgtggacaa taattcttgt | 1320 |
| ctaagttcct tgtgcatgta atgatggtga aaggataagg ttcatttcat tttattgttt | 1380 |
| tgtcatttga gttctaaagt tgtaaaaaaa aaaaaaaaa aaaaaaaaa aaaaaaaaa | 1440 |
| aaaaaaaaaa aaaaaaaaaa aaaaa | 1465 |

<210> SEQ ID NO 19
<211> LENGTH: 685
<212> TYPE: DNA
<213> ORGANISM: Coffea arabica

<400> SEQUENCE: 19

| tttcttaggc gcggtaggta agtcccccaa aacaaattat atagtccccc tacggtctcg | 60 |
| cactcttaa catttttttc ccgttttgtt aggacgcaga tcagattcat ttcgattaaa | 120 |
| gtccaaccca cttcgaacaa caccatacct acaacatcat tgtccttacc acttctccca | 180 |
| ttagccagcc tgccacctcc tcctcctcct cccctcttc cttttgaatt tcttatccc | 240 |
| accacccaac attcttcttc cttctcaact cttcaggtac gtttaatgca aatttcacgt | 300 |

```
aatatttcac gttcgaaatc cattcttcat caccattaaa ctaatcaaag tatgtttatt      360
gcaccatttt cttttatgtt ttttggggta cagttgttgt acgtgtcaag caaggatcat      420
acaactttca accatgaaaa tcaaggtgaa ggaatcgact atggtgagac ctgcccaaga      480
aactcctagg aggaacttgt ggaactcgaa cgtggacttg gtggtgccaa atttccacac      540
ccctagcgtc tacttctata ggccgacggg atcatcgaat ttctttgatg ccaaagtgct      600
gaaggacgct ctgagccgag cccttgtccc gttctaccca atggctggta ggttaaagag      660
agacgaagat gggcggattg agatt                                             685
```

<210> SEQ ID NO 20
<211> LENGTH: 435
<212> TYPE: PRT
<213> ORGANISM: Nicotiana tabacum

<400> SEQUENCE: 20

```
Met Lys Ile Glu Val Lys Glu Ser Thr Met Val Lys Pro Ala Ala Glu
1               5                   10                  15

Thr Pro Gln Gln Arg Leu Trp Asn Ser Asn Val Asp Leu Val Val Pro
            20                  25                  30

Asn Phe His Thr Pro Ser Val Tyr Phe Tyr Arg Pro Thr Gly Ser Pro
        35                  40                  45

Asn Phe Phe Asp Gly Lys Val Leu Lys Glu Ala Leu Ser Lys Ala Leu
    50                  55                  60

Val Pro Phe Tyr Pro Met Ala Gly Arg Leu Cys Arg Asp Glu Asp Gly
65                  70                  75                  80

Arg Ile Glu Ile Asp Cys Lys Gly Gln Gly Val Leu Phe Val Glu Ala
                85                  90                  95

Glu Ser Asp Gly Val Val Asp Asp Phe Gly Asp Phe Ala Pro Thr Leu
            100                 105                 110

Glu Leu Arg Gln Leu Ile Pro Ala Val Asp Tyr Ser Gln Gly Ile Gln
        115                 120                 125

Ser Tyr Ala Leu Leu Val Leu Gln Ile Thr His Phe Lys Cys Gly Gly
    130                 135                 140

Val Ser Leu Gly Val Gly Met Gln His His Ala Ala Asp Gly Ala Ser
145                 150                 155                 160

Gly Leu His Phe Ile Asn Thr Trp Ser Asp Met Ala Arg Gly Leu Asp
                165                 170                 175

Leu Thr Ile Pro Pro Phe Ile Asp Arg Thr Leu Leu Arg Ala Arg Asp
            180                 185                 190

Pro Pro Gln Pro Gln Phe Pro His Val Glu Tyr Gln Pro Pro Pro Thr
        195                 200                 205

Leu Lys Val Thr Pro Glu Asn Thr Pro Ile Ser Glu Ala Val Pro Glu
    210                 215                 220

Thr Ser Val Ser Ile Phe Lys Leu Thr Arg Asp Gln Ile Asn Thr Leu
225                 230                 235                 240

Lys Ala Lys Ser Lys Glu Asp Gly Asn Thr Val Asn Tyr Ser Ser Tyr
                245                 250                 255

Glu Met Leu Ala Gly His Val Trp Arg Ser Thr Cys Met Ala Arg Gly
            260                 265                 270

Leu Ala His Asp Gln Glu Thr Lys Leu Tyr Ile Ala Thr Asp Gly Arg
        275                 280                 285

Ser Arg Leu Arg Pro Ser Leu Pro Pro Gly Tyr Phe Gly Asn Val Ile
    290                 295                 300

Phe Thr Thr Thr Pro Ile Ala Val Ala Gly Asp Ile Gln Ser Lys Pro
```

```
                305                 310                 315                 320
Ile Trp Tyr Ala Ala Ser Lys Leu His Asp Ala Leu Ala Arg Met Asp
                    325                 330                 335

Asn Asp Tyr Leu Arg Ser Ala Leu Asp Tyr Leu Glu Leu Gln Pro Asp
                340                 345                 350

Leu Lys Ala Leu Val Arg Gly Ala His Thr Phe Lys Cys Pro Asn Leu
            355                 360                 365

Gly Ile Thr Ser Trp Ser Arg Leu Pro Ile His Asp Ala Asp Phe Gly
        370                 375                 380

Trp Gly Arg Pro Ile Phe Met Gly Pro Gly Ile Ala Tyr Glu Gly
385                 390                 395                 400

Leu Ser Phe Ile Leu Pro Ser Pro Thr Asn Asp Gly Ser Gln Ser Val
                405                 410                 415

Ala Ile Ser Leu Gln Ala Glu His Met Lys Leu Phe Glu Lys Phe Leu
                420                 425                 430

Tyr Asp Phe
        435

<210> SEQ ID NO 21
<211> LENGTH: 433
<212> TYPE: PRT
<213> ORGANISM: Arabidopsis thaliana

<400> SEQUENCE: 21

Met Lys Ile Asn Ile Arg Asp Ser Thr Met Val Arg Pro Ala Thr Glu
1               5                   10                  15

Thr Pro Ile Thr Asn Leu Trp Asn Ser Asn Val Asp Leu Val Ile Pro
                20                  25                  30

Arg Phe His Thr Pro Ser Val Tyr Phe Tyr Arg Pro Thr Gly Ala Ser
            35                  40                  45

Asn Phe Phe Asp Pro Gln Val Met Lys Glu Ala Leu Ser Lys Ala Leu
        50                  55                  60

Val Pro Phe Tyr Pro Met Ala Gly Arg Leu Lys Arg Asp Asp Asp Gly
65                  70                  75                  80

Arg Ile Glu Ile Asp Cys Asn Gly Ala Gly Val Leu Phe Val Val Ala
                85                  90                  95

Asp Thr Pro Ser Val Ile Asp Asp Phe Gly Asp Phe Ala Pro Thr Leu
            100                 105                 110

Asn Leu Arg Gln Leu Ile Pro Glu Val Asp His Ser Ala Gly Ile His
        115                 120                 125

Ser Phe Pro Leu Leu Val Leu Gln Val Thr Phe Phe Lys Cys Gly Gly
    130                 135                 140

Ala Ser Leu Gly Val Gly Met Gln His His Ala Ala Asp Gly Phe Ser
145                 150                 155                 160

Gly Leu His Phe Ile Asn Thr Trp Ser Asp Met Ala Arg Gly Leu Asp
                165                 170                 175

Leu Thr Ile Pro Pro Phe Ile Asp Arg Thr Leu Leu Arg Ala Arg Asp
            180                 185                 190

Pro Pro Gln Pro Ala Phe His His Val Glu Tyr Gln Pro Ala Pro Ser
        195                 200                 205

Met Lys Ile Pro Leu Asp Pro Ser Lys Ser Gly Pro Glu Asn Thr Thr
    210                 215                 220

Val Ser Ile Phe Lys Leu Thr Arg Asp Gln Leu Val Ala Leu Lys Ala
225                 230                 235                 240

Lys Ser Lys Glu Asp Gly Asn Thr Val Ser Tyr Ser Ser Tyr Glu Met
```

```
                        245                 250                 255
Leu Ala Gly His Val Trp Arg Ser Val Gly Lys Ala Arg Gly Leu Pro
                260                 265                 270

Asn Asp Gln Glu Thr Lys Leu Tyr Ile Ala Thr Asp Gly Arg Ser Arg
            275                 280                 285

Leu Arg Pro Gln Leu Pro Pro Gly Tyr Phe Gly Asn Val Ile Phe Thr
        290                 295                 300

Ala Thr Pro Leu Ala Val Ala Gly Asp Leu Leu Ser Lys Pro Thr Trp
305                 310                 315                 320

Tyr Ala Ala Gly Gln Ile His Asp Phe Leu Val Arg Met Asp Asp Asn
                325                 330                 335

Tyr Leu Arg Ser Ala Leu Asp Tyr Leu Glu Met Gln Pro Asp Leu Ser
            340                 345                 350

Ala Leu Val Arg Gly Ala His Thr Tyr Lys Cys Pro Asn Leu Gly Ile
        355                 360                 365

Thr Ser Trp Val Arg Leu Pro Ile Tyr Asp Ala Asp Phe Gly Trp Gly
    370                 375                 380

Arg Pro Ile Phe Met Gly Pro Gly Ile Pro Tyr Glu Gly Leu Ser
385                 390                 395                 400

Phe Val Leu Pro Ser Pro Thr Asn Asp Gly Ser Leu Ser Val Ala Ile
                405                 410                 415

Ala Leu Gln Ser Glu His Met Lys Leu Phe Glu Lys Phe Leu Phe Glu
            420                 425                 430

Ile

<210> SEQ ID NO 22
<211> LENGTH: 431
<212> TYPE: PRT
<213> ORGANISM: Ipomoea batatas

<400> SEQUENCE: 22

Met Ala Ser Glu Lys Phe Lys Ile Ser Ile Lys Glu Ser Thr Met Val
1               5                   10                  15

Lys Pro Ala Lys Pro Thr Pro Ala Lys Arg Leu Trp Asn Ser Asn Leu
            20                  25                  30

Asp Leu Ile Val Gly Arg Ile His Leu Leu Thr Val Tyr Phe Tyr Arg
        35                  40                  45

Pro Asn Gly Ser Pro Asn Phe Phe Asp Ser Lys Val Met Lys Glu Ala
    50                  55                  60

Leu Ser Asn Val Leu Val Ser Phe Tyr Pro Met Ala Gly Arg Leu Ala
65                  70                  75                  80

Arg Asp Gly Glu Gly Arg Ile Glu Ile Asp Cys Asn Glu Glu Gly Val
                85                  90                  95

Leu Phe Val Glu Ala Glu Ser Asp Ala Cys Val Asp Asp Phe Gly Asp
            100                 105                 110

Phe Thr Pro Ser Leu Glu Leu Arg Lys Phe Ile Pro Thr Val Asp Thr
        115                 120                 125

Ser Gly Asp Ile Ser Ser Phe Pro Leu Ile Ile Phe Gln Val Thr Arg
    130                 135                 140

Phe Lys Cys Gly Gly Val Cys Leu Gly Thr Gly Val Phe His Thr Leu
145                 150                 155                 160

Ser Asp Gly Val Ser Ser Leu His Phe Ile Asn Thr Trp Ser Asp Met
                165                 170                 175

Ala Arg Gly Leu Ser Val Ala Ile Pro Pro Phe Ile Asp Arg Thr Leu
            180                 185                 190
```

Leu Arg Ala Arg Asp Pro Pro Thr Pro Ala Phe Glu His Ser Glu Tyr
            195                 200                 205

Asp Gln Pro Pro Lys Leu Lys Ser Val Pro Glu Ser Lys Arg Gly Ser
        210                 215                 220

Ser Ala Ser Thr Thr Met Leu Lys Ile Thr Pro Glu Gln Leu Ala Leu
225                 230                 235                 240

Leu Lys Thr Lys Ser Lys His Glu Gly Ser Thr Tyr Glu Ile Leu Ala
            245                 250                 255

Ala His Ile Trp Arg Cys Ala Cys Lys Ala Arg Gly Leu Thr Asp Asp
        260                 265                 270

Gln Ala Thr Lys Leu Tyr Val Ala Thr Asp Gly Arg Ser Arg Leu Cys
            275                 280                 285

Pro Pro Leu Pro Pro Gly Tyr Leu Gly Asn Val Val Phe Thr Ala Thr
        290                 295                 300

Pro Met Ala Glu Ser Gly Glu Leu Gln Ser Glu Pro Leu Thr Asn Ser
305                 310                 315                 320

Ala Lys Arg Ile His Ser Ala Leu Ser Arg Met Asp Asp Glu Tyr Leu
            325                 330                 335

Arg Ser Ala Leu Asp Phe Leu Glu Cys Gln Pro Asp Leu Ser Lys Leu
        340                 345                 350

Ile Arg Gly Ser Asn Tyr Phe Ala Ser Pro Asn Leu Asn Ile Asn Ser
            355                 360                 365

Trp Thr Arg Leu Pro Val His Glu Ser Asp Phe Gly Trp Gly Arg Pro
        370                 375                 380

Ile His Met Gly Pro Ala Cys Ile Leu Tyr Glu Gly Thr Val Tyr Ile
385                 390                 395                 400

Leu Pro Ser Pro Asn Lys Asp Arg Thr Leu Ser Leu Ala Val Cys Leu
            405                 410                 415

Asp Ala Glu His Met Pro Leu Phe Lys Glu Phe Leu Tyr Asp Phe
        420                 425                 430

<210> SEQ ID NO 23
<211> LENGTH: 436
<212> TYPE: PRT
<213> ORGANISM: Lycopersicon esculentum

<400> SEQUENCE: 23

Met Gly Ser Glu Lys Met Met Lys Ile Asn Ile Lys Glu Ser Thr Leu
1               5                   10                  15

Val Lys Pro Ser Lys Pro Thr Pro Thr Lys Arg Leu Trp Ser Ser Asn
            20                  25                  30

Leu Asp Leu Ile Val Gly Arg Ile His Leu Leu Thr Val Tyr Phe Tyr
        35                  40                  45

Lys Pro Asn Gly Ser Ser Asn Phe Phe Asp Ser Lys Ile Met Lys Glu
    50                  55                  60

Ala Leu Ser Asn Val Leu Val Ser Phe Tyr Pro Met Ala Gly Arg Leu
65                  70                  75                  80

Ala Arg Asp Glu Gln Gly Arg Ile Glu Ile Asn Cys Asn Gly Glu Gly
            85                  90                  95

Val Leu Phe Val Glu Ala Glu Ser Asp Ala Phe Val Asp Asp Phe Gly
            100                 105                 110

Asp Phe Thr Pro Ser Leu Glu Leu Arg Lys Leu Ile Pro Thr Val Asp
        115                 120                 125

Thr Ser Gly Asp Ile Ser Thr Phe Pro Leu Ile Ile Phe Gln Val Thr
    130                 135                 140

```
Arg Phe Lys Cys Gly Gly Val Ser Leu Gly Gly Val Phe His Thr
145                 150                 155                 160

Leu Ser Asp Gly Leu Ser Ser Ile His Phe Ile Asn Thr Trp Ser Asp
            165                 170                 175

Ile Ala Arg Gly Leu Ser Val Ala Ile Pro Pro Phe Ile Asp Arg Thr
            180                 185                 190

Leu Leu Arg Ala Arg Asp Pro Pro Thr Ser Ser Phe Glu His Val Glu
            195                 200                 205

Tyr His Pro Pro Pro Ser Leu Ile Ser Ser Lys Ser Leu Glu Ser
210                 215                 220

Thr Ser Pro Lys Pro Ser Thr Thr Thr Met Leu Lys Phe Ser Ser Asp
225                 230                 235                 240

Gln Leu Gly Leu Leu Lys Ser Lys Ser Lys His Asp Gly Ser Thr Tyr
                245                 250                 255

Glu Ile Leu Ala Ala His Ile Trp Arg Cys Thr Cys Lys Ala Arg Ala
            260                 265                 270

Leu Ser Asp Asp Gln Leu Thr Lys Leu His Val Ala Thr Asp Gly Arg
            275                 280                 285

Ser Arg Leu Cys Pro Pro Leu Pro Pro Gly Tyr Leu Gly Asn Val Val
        290                 295                 300

Phe Thr Gly Thr Pro Met Ala Lys Ser Ser Glu Leu Leu Gln Glu Pro
305                 310                 315                 320

Leu Thr Asn Ser Ala Lys Arg Ile His Ser Ala Leu Ser Lys Met Asp
                325                 330                 335

Asp Asn Tyr Leu Arg Ser Ala Leu Asp Tyr Leu Glu Leu Leu Pro Asp
            340                 345                 350

Leu Ser Ala Leu Ile Arg Gly Pro Thr Tyr Phe Ala Ser Pro Asn Leu
            355                 360                 365

Asn Ile Asn Ser Trp Thr Arg Leu Pro Val His Asp Ser Asp Phe Gly
370                 375                 380

Trp Gly Arg Pro Ile His Met Gly Pro Ala Cys Ile Leu Tyr Glu Gly
385                 390                 395                 400

Thr Val Tyr Ile Leu Pro Ser Pro Asn Ser Lys Asp Arg Asn Leu Arg
                405                 410                 415

Leu Ala Val Cys Leu Asp Ala Asp His Met Pro Leu Phe Glu Lys Tyr
                420                 425                 430

Leu Tyr Glu Phe
        435

<210> SEQ ID NO 24
<211> LENGTH: 430
<212> TYPE: PRT
<213> ORGANISM: Lycopersicon esculentum

<400> SEQUENCE: 24

Met Gly Ser Glu Lys Met Met Lys Ile Asn Ile Lys Glu Ser Thr Leu
1               5                   10                  15

Val Lys Pro Ser Lys Pro Thr Pro Thr Lys Arg Ile Trp Ser Ser Asn
                20                  25                  30

Leu Asp Leu Ile Val Gly Arg Ile His Leu Leu Thr Val Tyr Phe Tyr
            35                  40                  45

Lys Pro Asn Gly Ser Ser Asn Phe Asp Lys Val Ile Lys Glu
    50                  55                  60

Ala Leu Ser Asn Val Leu Val Ser Phe Tyr Pro Met Ala Gly Arg Leu
65                  70                  75                  80
```

Gly Arg Asp Glu Gln Gly Arg Ile Glu Val Asn Cys Asn Glu Gly
            85                  90                  95

Val Leu Phe Val Glu Ala Glu Ser Asp Ser Cys Val Asp Asp Phe Gly
           100                 105                 110

Asp Phe Thr Pro Ser Leu Glu Leu Arg Lys Leu Ile Pro Ser Val Glu
       115                 120                 125

Thr Ser Gly Asp Ile Ser Thr Phe Pro Leu Val Ile Phe Gln Ile Thr
130                 135                 140

Arg Phe Lys Cys Gly Gly Val Ala Leu Gly Gly Val Phe His Thr
145                 150                 155                 160

Leu Ser Asp Gly Leu Ser Ser Ile His Phe Ile Asn Thr Trp Ser Asp
                165                 170                 175

Ile Ala Arg Gly Leu Ser Val Ala Val Pro Pro Phe Ile Asp Arg Thr
            180                 185                 190

Leu Leu Arg Ala Arg Asp Pro Pro Thr Tyr Ser Phe Glu His Val Glu
        195                 200                 205

Tyr His Pro Pro Pro Thr Leu Asn Ser Ser Lys Asn Arg Glu Ser Ser
    210                 215                 220

Thr Thr Thr Met Leu Lys Phe Ser Ser Glu Gln Leu Gly Leu Leu Lys
225                 230                 235                 240

Ser Lys Ser Lys Asn Glu Gly Ser Thr Tyr Glu Ile Leu Ala Ala His
                245                 250                 255

Ile Trp Arg Cys Thr Cys Lys Ala Arg Gly Leu Pro Glu Asp Gln Leu
            260                 265                 270

Thr Lys Leu His Val Ala Thr Asp Gly Arg Ser Arg Leu Cys Pro Pro
        275                 280                 285

Leu Pro Pro Gly Tyr Leu Gly Asn Val Val Phe Thr Ala Thr Pro Ile
    290                 295                 300

Ala Lys Ser Cys Glu Leu Gln Ser Glu Pro Leu Thr Asn Ser Val Lys
305                 310                 315                 320

Arg Ile His Asn Glu Leu Ile Lys Met Asp Asp Asn Tyr Leu Arg Ser
                325                 330                 335

Ala Leu Asp Tyr Leu Glu Leu Gln Pro Asp Leu Ser Thr Leu Ile Arg
            340                 345                 350

Gly Pro Ala Tyr Phe Ala Ser Pro Asn Leu Asn Ile Asn Ser Trp Thr
        355                 360                 365

Arg Leu Pro Val His Glu Cys Asp Phe Gly Trp Gly Arg Pro Ile His
    370                 375                 380

Met Gly Pro Ala Cys Ile Leu Tyr Glu Gly Thr Ile Tyr Ile Ile Pro
385                 390                 395                 400

Ser Pro Asn Ser Lys Asp Arg Asn Leu Arg Leu Ala Val Cys Leu Asp
                405                 410                 415

Ala Gly His Met Ser Leu Phe Glu Lys Tyr Leu Tyr Glu Leu
            420                 425                 430

<210> SEQ ID NO 25
<211> LENGTH: 5
<212> TYPE: PRT
<213> ORGANISM: Coffea canephora
<220> FEATURE:
<221> NAME/KEY: MISC_FEATURE
<222> LOCATION: (1)..(5)
<223> OTHER INFORMATION: Conserved HXXXD box found in HCT and HQT
      proteins.
<220> FEATURE:
<221> NAME/KEY: MISC_FEATURE
<222> LOCATION: (2)..(4)

<223> OTHER INFORMATION: Each X can independently be any amino acid.

<400> SEQUENCE: 25

His Xaa Xaa Xaa Asp
1               5

<210> SEQ ID NO 26
<211> LENGTH: 5
<212> TYPE: PRT
<213> ORGANISM: Coffea canephora
<220> FEATURE:
<221> NAME/KEY: MISC_FEATURE
<222> LOCATION: (1)..(5)
<223> OTHER INFORMATION: conserved sequence ("DFGWG box") found in HCT
      and HQT proteins.

<400> SEQUENCE: 26

Asp Phe Gly Trp Gly
1               5

<210> SEQ ID NO 27
<211> LENGTH: 639
<212> TYPE: DNA
<213> ORGANISM: Coffea canephora

<400> SEQUENCE: 27

```
cctgcacttc tatttatcta gaccatttgt ccgtctacac acctttcttc tccatcccag      60
ctcgtttctg acaaatccct ttcgtcaatc aacaaaactc tttacatatt ttctgctaaa    120
tctcagctta tttcatcttg tttgatcagc gtgggaagcg agaaaatgaa gataaccgtg    180
aaggaaacag caatggttcg tccagcccaa ccaacaccca caagaggct atggaactcg     240
aatttggatc ttctggtagc aagaattcat atcttgaccg tctacttcta caagcctaat    300
ggttctgcta atttctttga tacccgtgtg ctcaaagaag cattgagcaa tgttcttgtc    360
tctttctacc ccatggctgg gagattagca agagatgaag aaggaaggat tgagatcgac    420
tgtaacggtg aaggtgtact ctttgttgag gctgaatcag actcgagtgt cgatgatttt    480
ggtgattttg caccaagttt ggagctcagg aggctcatcc cgaccgtcga ttgttccggt    540
gacatttctt cttacccct cgttattttc caggtaactc gtttcaagtg tggagcagca    600
gctcttggag ctggggtgca gcacaattta tcagatggc                           639
```

<210> SEQ ID NO 28
<211> LENGTH: 1056
<212> TYPE: DNA
<213> ORGANISM: Coffea canephora
<220> FEATURE:
<221> NAME/KEY: misc_feature
<222> LOCATION: (1042)..(1042)
<223> OTHER INFORMATION: n is a, c, g, or t

<400> SEQUENCE: 28

```
ctcgtttcaa gtgtggagca gcagctcttg gagctggggt gcagcacaat ttatcagatg     60
gcgtttcatc tctgcacttc atcaatacat ggtcagacat agctcgtggc ctcaccattg    120
ctgtccctcc gttcattgac cggacactta tccatgctag ggaccctccc gtgcctgtat    180
tcgaacatgt cgaatattat ccgccccctc aactaaaatc agattcaaga attcaagaac    240
tcaaaacagg ccctagggca agtaccacag ctgtactaaa aatcacacct gaacaactta    300
gccagcttaa agctaaggcc aacaatgagg gcagcactta tgagatctta gcagcacata    360
tatggcgtac tgcatgcaaa gcacgtggcc tcaccaatga tcaatccacc aagctgtacg    420
ttgccactga tggccggtct aggctgattc ctccccctgcc tcctggctat ctaggtaatg    480
```

```
tggtcttcac tgcaactcca attgctgaat ccagtgatct tcaatcagag cccttgacca       540
attctgcaaa agaatccac aatgccttag caagaatgga taatgattac ttaagatcag        600
ccctggatta tcttgaaatt caacctgatt tgtctgcttt ggttagaggg cctcggcatt       660
ttgctagtcc taatttgaat atcaatagtt ggacaaggct tccgtttcat gatgcagact       720
ttggctgggg cagacctatt catatagggc cggcaatcat tctttatgag ggtacggtat       780
atgtattgcc aagtccaggc aaagacagga ctttatcgtt agctgtgtgc ttagatgccg       840
atcacatgcc actcttccaa aagttcctgt acgatttctg agaaattttg aaatatcaac       900
aacaatcaag cttctggaag agaatggatg gaattaccat ttttagatgg tataaatcaa       960
ggcagcctcg tgacacttgt gattggattg ggactctctt ttttgtattg gtgttttgct      1020
tagtgatttt ctcattttct tnaaaaaaaa aaaaaa                                 1056

<210> SEQ ID NO 29
<211> LENGTH: 617
<212> TYPE: DNA
<213> ORGANISM: Coffea arabica

<400> SEQUENCE: 29
ttgcctggag gaaagcagag aagcatccct ccacccaatt ttcacaagac acttttgtgg        60
tcatctttca atagccactc ttcctcatca tattccacaa aggacaaagg ttatttcatc       120
ttgtttgacc agcgtgggaa gcgagaaaat gaagataacc gtgaaggaaa cagcaatggt       180
tcgtccagcc caaccaacgc ctacaaagag gctatggaac tcgaatttgg atcttttggt       240
agcaagaatt catatcttga ccgtctactt ttacaagcct aatggttctg ctaatttctt       300 tgataccgt gtgctcaaag aagcattgag caatgttctt gtctctttct acccatggc        360 tgggagatta gcaagagatg aagaaggaag gattgagatc gactgtaacg gcgaaggtgt       420
actgtttgtc gaggctgaat cagactcaag tgtcgatgat tttggtgatt ttgcaccaag       480
tttggagctc aggaggctca ttccgaccgt cgattgttct ggtgacattt cttcttaccc       540
cctcgttatt ttccaggtaa ctcgtttcaa gtgtggagga gcagctcttg agctggggt       600 gcagcacaat ttatcag                                                      617

<210> SEQ ID NO 30
<211> LENGTH: 508
<212> TYPE: PRT
<213> ORGANISM: Arabidopsis thaliana

<400> SEQUENCE: 30

Met Ser Trp Phe Leu Ile Ala Val Ala Thr Ile Ala Ala Val Val Ser
1               5                   10                  15

Tyr Lys Leu Ile Gln Arg Leu Arg Tyr Lys Phe Pro Pro Gly Pro Ser
            20                  25                  30

Pro Lys Pro Ile Val Gly Asn Leu Tyr Asp Ile Lys Pro Val Arg Phe
        35                  40                  45

Arg Cys Tyr Tyr Glu Trp Ala Gln Ser Tyr Gly Pro Ile Ile Ser Val
    50                  55                  60

Trp Ile Gly Ser Ile Leu Asn Val Val Ser Ser Ala Glu Leu Ala
65                  70                  75                  80

Lys Glu Val Leu Lys Glu His Asp Gln Lys Leu Ala Asp Arg His Arg
                85                  90                  95

Asn Arg Ser Thr Glu Ala Phe Ser Arg Asn Gly Gln Asp Leu Ile Trp
            100                 105                 110
```

```
Ala Asp Tyr Gly Pro His Tyr Val Lys Val Arg Lys Val Cys Thr Leu
            115                 120                 125
Glu Leu Phe Thr Pro Lys Arg Leu Glu Ser Leu Arg Pro Ile Arg Glu
        130                 135                 140
Asp Glu Val Thr Ala Met Val Glu Ser Val Phe Arg Asp Cys Asn Leu
145                 150                 155                 160
Pro Glu Asn Arg Ala Lys Gly Leu Gln Leu Arg Lys Tyr Leu Gly Ala
                165                 170                 175
Val Ala Phe Asn Asn Ile Thr Arg Leu Ala Phe Gly Lys Arg Phe Met
                180                 185                 190
Asn Ala Glu Gly Val Val Asp Glu Gln Gly Leu Glu Phe Lys Ala Ile
            195                 200                 205
Val Ser Asn Gly Leu Lys Leu Gly Ala Ser Leu Ser Ile Ala Glu His
        210                 215                 220
Ile Pro Trp Leu Arg Trp Met Phe Pro Ala Asp Glu Lys Ala Phe Ala
225                 230                 235                 240
Glu His Gly Ala Arg Arg Asp Arg Leu Thr Arg Ala Ile Met Glu Glu
                245                 250                 255
His Thr Leu Ala Arg Gln Lys Ser Ser Gly Ala Lys Gln His Phe Val
                260                 265                 270
Asp Ala Leu Leu Thr Leu Lys Asp Gln Tyr Asp Leu Ser Glu Asp Thr
            275                 280                 285
Ile Ile Gly Leu Leu Trp Asp Met Ile Thr Ala Gly Met Asp Thr Thr
        290                 295                 300
Ala Ile Thr Ala Glu Trp Ala Met Ala Glu Met Ile Lys Asn Pro Arg
305                 310                 315                 320
Val Gln Gln Lys Val Gln Glu Glu Phe Asp Arg Val Val Gly Leu Asp
                325                 330                 335
Arg Ile Leu Thr Glu Ala Asp Phe Ser Arg Leu Pro Tyr Leu Gln Cys
                340                 345                 350
Val Val Lys Glu Ser Phe Arg Leu His Pro Pro Thr Pro Leu Met Leu
            355                 360                 365
Pro His Arg Ser Asn Ala Asp Val Lys Ile Gly Gly Tyr Asp Ile Pro
        370                 375                 380
Lys Gly Ser Asn Val His Val Asn Val Trp Ala Val Ala Arg Asp Pro
385                 390                 395                 400
Ala Val Trp Lys Asn Pro Phe Glu Phe Arg Pro Glu Arg Phe Leu Glu
                405                 410                 415
Glu Asp Val Asp Met Lys Gly His Asp Phe Arg Leu Leu Pro Phe Gly
                420                 425                 430
Ala Gly Arg Arg Val Cys Pro Gly Ala Gln Leu Gly Ile Asn Leu Val
            435                 440                 445
Thr Ser Met Met Ser His Leu Leu His His Phe Val Trp Thr Pro Pro
        450                 455                 460
Gln Gly Thr Lys Pro Glu Glu Ile Asp Met Ser Glu Asn Pro Gly Leu
465                 470                 475                 480
Val Thr Tyr Met Arg Thr Pro Val Gln Ala Val Ala Thr Pro Arg Leu
                485                 490                 495
Pro Ser Asp Leu Tyr Lys Arg Val Pro Tyr Asp Met
            500                 505

<210> SEQ ID NO 31
<211> LENGTH: 509
<212> TYPE: PRT
<213> ORGANISM: Ocimum basilicum
```

<400> SEQUENCE: 31

```
Met Ala Ala Leu Leu Leu Leu Leu Leu Pro Ala Ile Phe Leu
1               5                   10                  15

Leu His His Leu Tyr Tyr Arg Leu Arg Phe Arg Leu Pro Pro Gly Pro
                20                  25                  30

Arg Pro Leu Pro Val Val Gly Asn Leu Tyr Asp Val Lys Pro Val Arg
                35                  40                  45

Phe Arg Cys Phe Ala Asp Trp Ala Gln Ser Tyr Gly Pro Ile Ile Ser
            50                  55                  60

Val Trp Phe Gly Ser Thr Leu Asn Val Ile Val Ser Asn Thr Glu Leu
65                  70                  75                  80

Ala Lys Glu Val Leu Lys Glu Lys Asp Gln Gln Leu Ala Asp Arg His
                85                  90                  95

Arg Ser Arg Ser Ala Ala Lys Phe Ser Arg Asp Gly Gln Asp Leu Ile
                100                 105                 110

Trp Ala Asp Tyr Gly Pro His Tyr Val Lys Val Arg Lys Val Cys Met
            115                 120                 125

Leu Glu Leu Phe Ser Pro Lys Arg Leu Glu Ala Leu Arg Pro Ile Arg
130                 135                 140

Glu Asp Glu Val Thr Ala Met Val Glu Ser Ile Tyr His Asp Cys Thr
145                 150                 155                 160

Ala Pro Asp Asn Ala Gly Lys Ser Leu Leu Val Lys Lys Tyr Leu Gly
                165                 170                 175

Ala Val Ala Phe Asn Asn Ile Thr Arg Leu Ala Phe Gly Lys Arg Phe
            180                 185                 190

Val Asn Ser Glu Gly Ile Ile Asp Lys Gln Gly Leu Glu Phe Lys Ala
                195                 200                 205

Ile Val Ser Asn Gly Leu Lys Leu Gly Ala Ser Leu Ala Met Ala Glu
            210                 215                 220

His Ile Pro Trp Leu Arg Trp Met Phe Pro Leu Asp Glu Asp Ala Phe
225                 230                 235                 240

Ala Lys His Gly Ala Arg Arg Asp Gln Leu Thr Arg Glu Ile Met Glu
                245                 250                 255

Glu His Thr Arg Ala Arg Glu Glu Ser Gly Gly Ala Lys Gln His Phe
                260                 265                 270

Phe Asp Ala Leu Leu Thr Leu Lys Asp Lys Tyr Asp Leu Ser Glu Asp
            275                 280                 285

Thr Ile Ile Gly Leu Leu Trp Asp Met Ile Thr Ala Gly Met Asp Thr
            290                 295                 300

Thr Ala Ile Ser Val Glu Trp Ala Met Ala Glu Leu Ile Lys Asn Pro
305                 310                 315                 320

Arg Val Gln Gln Lys Ala Gln Glu Glu Leu Asp Arg Val Ile Gly Tyr
                325                 330                 335

Glu Arg Val Met Thr Glu Leu Asp Phe Ser Asn Leu Pro Tyr Leu Gln
                340                 345                 350

Cys Val Ala Lys Glu Ala Leu Arg Leu His Pro Pro Thr Pro Leu Met
            355                 360                 365

Leu Pro His Arg Ser Asn Ser Asn Val Lys Ile Gly Gly Tyr Asp Ile
            370                 375                 380

Pro Lys Gly Ser Asn Val His Val Asn Val Trp Ala Val Ala Arg Asp
385                 390                 395                 400

Pro Ala Val Trp Lys Asn Pro Ser Glu Phe Arg Pro Glu Arg Phe Leu
                405                 410                 415
```

```
Glu Glu Asp Val Asp Met Lys Gly His Asp Phe Arg Leu Leu Pro Phe
            420                 425                 430

Gly Ala Gly Arg Arg Val Cys Pro Gly Ala Gln Leu Gly Ile Asn Leu
            435                 440                 445

Val Thr Ser Met Ile Gly Leu Leu His His Phe Asn Trp Ala Pro
450                 455                 460

Pro Ser Gly Val Ser Thr Asp Glu Leu Asp Met Gly Glu Asn Pro Gly
465                 470                 475                 480

Leu Val Thr Tyr Met Arg Thr Pro Leu Glu Ala Val Pro Thr Pro Arg
            485                 490                 495

Leu Pro Ser Asp Leu Tyr Lys Arg Ile Ala Val Asp Leu
            500                 505

<210> SEQ ID NO 32
<211> LENGTH: 509
<212> TYPE: PRT
<213> ORGANISM: Lycopersicon esculentum

<400> SEQUENCE: 32

Met Ala Leu Phe Leu Ile Ile Leu Thr Ser Ile Ala Leu Ile Phe Leu
1               5                   10                  15

Ala His Lys Leu Tyr His Arg Leu Arg Phe Lys Leu Pro Pro Gly Pro
            20                  25                  30

Arg Pro Leu Pro Val Val Gly Asn Leu Tyr Asp Ile Lys Pro Val Arg
            35                  40                  45

Phe Arg Cys Phe Ala Asp Trp Ala Gln Thr Tyr Gly Pro Ile Phe Ser
50                  55                  60

Val Tyr Phe Gly Ser Gln Leu Asn Val Val Thr Thr Ala Glu Leu
65                  70                  75              80

Ala Lys Gln Val Leu Lys Glu Asn Asp Gln Asn Leu Ala Asp Arg Phe
            85                  90                  95

Arg Thr Arg Pro Ala Asn Asn Leu Ser Arg Asn Gly Met Asp Leu Ile
            100                 105                 110

Trp Ala Asp Tyr Gly Pro His Tyr Val Lys Val Arg Lys Leu Cys Asn
            115                 120                 125

Leu Glu Leu Phe Thr Pro Lys Arg Leu Glu Ser Leu Arg Pro Ile Arg
130                 135                 140

Glu Asp Glu Val Thr Ala Met Val Glu Ser Ile Phe Asn Asp Cys Thr
145                 150                 155                 160

Lys Pro Asp Asn Arg Gly Lys Ser Leu Leu Met Arg Glu Tyr Leu Gly
            165                 170                 175

Ser Val Ala Phe Asn Asn Ile Thr Arg Leu Thr Phe Gly Lys Arg Phe
            180                 185                 190

Met Asn Ala Ala Gly Glu Ile Asp Glu Gln Gly Gln Glu Phe Lys Gly
            195                 200                 205

Ile Val Ser Asn Gly Ile Lys Ile Gly Gly Lys Leu Pro Leu Ala Glu
            210                 215                 220

Tyr Val Pro Trp Leu Arg Trp Phe Phe Ser Met Glu Asn Glu Ala Leu
225                 230                 235                 240

Val Lys His Ser Glu Arg Arg Asp Arg Leu Thr Arg Ile Ile Met Asp
            245                 250                 255

Glu His Thr Leu Ala Arg Lys Gln Thr Gly Asp Thr Lys Gln His Phe
            260                 265                 270

Val Asp Ala Leu Leu Thr Leu Gln Lys Gln Tyr Asp Leu Ser Asp Asp
            275                 280                 285
```

```
Thr Val Ile Gly Leu Leu Trp Asp Met Ile Thr Ala Gly Met Asp Thr
    290                 295                 300

Thr Thr Ile Thr Val Glu Trp Ala Met Ala Glu Leu Val Arg Asn Pro
305                 310                 315                 320

Arg Val Gln Gln Lys Ala Gln Glu Glu Leu Asp Arg Val Ile Gly Ser
                325                 330                 335

Asp Arg Ile Met Ser Glu Thr Asp Phe Ser Arg Leu Pro Tyr Leu Gln
            340                 345                 350

Cys Val Ala Lys Glu Ala Leu Arg Leu His Pro Pro Thr Pro Leu Met
        355                 360                 365

Leu Pro His Lys Ala Ser Ala Gly Val Lys Ile Gly Gly Tyr Asp Ile
    370                 375                 380

Pro Lys Gly Ala Ile Val His Val Asn Val Trp Ala Val Ala Arg Asp
385                 390                 395                 400

Pro Ala Val Trp Lys Asp Pro Leu Glu Phe Arg Pro Glu Arg Phe Leu
                405                 410                 415

Glu Glu Asp Val Asp Met Lys Gly His Asp Tyr Arg Leu Leu Pro Phe
            420                 425                 430

Gly Ala Gly Arg Arg Val Cys Pro Gly Ala Gln Leu Ala Ile Asn Leu
        435                 440                 445

Val Thr Ser Met Leu Gly His Leu Leu His His Phe Thr Trp Ser Pro
    450                 455                 460

Pro Pro Gly Val Ser Pro Glu Asp Ile Asp Leu Thr Glu Asn Pro Gly
465                 470                 475                 480

Thr Val Thr Tyr Met Lys Asn Pro Ile Gln Ala Ile Pro Thr Pro Arg
                485                 490                 495

Leu Pro Ala His Leu Tyr Lys Arg Val Pro Met Asp Met
        500                 505

<210> SEQ ID NO 33
<211> LENGTH: 218
<212> TYPE: DNA
<213> ORGANISM: Coffea canephora

<400> SEQUENCE: 33
agagaacggg aaaatttaaa ataaggctta ggttgcttgg gaacaatgga aaacaaggga      60
ttgttgcaga gtagggaact ctatcagtac ctcctggaga ctagtgtcta tccacatgaa     120
ctgcagcctc tcaaggagct aagggatgtt actgcaagtc atccgtgggc cactatggca     180
accgccccag atgctggtca gttgattgcc atgctctt                             218

<210> SEQ ID NO 34
<211> LENGTH: 722
<212> TYPE: DNA
<213> ORGANISM: Coffea canephora

<400> SEQUENCE: 34
gtcatccgtg ggccactatg gcaactgccc cagatgctgg tcagttgatt gccatgctct      60
tgaaactaat aagtgccaaa aagacaatag agattggtgt ctttactgga tactccctac     120
tgcttactgc ccttacaata ccagatgatg gcaggattgt agcaattgac cagaacagag     180 atacatgatga ataggctg ccaattataa gaaaagctgc agttgagcat aagatcgact     240
tcattgagtc cgaggctctt ccagttcttg ataaactcct tgaagaaaat cttaaccatg     300
aagcctttga ctttgctttc gttgatgcgg acaaattaaa ttatctgaag taccatgaga     360
aactgttgaa attgttaaag cttggtggaa tagttgtata cgacaacaca ctttggggag     420
```

```
gatcggtggc cttgccggaa gaatctgtgg ctgaggaaat gaaagcaggc aggcatttca    480
caattgagtt caacaaattg ctagctgctg atacccgagt tcaaatatcc caggttcctc    540
tgggtgatgg gattactatt tgtaagcgtc tccactaaat cttatgctgg agtacttact    600
tggtagttgt aaattcttgt tctttatcaa catgcttgta agcatgaact tgtggacttg    660
agattcttct tttgtgttta taatgtcagc cttcagtaca agatttaaaa aaaaaaaaa     720 aa                                                                  722

<210> SEQ ID NO 35
<211> LENGTH: 349
<212> TYPE: DNA
<213> ORGANISM: Coffea arabica
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 35
aaacttcgga ttaatatcct tatatgccna nagccccacc gtcttctggg ctgaataaag     60
ctaagaggca tttctgcacg ttacaaaatc tcctgaattc atcttcagta tcatggccaa    120
ggaaggaggt tctaaagtga agacaattct ccagagtgag gccctccaga agtacatctt    180
gaatactagc catacccaa gagagcatga acaactgaag gagctaagag aagagactgc     240
caggaaatat ggtgccaggg ctattatagg tgtgccacct gatgaggggc tcttcctgtc    300
tatgtttttg aaagtaatga atgccaagaa gacactggag attggtgtt                349

<210> SEQ ID NO 36
<211> LENGTH: 934
<212> TYPE: DNA
<213> ORGANISM: Coffea arabica

<400> SEQUENCE: 36
gaggttctaa aatgaagaca attctccaga gtgaggccct ccagaagtac atcttgaata     60
ctagcacata cccaagagag catgaacaac tgaaggagct aagagaagag actgccagga    120
aatatggtgc cagggctatt ataggtgtgc cacctgatga ggggctcttc ctgtctatgt    180
ttttgaaagt aatgaatgcc aagaagacac tggagattgg tgtttttact ggctattctc    240
ttcttactac tgctcttgca cttcctgatg atggccagat agttgcaata gaccctgatc    300
aaggagcatt tgaagttggt ctgaaattca tcaagaaagc tggtgtggag aacaaaatca    360
aattcatcaa atcagatggc atttctgctc taaatgattt gttgaacaat gtgaatatgc    420
agcatttgcc agaagctccc ttcagatttt tctggaaaaa gtgcactata agtaaccac     480 tagaagctag tgaagcaaca ttcgactttg catttgtgga tgcagacaag ccaagctaca    540
tccagtacca tgaacaacta ataaagctgg tgaagattgg aggaattatc gcttacgata    600
atactctata cggtggatat gttgtcagtg aagaaattga aatgcacgaa agatccactg    660
tcaacagaaa agccatcata caattcaaca actatatagc ctcggatccg cgagttgaga    720
tctctcaggt tcctatagga gatggtgtta cattgtgtag cgcatcatc gcttagctga     780 catgatattt tacatgaatt ttattaatag tgcaactgct acggtagcat agttggatgg    840
tttgcttggt cataattcct tgatgctgtc ccaataacat caggcataag aaagatttct    900
gctctgagca aaaaaaaaaa aaaaaaaaa aaaa                                 934
```

<210> SEQ ID NO 37
<211> LENGTH: 247
<212> TYPE: PRT
<213> ORGANISM: Medicago sativa

<400> SEQUENCE: 37

```
Met Ala Thr Asn Glu Asp Gln Lys Gln Thr Glu Ser Gly Arg His Gln
1               5                   10                  15

Glu Val Gly His Lys Ser Leu Leu Gln Ser Asp Ala Leu Tyr Gln Tyr
            20                  25                  30

Ile Leu Glu Thr Ser Val Phe Pro Arg Glu His Glu Ala Met Lys Glu
        35                  40                  45

Leu Arg Glu Val Thr Ala Lys His Pro Trp Asn Ile Met Thr Thr Ser
50                  55                  60

Ala Asp Glu Gly Gln Phe Leu Ser Met Leu Lys Leu Ile Asn Ala
65                  70                  75                  80

Lys Asn Thr Met Glu Ile Gly Val Tyr Thr Gly Tyr Ser Leu Leu Ala
                85                  90                  95

Thr Ala Leu Ala Ile Pro Glu Asp Gly Lys Ile Leu Ala Met Asp Ile
            100                 105                 110

Asn Lys Glu Asn Tyr Glu Leu Gly Leu Pro Val Ile Lys Lys Ala Gly
        115                 120                 125

Val Asp His Lys Ile Asp Phe Arg Glu Gly Pro Ala Leu Pro Val Leu
    130                 135                 140

Asp Glu Met Ile Lys Asp Glu Lys Asn His Gly Ser Tyr Asp Phe Ile
145                 150                 155                 160

Phe Val Asp Ala Asp Lys Asp Asn Tyr Leu Asn Tyr His Lys Arg Leu
                165                 170                 175

Ile Asp Leu Val Lys Val Gly Gly Val Ile Gly Tyr Asp Asn Thr Leu
            180                 185                 190

Trp Asn Gly Ser Val Val Ala Pro Pro Asp Ala Pro Leu Arg Lys Tyr
        195                 200                 205

Val Arg Tyr Tyr Arg Asp Phe Val Leu Glu Leu Asn Lys Ala Leu Ala
    210                 215                 220

Val Asp Pro Arg Ile Glu Ile Cys Met Leu Pro Val Gly Asp Gly Ile
225                 230                 235                 240

Thr Ile Cys Arg Arg Ile Lys
                245
```

<210> SEQ ID NO 38
<211> LENGTH: 239
<212> TYPE: PRT
<213> ORGANISM: Nicotiana tabacum

<400> SEQUENCE: 38

```
Met Ala Thr Asn Gly Arg His Gln Glu Val Gly His Lys Ser Leu Leu
1               5                   10                  15

Gln Ser Asp Ala Leu Tyr Gln Tyr Ile Leu Glu Thr Ser Val Tyr Pro
            20                  25                  30

Arg Glu Pro Glu Pro Met Lys Glu Leu Arg Glu Ile Thr Ala Lys His
        35                  40                  45

Pro Trp Asn Leu Met Thr Thr Ser Ala Asp Glu Gly Gln Phe Leu Ser
    50                  55                  60

Met Leu Ile Lys Leu Ile Asn Ala Lys Asn Thr Met Glu Ile Gly Val
65                  70                  75                  80
```

-continued

```
Phe Thr Gly Tyr Ser Leu Leu Ala Thr Ala Met Ala Leu Pro Asp Asp
                85                  90                  95

Gly Lys Ile Leu Ala Met Asp Ile Asn Arg Glu Asn Tyr Glu Ile Gly
            100                 105                 110

Leu Pro Val Ile Glu Lys Ala Gly Leu Ala His Lys Ile Glu Phe Lys
            115                 120                 125

Glu Gly Pro Ala Leu Pro Val Leu Asp Gln Met Ile Glu Asp Gly Lys
130                 135                 140

Tyr His Gly Ser Tyr Asp Phe Ile Phe Val Asp Ala Asp Lys Asp Asn
145                 150                 155                 160

Tyr Leu Asn Tyr His Lys Arg Leu Ile Asp Leu Val Lys Ile Gly Gly
                165                 170                 175

Leu Ile Gly Tyr Asp Asn Thr Leu Trp Asn Gly Ser Val Val Ala Pro
            180                 185                 190

Pro Asp Ala Pro Leu Arg Lys Tyr Val Arg Tyr Tyr Arg Asp Phe Val
            195                 200                 205

Leu Glu Leu Asn Lys Ala Leu Ala Ala Asp Ser Arg Ile Glu Ile Cys
            210                 215                 220

Gln Leu Pro Val Gly Asp Gly Ile Thr Leu Cys Arg Arg Ile Ser
225                 230                 235
```

<210> SEQ ID NO 39
<211> LENGTH: 242
<212> TYPE: PRT
<213> ORGANISM: Vitis vinifera

<400> SEQUENCE: 39

```
Met Ala Thr Asn Gln Glu Ala Gly Arg His Gln Glu Val Gly His Lys
1               5                   10                  15

Ser Leu Leu Gln Ser Asp Ala Leu Tyr Gln Tyr Ile Leu Glu Thr Ser
            20                  25                  30

Val Tyr Pro Arg Glu Pro Glu Ser Met Lys Glu Leu Arg Glu Leu Thr
        35                  40                  45

Ala Gln His Pro Trp Asn Ile Met Thr Thr Ser Ala Asp Glu Gly Gln
50                  55                  60

Phe Leu Asn Met Leu Leu Lys Leu Ile Asn Ala Lys Asn Thr Met Glu
65                  70                  75                  80

Ile Gly Val Tyr Thr Gly Tyr Ser Leu Leu Ala Thr Ala Leu Ala Leu
                85                  90                  95

Pro Asp Asp Gly Lys Ile Leu Ala Met Asp Ile Asn Lys Glu Asn Tyr
            100                 105                 110

Glu Leu Gly Leu Pro Val Ile Gln Lys Ala Gly Val Ala His Lys Ile
            115                 120                 125

Asp Phe Lys Glu Gly Pro Ala Leu Pro Val Leu Asp Gln Met Ile Glu
        130                 135                 140

Asp Gly Lys Tyr His Gly Ser Phe Asp Phe Ile Phe Val Asp Ala Asp
145                 150                 155                 160

Lys Asp Asn Tyr Leu Asn Tyr His Lys Arg Leu Ile Asp Leu Val Lys
                165                 170                 175

Val Gly Gly Ile Ile Gly Tyr Asp Asn Thr Leu Trp Asn Gly Ser Val
            180                 185                 190

Val Ala Pro Pro Asp Ala Pro Leu Arg Lys Tyr Val Arg Tyr Tyr Arg
        195                 200                 205

Asp Phe Val Leu Glu Leu Asn Lys Ala Leu Ala Ala Asp Pro Arg Ile
    210                 215                 220
```

```
Glu Ile Cys Met Leu Pro Val Gly Asp Gly Ile Thr Leu Cys Arg Arg
225                 230                 235                 240

Leu Ser

<210> SEQ ID NO 40
<211> LENGTH: 36
<212> TYPE: DNA
<213> ORGANISM: Artificial Sequence
<220> FEATURE:
<223> OTHER INFORMATION: AAP primer
<220> FEATURE:
<221> NAME/KEY: modified_base
<222> LOCATION: (24)..(25)
<223> OTHER INFORMATION: each n = inosine
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: modified_base
<222> LOCATION: (29)..(30)
<223> OTHER INFORMATION: each n = inosine
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (34)..(35)
<223> OTHER INFORMATION: each n = inosine
<220> FEATURE:
<221> NAME/KEY: misc_feature
<222> LOCATION: (34)..(35)
<223> OTHER INFORMATION: n is a, c, g, or t

<400> SEQUENCE: 40
ggccacgcgt cgactagtac gggnngggnn gggnng                         36

<210> SEQ ID NO 41
<211> LENGTH: 20
<212> TYPE: DNA
<213> ORGANISM: Artificial Sequence
<220> FEATURE:
<223> OTHER INFORMATION: AUAP primer

<400> SEQUENCE: 41
ggccacgcgt cgactagtac                                           20

<210> SEQ ID NO 42
<211> LENGTH: 27
<212> TYPE: DNA
<213> ORGANISM: Artificial Sequence
<220> FEATURE:
<223> OTHER INFORMATION: 22m12-GSP1 primer

<400> SEQUENCE: 42
caatgaacgg agggacagca atggtga                                   27

<210> SEQ ID NO 43
<211> LENGTH: 30
<212> TYPE: DNA
<213> ORGANISM: Artificial Sequence
<220> FEATURE:
<223> OTHER INFORMATION: 22m12-GSP2 primer

<400> SEQUENCE: 43
ggccacgagc tatgtctgac catgtattga                                30

<210> SEQ ID NO 44
<211> LENGTH: 29
```

-continued

```
<212> TYPE: DNA
<213> ORGANISM: Artificial Sequence
<220> FEATURE:
<223> OTHER INFORMATION: 22w14m23-GSP1 primer

<400> SEQUENCE: 44
ccatcagact cggcctccac gaaaagcac                                          29

<210> SEQ ID NO 45
<211> LENGTH: 32
<212> TYPE: DNA
<213> ORGANISM: Artificial Sequence
<220> FEATURE:
<223> OTHER INFORMATION: 22w14m23-GSP2 primer

<400> SEQUENCE: 45
cactcaatct caatccgccc atcttcgtct ct                                      32

<210> SEQ ID NO 46
<211> LENGTH: 26
<212> TYPE: DNA
<213> ORGANISM: Artificial Sequence
<220> FEATURE:
<223> OTHER INFORMATION: 122801-GSP1 primer

<400> SEQUENCE: 46
ttgtaagggc agtaagcagt agggag                                             26

<210> SEQ ID NO 47
<211> LENGTH: 26
<212> TYPE: DNA
<213> ORGANISM: Artificial Sequence
<220> FEATURE:
<223> OTHER INFORMATION: 122801-GSP2 primer

<400> SEQUENCE: 47
aagagcatgg caatcaactg accagc                                             26

<210> SEQ ID NO 48
<211> LENGTH: 27
<212> TYPE: DNA
<213> ORGANISM: Artificial Sequence
<220> FEATURE:
<223> OTHER INFORMATION: 119560-GSP1 primer

<400> SEQUENCE: 48
aacttcaaat gctccttgat cagggtc                                            27

<210> SEQ ID NO 49
<211> LENGTH: 27
<212> TYPE: DNA
<213> ORGANISM: Artificial Sequence
<220> FEATURE:
<223> OTHER INFORMATION: 119560-GSP2 primer

<400> SEQUENCE: 49
aacaccaatc tccagtgtct tcttggc                                            27

<210> SEQ ID NO 50
<211> LENGTH: 22
<212> TYPE: DNA
<213> ORGANISM: Artificial Sequence
<220> FEATURE:
<223> OTHER INFORMATION: HCT-Fullup1 primer

<400> SEQUENCE: 50
ccatgaaaat cgaggtgaag ga                                                 22
```

<210> SEQ ID NO 51
<211> LENGTH: 19
<212> TYPE: DNA
<213> ORGANISM: Artificial Sequence
<220> FEATURE:
<223> OTHER INFORMATION: CcHCT-R1 primer

<400> SEQUENCE: 51
gaaaccacca ccgcatgaa                                         19

<210> SEQ ID NO 52
<211> LENGTH: 23
<212> TYPE: DNA
<213> ORGANISM: Artificial Sequence
<220> FEATURE:
<223> OTHER INFORMATION: HQT-Fullup2 primer

<400> SEQUENCE: 52
cttctccatc ccagctcgtt tct                                    23

<210> SEQ ID NO 53
<211> LENGTH: 22
<212> TYPE: DNA
<213> ORGANISM: Artificial Sequence
<220> FEATURE:
<223> OTHER INFORMATION: HQT-FullLow2 primer

<400> SEQUENCE: 53
gagtcccaat ccaatcacaa gt                                     22

<210> SEQ ID NO 54
<211> LENGTH: 23
<212> TYPE: DNA
<213> ORGANISM: Artificial Sequence
<220> FEATURE:
<223> OTHER INFORMATION: CCoAOMT1-FullUp

<400> SEQUENCE: 54
caccatggcc agaatggaga agg                                    23

<210> SEQ ID NO 55
<211> LENGTH: 25
<212> TYPE: DNA
<213> ORGANISM: Artificial Sequence
<220> FEATURE:
<223> OTHER INFORMATION: CCoAOMT1-FullLow primer

<400> SEQUENCE: 55
agtagggaaa ttaattagct gacgc                                  25

<210> SEQ ID NO 56
<211> LENGTH: 30
<212> TYPE: DNA
<213> ORGANISM: Artificial Sequence
<220> FEATURE:
<223> OTHER INFORMATION: CCoAOMT-L1-FullUp primer

<400> SEQUENCE: 56
caccatggaa aacaagggat tgttgcagag                             30

<210> SEQ ID NO 57
<211> LENGTH: 30
<212> TYPE: DNA
<213> ORGANISM: Artificial Sequence
<220> FEATURE:
<223> OTHER INFORMATION: CCoAOMT-L1-FullLow primer

```
<400> SEQUENCE: 57
aagtaagtac tccagcataa gatttagtgg                                    30

<210> SEQ ID NO 58
<211> LENGTH: 24
<212> TYPE: DNA
<213> ORGANISM: Artificial Sequence
<220> FEATURE:
<223> OTHER INFORMATION: CCoAOMT-L2-FullUp primer

<400> SEQUENCE: 58
caccatggcc aaggaaggag gttc                                          24

<210> SEQ ID NO 59
<211> LENGTH: 24
<212> TYPE: DNA
<213> ORGANISM: Artificial Sequence
<220> FEATURE:
<223> OTHER INFORMATION: CCoAOMT-L2-FullLow primer

<400> SEQUENCE: 59
atcatgtcag ctaagcgatg atgc                                          24

<210> SEQ ID NO 60
<211> LENGTH: 21
<212> TYPE: DNA
<213> ORGANISM: Artificial Sequence
<220> FEATURE:
<223> OTHER INFORMATION: rpl39-F1 primer

<400> SEQUENCE: 60
gaacaggccc atcccttatt g                                             21

<210> SEQ ID NO 61
<211> LENGTH: 17
<212> TYPE: DNA
<213> ORGANISM: Artificial Sequence
<220> FEATURE:
<223> OTHER INFORMATION: rpl39-R1 primer

<400> SEQUENCE: 61
cggcgcttgg cattgta                                                  17

<210> SEQ ID NO 62
<211> LENGTH: 16
<212> TYPE: DNA
<213> ORGANISM: Artificial Sequence
<220> FEATURE:
<223> OTHER INFORMATION: rpl39-MGB1 primer

<400> SEQUENCE: 62
atgcgcactg acaaca                                                   16

<210> SEQ ID NO 63
<211> LENGTH: 27
<212> TYPE: DNA
<213> ORGANISM: Artificial Sequence
<220> FEATURE:
<223> OTHER INFORMATION: CcC3H-F1 primer

<400> SEQUENCE: 63
ctcttgttac taaattttca gcttgca                                       27

<210> SEQ ID NO 64
<211> LENGTH: 24
```

```
<212> TYPE: DNA
<213> ORGANISM: Artificial Sequence
<220> FEATURE:
<223> OTHER INFORMATION: CcC3H-R1 primer

<400> SEQUENCE: 64
ggagaatcca acaagttctt caca                                          24

<210> SEQ ID NO 65
<211> LENGTH: 18
<212> TYPE: DNA
<213> ORGANISM: Artificial Sequence
<220> FEATURE:
<223> OTHER INFORMATION: CcC3H-MGB1 primer

<400> SEQUENCE: 65
agttgcttca cttccaac                                                 18

<210> SEQ ID NO 66
<211> LENGTH: 23
<212> TYPE: DNA
<213> ORGANISM: Artificial Sequence
<220> FEATURE:
<223> OTHER INFORMATION: CcHCT-F1 primer

<400> SEQUENCE: 66
gggagcacat cacatgaatt ttc                                           23

<210> SEQ ID NO 67
<211> LENGTH: 19
<212> TYPE: DNA
<213> ORGANISM: Artificial Sequence
<220> FEATURE:
<223> OTHER INFORMATION: CcHCT-R1 primer

<400> SEQUENCE: 67
gaaaccacca ccgcatgaa                                                19

<210> SEQ ID NO 68
<211> LENGTH: 14
<212> TYPE: DNA
<213> ORGANISM: Artificial Sequence
<220> FEATURE:
<223> OTHER INFORMATION: CcHCT-MGB1 primer

<400> SEQUENCE: 68
cggttccggg ccag                                                     14

<210> SEQ ID NO 69
<211> LENGTH: 19
<212> TYPE: DNA
<213> ORGANISM: Artificial Sequence
<220> FEATURE:
<223> OTHER INFORMATION: CcHQT-F1 primer

<400> SEQUENCE: 69
ttgccaagtc caggcaaag                                                19

<210> SEQ ID NO 70
<211> LENGTH: 21
<212> TYPE: DNA
<213> ORGANISM: Artificial Sequence
<220> FEATURE:
<223> OTHER INFORMATION: CcHQT-R1 primer

<400> SEQUENCE: 70
catgtgatcg gcatctaagc a                                             21
```

```
<210> SEQ ID NO 71
<211> LENGTH: 20
<212> TYPE: DNA
<213> ORGANISM: Artificial Sequence
<220> FEATURE:
<223> OTHER INFORMATION: CcHQT-MGB1 primer

<400> SEQUENCE: 71
caggacttta tcgttagctg                                            20

<210> SEQ ID NO 72
<211> LENGTH: 19
<212> TYPE: DNA
<213> ORGANISM: Artificial Sequence
<220> FEATURE:
<223> OTHER INFORMATION: CcCCoAOMT1-F1 primer

<400> SEQUENCE: 72
tgcggaaagt tgggaatca                                             19

<210> SEQ ID NO 73
<211> LENGTH: 26
<212> TYPE: DNA
<213> ORGANISM: Artificial Sequence
<220> FEATURE:
<223> OTHER INFORMATION: CcCCoAOMT1-R1 primer

<400> SEQUENCE: 73
aagaggagga agcaaaagaa gtaggt                                     26

<210> SEQ ID NO 74
<211> LENGTH: 20
<212> TYPE: DNA
<213> ORGANISM: Artificial Sequence
<220> FEATURE:
<223> OTHER INFORMATION: CcCCoAOMT1-MGB1 primer

<400> SEQUENCE: 74
tgcaaatgaa aaatagccca                                            20

<210> SEQ ID NO 75
<211> LENGTH: 22
<212> TYPE: DNA
<213> ORGANISM: Artificial Sequence
<220> FEATURE:
<223> OTHER INFORMATION: CcCCoAOMT-L1-F1 primer

<400> SEQUENCE: 75
gctagctgct gatacccgag tt                                         22

<210> SEQ ID NO 76
<211> LENGTH: 27
<212> TYPE: DNA
<213> ORGANISM: Artificial Sequence
<220> FEATURE:
<223> OTHER INFORMATION: CcCCoAOMT-L1-R1 primer

<400> SEQUENCE: 76
gacgcttaca aatagtaatc ccatcac                                    27

<210> SEQ ID NO 77
<211> LENGTH: 17
<212> TYPE: DNA
<213> ORGANISM: Artificial Sequence
<220> FEATURE:
<223> OTHER INFORMATION: CcCCoAOMT-L1-MGB1 primer
```

```
<400> SEQUENCE: 77
tatcccaggt tcctctg                                                    17

<210> SEQ ID NO 78
<211> LENGTH: 24
<212> TYPE: DNA
<213> ORGANISM: Artificial Sequence
<220> FEATURE:
<223> OTHER INFORMATION: CcCCoAOMT-L2-F1 primer

<400> SEQUENCE: 78
gttacattgt gtaggcgcat catc                                            24

<210> SEQ ID NO 79
<211> LENGTH: 24
<212> TYPE: DNA
<213> ORGANISM: Artificial Sequence
<220> FEATURE:
<223> OTHER INFORMATION: CcCCoAOMT-L2-R1 primer

<400> SEQUENCE: 79
tgctaccgta gcagttgcac tatt                                            24

<210> SEQ ID NO 80
<211> LENGTH: 20
<212> TYPE: DNA
<213> ORGANISM: Artificial Sequence
<220> FEATURE:
<223> OTHER INFORMATION: CcCCoAOMT-L2-MGB1 primer

<400> SEQUENCE: 80
tagctgacat gatattttac                                                 20

<210> SEQ ID NO 81
<211> LENGTH: 22
<212> TYPE: DNA
<213> ORGANISM: Artificial Sequence
<220> FEATURE:
<223> OTHER INFORMATION: AP1 primer

<400> SEQUENCE: 81
gtaatacgac tcactatagg gc                                              22

<210> SEQ ID NO 82
<211> LENGTH: 19
<212> TYPE: DNA
<213> ORGANISM: Artificial Sequence
<220> FEATURE:
<223> OTHER INFORMATION: AP2 primer

<400> SEQUENCE: 82
actatagggc acgcgtggt                                                  19

<210> SEQ ID NO 83
<211> LENGTH: 29
<212> TYPE: DNA
<213> ORGANISM: Artificial Sequence
<220> FEATURE:
<223> OTHER INFORMATION: HCT-GSP1 primer

<400> SEQUENCE: 83
ccatcagact cggcctccac gaaaagcac                                       29

<210> SEQ ID NO 84
<211> LENGTH: 32
```

```
<212> TYPE: DNA
<213> ORGANISM: Artificial Sequence
<220> FEATURE:
<223> OTHER INFORMATION: HCT-GSP2 primer

<400> SEQUENCE: 84
cactcaatct caatccgccc atcttcgtct ct                                   32

<210> SEQ ID NO 85
<211> LENGTH: 5
<212> TYPE: PRT
<213> ORGANISM: Coffea canephora
<220> FEATURE:
<221> NAME/KEY: HHAAD_box
<222> LOCATION: (1)..(5)
<223> OTHER INFORMATION: Conserved sequence HHAAD, one form of HXXXD box
      found in HCT and HQT proteins

<400> SEQUENCE: 85

His His Ala Ala Asp
1               5

<210> SEQ ID NO 86
<211> LENGTH: 22
<212> TYPE: DNA
<213> ORGANISM: Artificial Sequence
<220> FEATURE:
<223> OTHER INFORMATION: HQT-FullUp1 primer

<400> SEQUENCE: 86
ctggaggaaa gcagagaagc at                                              22

<210> SEQ ID NO 87
<211> LENGTH: 39
<212> TYPE: DNA
<213> ORGANISM: Artificial Sequence
<220> FEATURE:
<223> OTHER INFORMATION: 178-HCT-S primer

<400> SEQUENCE: 87
ttaattaatt cgcggatcca tgaaaatcga ggtgaagga                            39

<210> SEQ ID NO 88
<211> LENGTH: 44
<212> TYPE: DNA
<213> ORGANISM: Artificial Sequence
<220> FEATURE:
<223> OTHER INFORMATION: 178-HCT-R primer

<400> SEQUENCE: 88
tatatatact agtctagatc aaatgtcata caagaaactc tgga                      44

<210> SEQ ID NO 89
<211> LENGTH: 39
<212> TYPE: DNA
<213> ORGANISM: Artificial Sequence
<220> FEATURE:
<223> OTHER INFORMATION: 178-HQT-S primer

<400> SEQUENCE: 89
tttaaatttc gcggatccat gaagataacc gtgaaggaa                            39

<210> SEQ ID NO 90
<211> LENGTH: 39
<212> TYPE: DNA
<213> ORGANISM: Artificial Sequence
<220> FEATURE:
<223> OTHER INFORMATION: 178-HQT-R primer
```

```
<400> SEQUENCE: 90
tatatatact agtctagatc agaaatcgta caggaacct                                      39
```

POLYNUCLEOTIDES ENCODING PHENYLPROPANOID PATHWAY ENZYMES IN COFFEE

This is a U.S. National Phase of International Application No. PCT/US2006/039618, filed Oct. 10, 2006, which claims benefit of U.S. Provisional Application No. 60/724,673, filed Oct. 7, 2005, the entire contents of each of which are incorporated by reference herein.

FIELD OF THE INVENTION

The present invention relates to the field of agricultural biotechnology. In particular, the invention features polynucleotides from coffee plants that encode enzymes involved in the phenylpropanoid pathway, leading to chlorogenic acid synthesis, as well as methods for using these polynucleotides for gene regulation and manipulation of flavor, aroma and other features of coffee beans, and in the protection of the coffee plant from disease and oxidative stress.

BACKGROUND OF THE INVENTION

Various publications, including patents, published applications and scholarly articles, are cited throughout the specification. Each of these publications is incorporated by reference herein, in its entirety. Citations not fully set forth within the specification may be found at the end of the specification.

Coffee aroma and flavor are key components in consumer preference for coffee varieties and brands. Coffee's characteristic aroma and flavor stems from a complex series of chemical reactions involving flavor precursors (Maillard reactions) that occur during the roasting of the bean. Flavor precursors include chemical compounds and biomolecules present in the green coffee bean. To date, over 800 chemicals and biomolecules have been identified as contributing to coffee flavor and aroma (Flament, I. 2002 *Coffee Flavor Chemistry* J. Wiley, U.K.).

Because coffee consumers are becoming increasingly sophisticated, it is desirable to produce coffee with improved aroma and flavor in order to meet consumer preferences. Both aroma and flavor may be artificially imparted into coffee products through chemical means. See, for example, U.S. Pat. No. 4,072,761 (aroma) and U.S. Pat. No. 3,962,321 (flavor). However, to date, there is little information concerning the influence of natural coffee grain components such as polysaccharides, proteins, pigments, and lipids, on coffee aroma and flavor. One approach is to select varieties from the existing germplasm that have superior flavor characteristics. A disadvantage to this approach is that, frequently, the highest quality varieties also possess significant negative agronomics traits, such as poor yield and low resistance to diseases and environmental stresses. It is also possible to select new varieties from breeding trials in which varieties with different industrial and agronomic traits are crossed and their progeny are screened for both high quality and good agronomic performance. However, this latter approach is very time consuming, with one crossing experiment and selection over three growing seasons taking a minimum of 7-8 years. Thus, an alternative approach to enhancing coffee quality would be to use techniques of molecular biology to enhance those elements responsible for the flavor and aroma that are naturally found in the coffee bean, or to add aroma and flavor-enhancing elements that do not naturally occur in coffee beans. Genetic engineering is particularly suited to achieve these ends. For example, coffee proteins from different coffee species may be swapped. In the alternative, the expression of genes encoding naturally occurring coffee proteins that positively contribute to coffee flavor may be enhanced. Conversely, the expression of genes encoding naturally occurring coffee proteins that negatively contribute to coffee flavor may be suppressed.

Coffees from different varieties and origins exhibit significant flavor and aroma quality variations when the green grain samples are roasted and processed in the same manner. The quality differences are a manifestation of chemical and physical variations within the grain samples that result mainly from differences in growing and processing conditions, and also from differences in the genetic background of both the maternal plant and the grain. At the level of chemical composition, at least part of the flavor quality can be associated with variations in the levels of small metabolites, such as sugars, acids, phenolics, and caffeine found associated with grain from different varieties. It is accepted that there are other less well characterized flavor and flavor-precursor molecules. In addition, it is likely that structural variations within the grain also contribute to differences in coffee quality. One approach to finding new components in the coffee grain linked to coffee quality is to study the genes and proteins differentially expressed during the maturation of grain samples in different varieties that possess different quality characteristics. Similarly, genes and proteins that participate in the biosynthesis of flavor and flavor-precursor molecules may be studied.

Chlorogenic acids are examples of candidate flavor and flavor precursor molecules. Chlorogenic acids (CGA) are an important group of non-volatile compounds found in green coffee grain. CGA are composed of a family of esters between certain trans-cinnamic acids (caffeic and ferulic) and quinic acid (Clifford et al., 2000). In the coffee bean, most CGA can be categorized as belonging to one of three classifications: caffeoylquinic acids (CQA; 3-CQA, 4-CQA, and 5-CQA); dicaffeoylquinic acids (diCQA; 3,4-diCQA, 3,5-diCQA, and 4,5-diCQA); and feruloylquinic acids (FQA). In the mature green coffee grain, the levels of CGA are variable, ranging from approximately 7.88% to 14.4% on a dry matter basis (DMB) for *Coffea canephora* (robusta), and approximately 3.4% to 4.8% on a DMB for *Coffea arabica* (Ky et al., 2001). Clifford suggested that the content of CGA in *Coffea canephora* varies from 7% to 10% on a DMB whereas *Coffea arabica* varies from 5 to 7.5% on a DMB. (Clifford et al., 1985). In *C. canephora*, CQA is estimated to comprise 67% of the total CGA content, and diCQA comprise about 20%, and FQA comprise about 13%. In *C. arabica*, CQA, diCQA and FQA corresponded on average to 80, 15, and 5% of the total CGA content, respectively (Ky et al., 2001).

Much is known about the early phenylpropanoid pathway leading to the synthesis of CGA in plants. (Dixon, R. and Paiva, N. 1995 Plant Cell 7, 1085-1097; Douglas, C. J. 1996 Trends Plant Sci., 1 171-178). An overview of this biosynthetic pathway is summarized graphically in FIG. 1 (Hoffmann et al. 2004). The first step involves the conversion of phenylalanine to cinnamic acid by phenylalanine ammonia lyase (PAL). Four different PAL genes have been characterized in *Arabidopsis*, and those genes appear to fall into two different groups (Raes, J et al 2003, Plant Physiology 133, 1051-1071). The expression and activities of the different PAL isoforms represent a major branch-point between primary and secondary metabolism in plants, and as such, the different PAL isoforms are under complex regulatory control. (Dixon, R. and Paiva, N. 1995 Plant Cell 7, 1085-1097; Rohde, A., et al. 2004 Plant Cell, 16 p 2749-2771). The next enzyme in the pathway is trans cinnamate-4-hydroxylase (C4H) (accession number BAA24355; CYP73A5 *Arabidopsis thaliaina*), which converts cinnamic acid to p-Coumaric acid. To date, only one gene has been found for this P450- dependant mono-oxygenase in *Arabidopsis*, whereas in some other plants, two or more C4H genes have been found that fall into two distinct classes (Reas et al., 2003). The next step in the pathway is carried out by 4-coumarate:Co ligase (4CL). At least four 4CL genes and nine 4CL-like genes have be identified in the *Arabidopsis* genome (Raes et al. 2003). 4CL forms esters between CoA and phenolic compounds such as p-coumaric acid, caffeic acid, ferulic acid, 5-hydroxyferulic acid acid, and sinapic acid (Hu et al. 1998).

While the enzymes involved with the early part of the phenylpropanoid pathway have been known for several years, the acyl transferases necessary for the next step, hydroxycinnamoyl-CoA transferase (HCT) (tobacco) and hydroxycinnamoyl-CoA quinate: hydroxycinnamoyl transferase (HQT) (from tomato and tobacco) have only recently been purified, and their corresponding DNA sequences cloned and studied (Hoffmann et al 2003 J. Biol Chem 278, 95-103; Niggeweg et al. 2004 Nature Biotechnology, 22, 746-754). These enzymes catalyze ester formation between p-coumaroyl-CoA or caffeoyl-CoA and either shikimate or quinate to generate CGA. HCT has also been shown to catalyze the reverse reaction, i.e., CGA degradation (Hoffmann et al., 2003). Only one gene encoding an enzyme for this step, an HCT, has been identified in *Arabidopsis* (Raes, et al. 2003). The next step of the phenylpropanoid pathway, the hydroxylation of the 3 position of coumarate, has only recently been elucidated. Schoch et al. found that an *Arabidopsis* P450 protein (CYP98A3) was capable of hydroxylating the 3 position of coumarate, but only when it was esterified to either shikimate or quinate. (2001 J. Biol Chem 276, 36566-36574). Three genes encoding this enzyme, which is called p-coumarate 3-hydroxylase (C3H), have been identified in the *Arabidopsis* genome. However, Raes et al. (2003) found that only one of these genes (C3H1) is expressed in all the tissues examined, whereas the other two genes are expressed only in a limited number of tissues and at particular times during development.

The current model of the phenylpropanoid pathway (FIG. 1) suggests that the forward and reverse activities of HCT/HQT play a role in modulating lignin precursor levels, and thus influence the amounts and types of lignin being formed in plants. After the C3H mediated hydroxylation, caffeoyl-CoA can be released from either caffeoyl quinic acid or caffeoyl shikimic acid by HCT/HQT and is then subject to the activity of caffeoyl-CoA 3-0 methytransferase (CCoAOMT) resulting in the formation of feruloyl CoA (Zhang and Chinnappa 1997 J. Biosci. 22, 161-175; Zhong et al. 1998. Plant Cell 10, 2033-2046). CCoAOMT can also methylate 5-hydroxyferuloyl-CoA to sinapoyl-CoA (Zhong et al. 1998). There are seven putative CCoAOMT genes in *Arabidopsis*, and as in other plants, there appear to be two classes of CCoAOMT genes (Zhong et al. 1998; Raes et al. 2003). Three distinct CCoAOMT classes have now been characterized in tobacco (Maury et al, 1999). Class 1 CCoAOMT genes include the only characterized *Arabidopsis* CCoAOMT gene, CCoAOMT-1, and the majority of the CCoAOMT genes characterized in other plants. The remaining putative CCoAOMT genes fall into class 2 (Raes et al. 2003). *Arabidopsis* CCoAOMT-1 is the most highly expressed gene, with expression detected in all tissues examined; lower expression of *Arabidopsis* CCoAOMT-5 and CCoAOMT-7 can also be detected in all tissues, and low expression of CCoAOMT-2, -3, -4, and -6 can be detected in specific tissues (Raes et al. 2003). Due to its relatively high ubiquitous expression, it is believed that *Arabidopsis* CCoAOMT-1, and probably orthologs in other plants, play a key role in the lignification that is associated with cell development (Raes et al. 2003).

Initially, many studies of the phenylpropanoid pathway focused on understanding the overall flux of precursors for the synthesis of flavonoids, anthocyanins, the different forms of lignin, and how the pathway was regulated. However, due to the increasing evidence that diets rich in antioxidants can reduce the risk of cancer and degenerative disease by protecting against oxidative stresses (Bazzano, L. et al. 2002; Astley, S., 2003) more recent studies have evaluated intermediary metabolites of the phenylpropanoid pathway, which are present in high levels and have been found to possess high antioxidant activity (Hoffmann et al 2004, Niggeweg et al. 2004). For example, the chlorogenic acids constitute an important group of antioxidants in plant foods such as apples, pears, tomato, potato, and eggplant, as well as green and roasted coffee grain (beans). In addition to the fact that the dietary intake of CGA is best achieved by consumption of plant foods, this class of molecules also show significant bio-availability (Nardini et al. 2002, J. Agric Food Chem. 50, 57355741; Couteau, et al., 2001, J. Applied Microbiol. 90, 873-881; Clifford, M. 2004, Planta Med 70, 1103-1114.). The involvement of CGA in the reduction of oxidative stresses has been demonstrated more directly in plants. For example, Shadle et al. (2003) have demonstrated that overexpression of the enzyme PAL in tobacco, which is responsible for the first step in the biosynthesis of CGA, resulted in an approximately five fold increase in CGA content relative to wild type plants, and demonstrated resistance to the fungal pathogen *Cercospora nicotianae*. Additional evidence has been generated by Niggeweg et al. (2004), from the overproduction of HQT in the tomato using a constitutive promoter (2×35S promoter). It was demonstrated that higher levels of HQT, an enzyme directly involved in CGA synthesis, resulted in higher levels of CGA, improved resistance to oxidative stress, and increased resistance of the plant to a microbial pathogen. There is a growing realization of the potential for dietary CGA to make important contributions to the antioxidant pool in the plasma, and it is possible that one or more CGA type molecules could be transformed into new or additional metabolites possessing health promoting activities (see, e.g., Clifford 2004). Moreover, it is apparent that CGA may play a role in plant resistance to diseases. Thus, there is a need to better understand, as well as facilitate the synthesis and accumulation of these compounds in plants.

Chlorogenic acids are abundant in coffee. Despite the fact that such molecules play an important role in plant and human health, and in overall coffee flavor, aroma, and quality, few studies have analyzed the phenylpropanoid pathway of coffee, and as such, available data on CGA in coffee is limited. Campa et al. identified a partial putative CCoAOMT sequence (accession number AF534905) (Campa et al., 2003), and mapped this sequence in the coffee genome. In addition, one of the two alleles identified for this gene were found to be associated with the overall level of chlorogenic acids. Bauman et al., have isolated two partial cDNA sequences encoding coffee PAL (accession numbers AAF27655 and AAF27654), and Campa et al, have isolated two cDNA sequences encoding coffee PAL1 (accession number AAN32866) and PAL2 (accession number AAN32867). Sequence alignment of the regions that overlap in the corresponding four proteins was made with Clustal W, and these four sequences were found to be highly related, with 94 to 99.5% predicted identity at the protein level, and greater than 97.1% identity at the nucleic acid level. This level of identity suggests that these four sequences probably represent a single coffee PAL.

Chlorogenic acids are degraded progressively during coffee roasting (De Maria et al., 1995). In fact, these changes represent one of the important compositional changes occurring during this process (Bicchi et al. 1995). It has been reported than 8-10% of the CGA content is lost with every 1% loss of dry matter. (Clifford et al. 1985, 1998). During roasting, CGA are transformed into a series of volatile and non-volatile compounds (S. Homma, 2001). For example, isomerization and hydrolysis can lead to the generation of various quinic acids and quinides, as well as cinnamic acids (Homma, 2001), with the latter group being further degraded via decarboxylation into a range of phenolic compounds, including volatile compounds such as 4-vinylguaiacol, which is associated with a typical coffee aroma (Homma 2001, Farah et al., 2005; and Rizzi, G., et al., 1993 "Flavor chemistry based on the thermally-induced decarboxylation of p-hydroxycinnamic acids. In Food Flavors, Ingredients and Composition (ed. Charalambous) pp. 663-670 Elsevier Science Publishers, Amsterdam, Netherlands).

The degradation products of CGA, particularly the formation of chlorogenic acid lactones and quinic acid lactones, are associated with the perception of bitterness in brewed coffee, and an increase in acidity found in coffee after brewing has been associated with the generation of free quinic acids (Homma, 2001, Leloup et al., 1995; and Buffo et al, 2004). More recently, Muller and Hofmann have found that chlorogenic acids and their thermal degradation products act as thiol binding sites. (2005, J. Agric and Biol Chem 53, 2623-2629). Because thiol-containing compounds, such as 2-furfurylthiol and 3-methyl-2-butene-1-thiol, are important components of a coffee aroma, it has been proposed that the chlorogenic acids and related compounds react with the aroma compounds in a coffee beverage, effectively reducing the aroma of coffee after brewing. (Muller and Hofmann, 2005).

Although it is clear that the chlorogenic acids in coffee influence flavor, it is still unclear if all the chlorogenic acids have an equivalent effect. Therefore, there is a need to generate defined coffee varieties with clear differences in their CGA profiles. There are two different routes to the selection of coffee varieties with different profiles. The first is to use classical breeding and selection, and this approach can be significantly aided by the genetic information about the CGA biosynthetic pathway. Such information will allow alleles of the key genes to be identified and followed in the breeding material and progeny. The second global approach is to directly alter specific key genes involved in the synthesis of CGA. Such may be accomplished via mutagenesis and selection (TILLING), or via the generation of specific gene expression changes using gene cloning and coffee transformation. Grain from these new non-GMO, or GMO varieties, which have altered CGA profiles, can then subsequently be evaluated for their content of chlorogenic acid degradation products and flavor profiles after roasting. Those found to be superior in flavor and other characteristics can then be chosen for further studies.

Increasing chlorogenic acid content in coffee grain could lead to an increase in CGA-derived volatiles implicated in aroma during the roasting process. Thus, modulating CGA content in the coffee grain by genetically modulating the production of the proteins responsible for CGA biosynthesis is a novel means to enhance the aroma and flavor of coffee beverages and coffee products produced from such genetically engineered coffee beans. Enhanced CGA content in the coffee bean may also positively contribute to the overall health and wellness of consumers of coffee beverages and products produced from such coffee beans. In addition, modulating CGA content in the coffee plant has implications for overall health of and disease resistance in the coffee plant. For each of these reasons, there is a need to isolate polynucleotides and polypeptides of the CGA biosynthetic pathway in coffee and to develop methods of utilizing those molecules for one or more of the aforementioned purposes.

SUMMARY OF THE INVENTION

The invention described herein features genes encoding enzymes in the phenylpropanoid pathway that lead to chlorogenic acid biosynthesis in coffee plants, their encoded polypeptides, and methods for using these polynucleotides and polypeptides for gene regulation and manipulation of flavor, aroma and other features of coffee beans.

One aspect of the invention features a nucleic acid molecule isolated from coffee (*Coffea* spp.), having a coding sequence that encodes a phenylpropanoid pathway enzyme. In one embodiment, the enzyme is a hydroxycinnamoyl-CoA shikimate/quinate hydroxycinnamoyltransferase that is at least 86.9% identical to SEQ ID NO:9 or SEQ ID NO:10. In another embodiment, the enzyme is a hydroxycinnamoyl-CoA quinate hydroxycinnamoyltransferase that is at least 78.1% identical to SEQ ID NO:11 or SEQ ID NO:12. In another embodiment, the enzyme is a p-coumaroyl 3' hydroxylase that is at least 82.9% identical to SEQ ID NO:13. In another embodiment, the enzyme is a caffeoyl-CoA 3-O methytransferase that is at least 86.3% identical to SEQ ID NO:14, SEQ ID NO:15, or SEQ ID NO:16.

In certain embodiments, the nucleic acid molecule is a gene having an open reading frame that comprises the coding sequence. Alternatively, it may comprise an mRNA molecule produced by transcription of that gene, or a cDNA molecule produced by reverse transcription of the mRNA molecule. The invention also features an oligonucleotide between 8 and 100 bases in length, which is complementary to a segment of the aforementioned nucleic acid molecule.

Another aspect of the invention features a vector comprising the above-described phenylpropanoid pathway enzyme-encoding nucleic acid molecules. In certain embodiments, the vector is an expression vector selected from the group of vectors consisting of plasmid, phagemid, cosmid, baculovirus, bacmid, bacterial, yeast and viral vectors. In certain embodiments, the vector contains the coding sequence of the nucleic acid molecule operably linked to a constitutive promoter. In other embodiments, the coding sequence is operably linked to an inducible promoter. In other embodiments, the coding sequence of the nucleic acid molecule is operably linked to a tissue specific promoter, such as a seed specific promoter, preferably a coffee seed specific promoter.

According to another aspect of the invention, a host cell transformed with the aforementioned vector is provided. The host cell may be a plant, bacterial, fungal, insect or mammalian cell. In certain embodiments, the host cell is a plant cell selected from any one of coffee, tobacco, *Arabidopsis*, maize, wheat, rice, soybean barley, rye, oats, sorghum, alfalfa, clover, canola, safflower, sunflower, peanut, cacao, tomato tomatillo, potato, pepper, eggplant, sugar beet, carrot, cucumber, lettuce, pea, aster, begonia, chrysanthemum, delphinium, zinnia, and turfgrasses. The invention also features a fertile transgenic plant produced by regenerating the transformed plant cell. In a specific embodiment, the fertile transgenic plant is a *Coffea* species.

Another aspect of the invention features a method to modulate flavor or aroma of coffee beans. The method comprises modulating production of one or more phenylpropanoid pathway enzymes within coffee seeds. In some embodiments, the method comprises increasing production of the one or more phenylpropanoid pathway enzymes, e.g., by increasing expression of one or more endogenous phenylpropanoid pathway enzyme-encoding genes within the coffee seeds, or by introducing a phenylpropanoid pathway enzyme-encoding transgene into the plant. In other embodiments, the method comprises decreasing production of the one or more phenylpropanoid pathway enzymes, e.g., by introducing a nucleic acid molecule into the coffee that inhibits the expression of one or more of the phenylpropanoid pathway enzyme-encoding genes.

Other features and advantages of the invention will be understood by reference to the drawings, detailed description and examples that follow.

DETAILED DESCRIPTION OF ILLUSTRATIVE EMBODIMENTS

Figure 1:
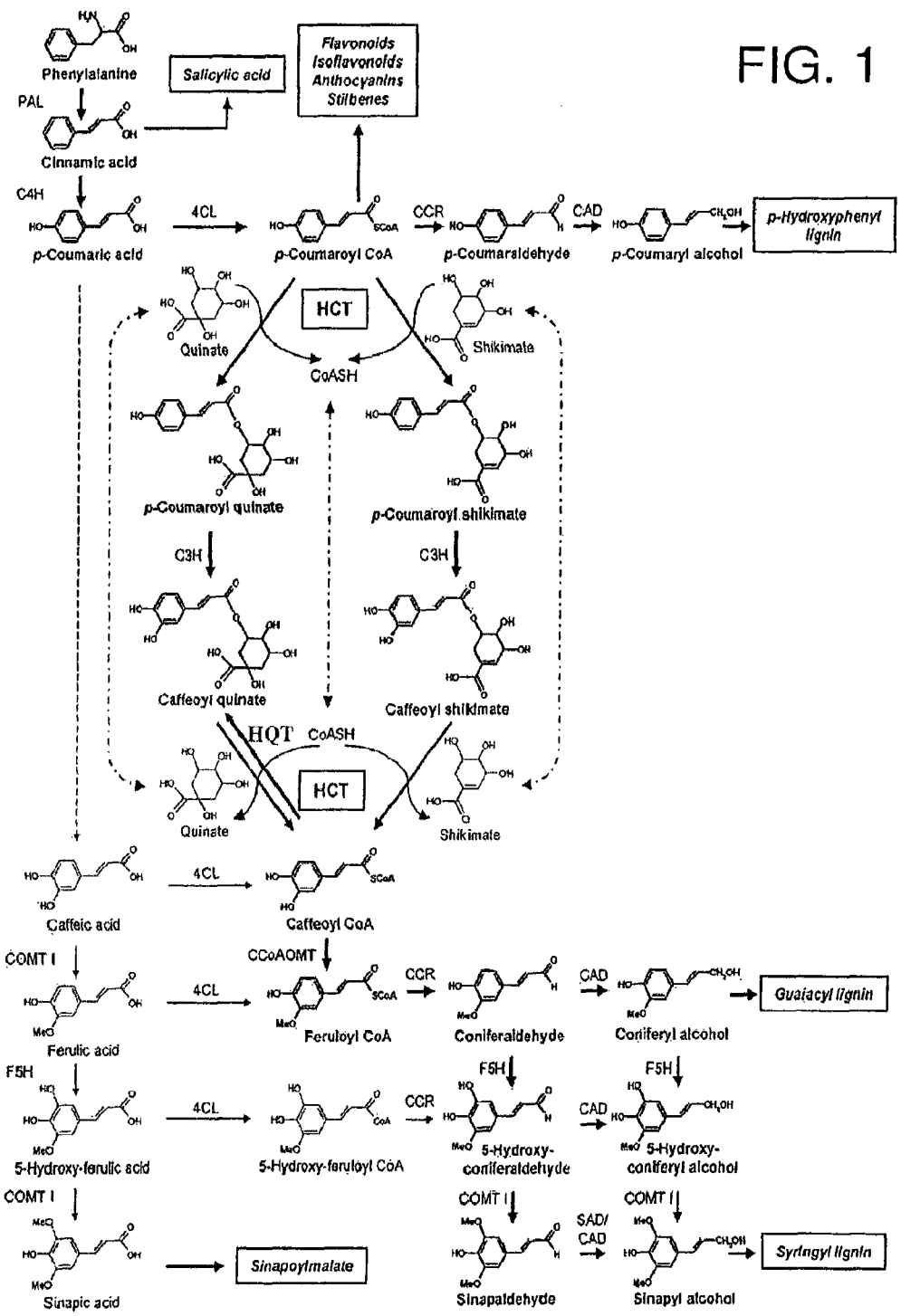
FIG. 1: Phenylpropanoid pathway. This representation of the plant phenylpropanoid pathway is a modification from Hoffman et al., 2004. PAL, Phenylalanine ammonia-lyase; C4H, Cinnamate 4-hydroxylase; 4CL, 4-hydroxycinnamoyl-CoA ligase; HCT, Hydroxycinnamoyl-Coenzyme A Shikimate/Quinate Hydroxycinnamoyltransferase; HQT, hydroxycinnamoyl-CoA quinate: hydroxycinnamoyltransferase; C3H, p-coumarate 3-hydroxylase; CCoAOMT, Caffeoyl-CoA O-methyltransferase; CAD, cinnamyl-alcohol dehydrogenase; CCR, cinnamoyl-CoA reductase; COMT I, caffeic/5-hydroxyferulic acid O-methyltransferase; F5H, ferulate 5-hydroxylase; SAD, sinapyl-alcohol dehydrogenase.

Definitions:

Various terms relating to the biological molecules and other aspects of the present invention are used throughout the specification and claims.

The term "phenylpropanoid pathway polypeptides, proteins or enzymes" refers to polypeptides that participate in the phenylpropanoid pathway, which, among other things, leads to chlorogenic acid biosynthesis in plants, and more specifically, in coffee plants. This term encompasses the specific mechanism of action of each respective protein in the pathway. The polypeptides include without limitation, phenylalanine ammonia-lyase, cinnamate 4-hydroxylase, 4-hydroxycinnamoyl-CoA ligase (also referred to as 4 coumaroyl-CoA ligase), hydroxycinnamoyl coenzyme A shikimate hydroxycinnamoyltransferase, hydroxycinnamoyl coenzyme A quinate hydroxycinnamoyltransferase p-coumarate 3-hydroxylase, caffeoyl-CoA O-methyltransferase, cinnamyl-alcohol dehydrogenase, cinnamoyl-CoA reductase, caffeic/5-hydroxyferulic acid O-methyltransferase, ferulate 5-hydroxylase, sinapyl-alcohol dehydrogenase, and the like, as exemplified herein.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide," also referred to as "nucleic acid molecule", generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., Analysis for Protein Modifications and Nonprotein Cofactors, Meth Enzymol (1990) 182:626-646 and Rattan et al, Protein Synthesis: Posttranslational Modifications and Aging, Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions or deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be nonfunctional or largely absent. Such mutations may occur in the coding and/or regulatory regions of the gene, and may be changes of individual residues, or insertions or deletions of regions of nucleic acids. These mutations may also occur in the coding and/or regulatory regions of other genes which may regulate or control a gene and/or encoded protein, so as to cause the protein to be non-functional or largely absent.

The term "substantially the same" refers to nucleic acid or amino acid sequences having sequence variations that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program. The terms "identity" or "identical" are used interchangeably with the terms "homology" or "homologous."

"Identity" and "similarity" can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the Lasergene package of the DNAstar system (Madison, Wis.) is used to align sequence fragments of genomic DNA sequences, as well as cDNA and protein sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', $F(ab')_2$ and $F_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed. The coding sequence may comprise untranslated sequences (e.g., introns or 5' or 3' untranslated regions) within translated regions, or may lack such intervening untranslated sequences (e.g., as in cDNA).

"Intron" refers to polynucleotide sequences in a nucleic acid that do not code information related to protein synthesis. Such sequences are transcribed into mRNA, but are removed before translation of the mRNA into a protein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region encodes a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," or "bean," refers to a flowering plant's unit of reproduction, capable of developing into another such plant. As used herein, especially with respect to coffee plants, the terms are used synonymously and interchangeably.

As used herein, the term "plant" includes reference to whole plants, plant organs (e.g., leaves, stems, shoots, roots), seeds, pollen, plant cells, plant cell organelles, and progeny thereof. Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

Description:

In one of its aspects, the present invention features nucleic acid molecules from coffee that encode a variety of proteins that comprise the phenylpropanoid pathway, which, among other functions, leads to chlorogenic acid biosynthesis. Representative examples of nucleic acid molecules encoding proteins that comprise the phenylpropanoid pathway were identified from databases of over 47,000 expressed sequence tags (ESTs) from several *Coffea canephora* (robusta) cDNA libraries made with RNA isolated from young leaves and from the grain and pericarp tissues of cherries harvested at different stages of development. Overlapping ESTs were identified and "clustered" into unigenes (contigs) comprising complete coding sequences. The unigene sequences were annotated by performing a BLAST search of each individual sequence against the NCBI (National Center for Biotechnology Information) non-redundant protein database.

The above-described analyzes revealed gene sequences representing several important enzymes of the phenylpropanoid pathway in the coffee plant. cDNAs representing the full open-reading frames (ORF) of several of these sequences have now been obtained. These cDNAs and their encoded proteins are referred to herein as follows:

the phenylpropanoid pathway" is used herein, it is intended to encompass all *Coffea* proteins that have the general physical, biochemical, and functional features described herein, as well as the polynucleotides that encode them.

Considered in terms of their sequences, the polynucleotides of the invention that encode proteins that comprise the phenylpropanoid pathway include allelic variants and natural mutants of SEQ ID NOs: 1-8, which are likely to be found in different varieties of *C. canephora* and *C. arabica*, and homologs of SEQ ID NOs: 1-8 likely to be found in different coffee species. Because such variants and homologs are expected to possess certain differences in nucleotide and amino acid sequence, this invention provides isolated polynucleotides encoding proteins that comprise the phenylpropanoid pathway that have at least about 50%, preferably at least about 60, 65, or 70%, more preferably at least about 71%, 72%, 73%, 74%, 75%, 76%, 77%. 78%, 79%, or 80%, even more preferably 81%, 82%, 83%, 84%, 85%, 86%, 87%, 88%, 89%, and even more preferably 90%, 91%, 92%, 93%, 94%, 95%, and most preferably 96%, 97%, 98% and 99% or more identity with any one of SEQ ID NOs:9-16, and comprise a nucleotide sequence having equivalent ranges of identity to any one of SEQ ID NOs:1-8. Because of the natural sequence variation likely to exist among proteins that comprise the phenylpropanoid pathway, and the genes encoding them in different coffee varieties and species, one skilled in the art would expect to find this level of variation, while still maintaining the unique properties of the polypeptides and polynucleotides of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

| Enzyme | cDNA | (SEQ ID NO:) | encoded protein | (SEQ ID NO:) |
|---|---|---|---|---|
| Hydroxycinnamoyl-CoA shikimate/quinate hydroxycinnamoyltransferase | CcHCT | 1 | CcHCT | 9 |
| Hydroxycinnamoyl-CoA shikimate/quinate hydroxycinnamoyltransferase | CaHCT | 2 | CaHCT | 10 |
| Hydroxycinnamoyl-CoA quinate hydroxycinnamoyltransferase | CcHQT | 3 | CcHQT | 11 |
| Hydroxycinnamoyl-CoA quinate hydroxycinnamoyltransferase | CaHQT | 4 | CaHQT | 12 |
| p-coumaroyl 3' hydroxylase | CcC3H | 5 | CcC3H | 13 |
| caffeoyl-CoA 3-O methytransferase 1 | CcCCoAOMT1 | 6 | CcCCoAOMT1 | 14 |
| caffeoyl-CoA 3-O methytransferase-like 1 | CaCCoAOMT-L1 | 7 | CaCCoAOMT-L1 | 15 |
| caffeoyl-CoA 3-O methytransferase-like 2 | CcCCoAOMT-L2 | 8 | CcCCoAOMT-L2 | 16 |

The encoded proteins have molecular masses of approximately 48.06 kDa CcHCT (SEQ ID NO:9), 48.19 kDa CaHCT (SEQ ID NO:10), 47.72 kDa CcHQT SEQ ID NO:11), 47.54 kDa CaHQT (SEQ ID NO:12), 57.9 kDa CcC3H (SEQ ID NO:13), 27.97 kDa CcCCoAOMT1 (SEQ ID NO:14), 25.71 kDa CaCCoAOM L1 (SEQ ID NO:15), and 26.3 kDa CcCCoAOMT L2 (SEQ ID NO:16). Although polynucleotides encoding proteins that comprise the phenylpropanoid pathway from *Coffea canephora* and *Coffea arabica* are described and exemplified herein, this invention is intended to encompass nucleic acids and encoded proteins from other *Coffea* species that are sufficiently similar to be used interchangeably with the exemplified *Coffea* polynucleotides and proteins for the purposes described below. Accordingly, when the term polypeptides or proteins that "comprise The gene regulatory sequences associated with genes encoding proteins that comprise the phenylpropanoid pathway are of practical utility and are considered within the scope of the present invention. Promoters and other gene regulatory sequences of genes encoding proteins that comprise the phenylpropanoid pathway from any coffee species may be obtained by the methods described below, and may be utilized in accordance with the present invention. Promoters and regulatory elements governing tissue specificity and temporal specificity of the expression of genes encoding proteins that comprise the phenylpropanoid pathway may be used to advantage, alter or modify the expression of proteins that comprise the phenylpropanoid pathway toward the goal of enhancing the flavor and aroma of coffee products produced from coffee beans comprising such modifications, among other utilities.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Sambrook et al., Molecular Cloning, Cold Spring Harbor Laboratory (1989) or Ausubel et al. (eds), Current Protocols in Molecular Biology, John Wiley & Sons (2005) are used.

Nucleic Acid Molecules, Proteins and Antibodies:

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NOs:1-8, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level sequence homology with part or all of the coding and/or regulatory regions genes encoding proteins that comprise the phenylpropanoid pathway may be identified by using hybridization and washing conditions of appropriate stringency. It will be appreciated by those skilled in the art that the aforementioned strategy, when applied to genomic sequences, will, in addition to enabling isolation coding sequences for genes encoding proteins that comprise the phenylpropanoid pathway, also enable isolation of promoters and other gene regulatory sequences associated with genes encoding proteins that comprise the phenylpropanoid pathway, even though the regulatory sequences themselves may not share sufficient homology to enable suitable hybridization.

As a typical illustration, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$Tm=81.5° C.+16.6 \log [Na+]+0.41(\% G+C)-0.63(\% \text{formamide})-600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. In one embodiment, the hybridization is at 37° C. and the final wash is at 42° C.; in another embodiment the hybridization is at 42° C. and the final wash is at 50° C.; and in yet another embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.), pBluescript (Stratagene, La Jolla, Calif.), pCR4-TOPO (Invitrogen, Carlsbad, Calif.) or pET28a+ (Novagen, Madison, Wis.), all of which can be propagated in a suitable E. coli host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting genes encoding proteins that comprise the phenylpropanoid pathway or mRNA in test samples of plant tissue, e.g., by PCR amplification, or for the positive or negative regulation of expression genes encoding proteins that comprise the phenylpropanoid pathway at or before translation of the mRNA into proteins. Methods in which oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR, including RT-PCR) and ligase chain reaction (LCR).

Polypeptides encoded by nucleic acids of the invention may be prepared in a variety of ways, according to known methods. If produced in situ the polypeptides may be purified from appropriate sources, e.g., seeds, pericarps, or other plant parts.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis., BRL, Rockville, Md. or Invitrogen, Carlsbad, Calif.

According to a preferred embodiment, larger quantities of polypeptides that comprise the phenylpropanoid pathway may be produced by expression in a suitable prokaryotic or eukaryotic system. For example, part or all of a DNA molecule, such as the cDNAs having SEQ ID NOs: 1-8, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The polypeptides that comprise the phenylpropanoid pathway produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

Polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams, *Biochemistry* 1995, 34: 1787-1797; Dobeli, *Protein Expr. Purif* 1998, 12: 404-14). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, (see e.g., Kroll, *DNA Cell. Biol.* 1993, 12: 441-53).

The polypeptides that comprise the phenylpropanoid pathway, prepared by the aforementioned methods, may be analyzed according to standard procedures.

Polypeptides that comprise the phenylpropanoid pathway purified from coffee, or produced recombinantly, may be used to generate polyclonal or monoclonal antibodies, antibody fragments or derivatives as defined herein, according to known methods. Antibodies that recognize and bind fragments of the polypeptides that comprise the phenylpropanoid pathway of the invention are also contemplated, provided that the antibodies are specific for polypeptides that comprise the phenylpropanoid pathway. For example, if analyzes of the proteins or Southern and cloning analyzes (see below) indicate that the cloned genes belongs to a multigene family, then member-specific antibodies made to synthetic peptides corresponding to nonconserved regions of the protein can be generated.

Kits comprising an antibody of the invention for any of the purposes described herein are also included within the scope of the invention. In general, such a kit includes a control antigen for which the antibody is immunospecific.

Chlorogenic acids are likely to play a role in various aspects of human health and wellness. Chlorogenic acids have been demonstrated to be powerful antioxidants in vitro (Rice-Evands, C A et al. 1996), exhibit protective effects against DNA damage in vitro (Shibata, H et al. 1999), exhibit anticarcinogenic and antimutagenic properties, and may ultimately reduce the risk of certain cancers (Olthof, M R et al. 2001; and Hollman, P C 2001), and may be protect against cardiovascular disease (Olthof, M R et al. 2001; and Hollman, P C 2001). This list of health benefits attributable to chlorogenic acids is meant to be illustrative and not exhaustive, and it is presumed that there are many other beneficial health effects attributable to chlorogenic acids presently unknown. Accordingly, the coffee polypeptides that comprise the biosynthetic pathway of chlorogenic acids described and exemplified herein are expected to find utility in a variety of food, health, and wellness applications. For example, the coffee polypeptides that comprise the biosynthetic pathway of chlorogenic acids, or their respective chlorogenic acid products, may be utilized as dietary supplements, or in various food and beverage products.

One or more of the aforementioned applications for the polypeptides that comprise the phenylpropanoid pathway may be pursued by exploiting the availability of the polynucleotides encoding polypeptides that comprise the phenylpropanoid pathway described herein to generate significant quantities of pure protein using recombinant organisms (e.g., in the yeast *Picia* pastoris or in food compatible *Lactobacilli*, or in plant cells), and then testing the proteins in new or established assays for antioxidant potential, chemoprotective or chemotherapeutic potential, potential to promote cardiovascular health, and the like. Similar testing may be carried out using the chlorogenic acids produced by these proteins according to suitable means established or developed in the art. If specific purified proteins, or chlorogenic acid products produced by such proteins are found to be particularly useful, natural versions of those proteins and their chlorogenic acid products also may be isolated from coffee grains determined to be rich in those particular polypeptides that comprise the phenylpropanoid pathway.

Vectors, Cells, Tissues and Plants:

Also featured in accordance with the present invention are vectors and kits for producing transgenic host cells that contain a polynucleotide encoding polypeptides that comprise the phenylpropanoid pathway, or an oligonucleotide, or homolog, analog or variant thereof in a sense or antisense orientation, or a reporter gene and other constructs under control of cell or tissue-specific promoters and other regulatory sequences. Suitable host cells include, but are not limited to, plant cells, bacterial cells, yeast and other fungal cells, insect cells and mammalian cells. Vectors for transforming a wide variety of these host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression, to name a few.

The present invention includes transgenic plants comprising one or more copies of a gene encoding a polypeptide that comprises the phenylpropanoid pathway, or nucleic acid sequences that inhibit the production or function of a plant's endogenous polypeptides that comprise the phenylpropanoid pathway. This is accomplished by transforming plant cells with a transgene that comprises part of all of a coding sequence for a polypeptide that comprises the phenylpropanoid pathway, or mutant, antisense or variant thereof, including RNA, controlled by either native or recombinant regulatory sequences, as described below. Transgenic plants coffee species are preferred, including, without limitation, *C. abeokutae, C. arabica, C. arnoldiana, C. aruwemiensis, C. bengalensis, C. canephora, C. congensis C. dewevrei, C. excelsa, C. eugenioides*, and *C. heterocalyx, C. kapakata, C. khasiana, C. liberica, C. moloundou, C. rasemosa, C. salvatrix, C. sessiflora, C. stenophylla, C. travencorensis, C. wightiana* and *C. zanguebariae*. Plants of any species are also included in the invention; these include, but are not limited to, tobacco, *Arabidopsis* and other "laboratory-friendly" species, cereal crops such as maize, wheat, rice, soybean barley, rye, oats, sorghum, alfalfa, clover and the like, oil-producing plants such as canola, safflower, sunflower, peanut, cacao and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turf-grasses and the like.

Transgenic plants can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993); and Methods in Plant Molecular Biology—A Laboratory Manual (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Canberra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, *Agrobacterium* "superbinary" vectors have been used successfully for the transformation of rice, maize and various other monocot species.

DNA constructs for transforming a selected plant comprise a coding sequence of interest operably linked to appropriate 5' regulatory sequences (e.g., promoters and translational regulatory sequences) and 3' regulatory sequences (e.g., terminators). In a preferred embodiment, a coding sequence encoding a polypeptide that comprises the phenylpropanoid pathway under control of its natural 5' and 3' regulatory elements is utilized. In other embodiments, coding and regulatory sequences are swapped to alter the protein content of the seed of the transformed plant for a phenotypic improvement, e.g., in flavor, aroma or other feature.

In an alternative embodiment, the coding region of the gene is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase and octopine synthase promoters. In other embodiments, a strong monocot promoter is used, for example, the maize ubiquitin promoter, the rice actin promoter or the rice tubulin promoter (Jeon et al., Plant Physiology. 123: 1005-14, 2000).

Transgenic plants with coding sequences to express polypeptides that comprise the phenylpropanoid pathway under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name only a few.

Tissue specific and development-specific promoters are also contemplated for use in the present invention. Non-limiting examples of seed-specific promoters include Cim1 (cytokinin-induced message), cZ19B1 (maize 19 kDa zein), milps (myo-inositol-1-phosphate synthase), and celA (cellulose synthase) (U.S. application Ser. No. 09/377,648), bean beta.-phaseolin, napin, beta.-conglycinin, soybean lectin, cruciferin, maize 15 kDa zein, 22 kDa zein, 27 kDa zein, g-zein, waxy, shrunken 1, shrunken 2, and globulin 1, soybean 11S legumin (Bäumlein et al., 1992), and *C. canephora* 11S seed storage protein (Marraccini et al., 1999, Plant Physiol. Biochem. 37: 273-282). See also WO 00/12733, where seed-preferred promoters from end1 and end2 genes are disclosed. Other *Coffea* seed specific promoters may also be utilized, including but not limited to the oleosin gene promoter described in commonly-owned, co-pending PCT Application No. US2006/026121, the dehydrin gene promoter described in commonly-owned, co-pending PCT Application No. US2006/026234, and the 9-cis-epoxycarotenoid dioxygenase gene promoter described in commonly-owned, co-pending PCT Application No. US2006/34402. Examples of other tissue-specific promoters include, but are not limited to: the ribulose bisphosphate carboxylase (RuBisCo) small subunit gene promoters (e.g., the coffee small subunit promoter as described by Marracini et al., 2003) or chlorophyll a/b binding protein (CAB) gene promoters for expression in photosynthetic tissue; and the root-specific glutamine synthetase gene promoters where expression in roots is desired.

The coding region is also operably linked to an appropriate 3' regulatory sequence. In embodiments where the native 3' regulatory sequence is not use, the nopaline synthetase polyadenylation region may be used. Other useful 3' regulatory regions include, but are not limited to the octopine synthase polyadenylation region.

The selected coding region, under control of appropriate regulatory elements, is operably linked to a nuclear drug resistance marker, such as kanamycin resistance. Other useful selectable marker systems include genes that confer antibiotic or herbicide resistances (e.g., resistance to hygromycin, sulfonylurea, phosphinothricin, or glyphosate) or genes conferring selective growth (e.g., phosphomannose isomerase, enabling growth of plant cells on mannose). Selectable marker genes include, without limitation, genes encoding antibiotic resistance, such as those encoding neomycin phosphotransferase II (NEO), dihydrofolate reductase (DHFR) and hygromycin phosphotransferase (HPT), as well as genes that confer resistance to herbicidal compounds, such as glyphosate-resistant EPSPS and/or glyphosate oxidoreducatase (GOX), *Bromoxynil nitrilase* (BXN) for resistance to bromoxynil, AHAS genes for resistance to imidazolinones, sulfonylurea resistance genes, and 2,4-dichlorophenoxyacetate (2,4-D) resistance genes.

In certain embodiments, promoters and other expression regulatory sequences encompassed by the present invention are operably linked to reporter genes. Reporter genes contemplated for use in the invention include, but are not limited to, genes encoding green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), lacZ (encoding α-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). As with many of the standard procedures associated with the practice of the invention, skilled artisans will be aware of additional sequences that can serve the function of a marker or reporter.

Additional sequence modifications are known in the art to enhance gene expression in a cellular host. These modifications include elimination of sequences encoding superfluous polyadenylation signals, exon-intron splice site signals, transposon-like repeats, and other such well-characterized sequences that may be deleterious to gene expression. Alternatively, if necessary, the G/C content of the coding sequence may be adjusted to levels average for a given coffee plant cell host, as calculated by reference to known genes expressed in a coffee plant cell. Also, when possible, the coding sequence is modified to avoid predicted hairpin secondary mRNA structures. Another alternative to enhance gene expression is to use 5' leader sequences. Translation leader sequences are well known in the art, and include the cis-acting derivative (omega') of the 5' leader sequence (omega) of the tobacco mosaic virus, the 5' leader sequences from brome mosaic virus, alfalfa mosaic virus, and turnip yellow mosaic virus.

Plants are transformed and thereafter screened for one or more properties, including the presence of the transgene product, the transgene-encoding mRNA, or an altered phenotype associated with expression of the transgene. It should be recognized that the amount of expression, as well as the tissue- and temporal-specific pattern of expression of the transgenes in transformed plants can vary depending on the position of their insertion into the nuclear genome. Such positional effects are well known in the art. For this reason, several nuclear transformants should be regenerated and tested for expression of the transgene.

Methods:

The nucleic acids and polypeptides of the present invention can be used in any one of a number of methods whereby the protein products can be expressed in coffee plants in order that the proteins may play a role in the protection of the plant from infection or oxidative stress, and in the enhancement of flavor and/or aroma of the coffee beverage or coffee products ultimately produced from the bean of the coffee plant expressing the protein. Similarly, the polypeptides of the invention can be used in any one of a number of methods whereby the chlorogenic acids, and other such phytochemical products synthesized by the polypeptides may play a role in the protection of the plant from infection or oxidative stress, and in the enhancement of flavor and/or aroma of the coffee beverage or coffee products ultimately produced from the bean of the coffee plant containing the chlorogenic acids.

With respect to protection of the plant from disease, and more specifically, infectious disease, it has been demonstrated that elevated production of CGA can decrease susceptibility of plants to microbial infection. For example, increasing production of CGA in the tomato plant resulted in slower progression and lower levels of infection by the bacteria *Pseudomonas syringae*. (Niggeweg R, et al. 2004). Similarly, suppressed production of CGA has been shown to increase susceptibility of tobacco plants to fungal infection. (Maher E A et al. 1994). Such studies underscore the importance of phenylpropanoids such as CGA in sustaining plant health. Thus, the ability to manipulate production of polypeptides that comprise the biosynthetic pathway for chlorogenic acids in a plant such as coffee, or even to use the polynucleotides and proteins of the invention to monitor relevant gene expression, will enable study and manipulation of the response of the coffee plant to pathogens. From this knowledge, it may be possible to generate genetically modified coffee plants with increased resistance to plant pathogens, especially coffee plant pathogens. Examples of coffee pathogens include *Hemileia vastatrix*, the etiologic agent of "Coffee Rust," and *Colletotrichum coffeanum*, the etiologic agent of "Coffee Berry Disease," and *Pseudomanas syringae* pv. *Garcae*, the etiologic agent of "Coffee Blight." Thus, one aspect of the invention features methods to decrease infectious disease susceptibility in plants, preferably coffee plants, by modulating the expression of polypeptides that comprise the phenylpropanoid pathway and the modulating the profile of chlorogenic acids in the plant.

With respect to the protection of the plant from oxidative stress, chlorogenic acids have been demonstrated to be potent antioxidants in the plants themselves. In many plant species, environmental stresses such as high light, low temperature, injury to plant tissue, nitrogen deficiency, and infection have been found to trigger CGA biosynthesis. (Grace S C et al. 2000). Chlorogenic acids have been demonstrated to have free-radical scavenging properties (Ohnishi M et al. 1994), including the scavenging of the stable green radical cation of 2,2'-azinobis-(3-ethylbenzothiazoline-6-sulphonic acid and the superoxide anion. (Grace S C et al. 2000). In plants, oxidants are formed, among other things under conditions of light stress such as excess light, or by exposure to environmental pollutants, such as ozone. Therefore, the ability to manipulate production of polypeptides that comprise the biosynthetic pathway for chlorogenic acids in a plant, or even to use the polynucleotides and proteins of the invention to monitor such gene expression, will enable study and manipulation of the response of the coffee plant to environmental stresses and the generation of oxidative species. From this knowledge, it is possible to generate genetically modified coffee plants that are better equipped for healthy growth and crop production under conditions of acute or prolonged environmental stresses. Thus, one aspect of the invention features methods to enhance free radical scavenging in plants, preferably coffee plants, by modulating the expression of polypeptides that comprise the phenylpropanoid pathway and the modulating the profile of chlorogenic acids in the plant.

With respect to flavor and aroma of roasted coffee grain, it is expected that the polypeptides that comprise the phenylpropanoid pathway exert some influence on the generation of coffee flavors via the Maillard reaction that occurs during roasting, by means of the content of the proteins themselves, or the products such as chlorogenic acids they produce. Proteins, and particularly protein degradation products (peptides and amino acids), represent an important group of flavor precursors (Spanier et al., 2004). Therefore, relatively abundant proteins such as those that comprise the phenylpropanoid pathway can be expected to make some contribution to the flavor generating reactions that occur during coffee roasting. Such a contribution may stem from the concentration of the proteins themselves in the coffee bean, or the concentration of the chlorogenic acids ultimately produced from the proteins. The ability to monitor (e.g., through marker-assisted breeding) or manipulate protein expression profiles for polypeptides that comprise the phenylpropanoid pathway is provided by the polynucleotides of the present invention, in accordance with the methods described herein.

Thus, one aspect of the present invention features methods to alter the profile of polypeptides that comprise the phenylpropanoid pathway in a plant, preferably coffee, comprising increasing or decreasing an amount or activity of one or more polypeptides that comprise the phenylpropanoid pathway in the plant. For instance, in one embodiment of the invention, a gene encoding a polypeptide that comprises the phenylpropanoid pathway under control of its own expression-controlling sequences is used to transform a plant for the purpose of increasing production of that polypeptide in the plant. Alternatively, a coding region for a polypeptide that comprises the phenylpropanoid pathway is operably linked to heterologous expression controlling regions, such as constitutive or inducible promoters.

In some embodiments, it may be desirable to have decreased production of one or more of the polypeptides that comprise the phenylpropanoid pathway in the plant. This may be accomplished several ways, for example, by screening naturally-occurring variants for decreased expression of polypeptides that comprise the phenylpropanoid pathway, or by screening naturally-occurring variants for decreased levels of the various chlorogenic acids. For instance, loss-of-function (null) mutant plants may be created or selected from populations of plant mutants currently available. It will also be appreciated by those of skill in the art that mutant plant populations may also be screened for mutants that over-express a particular polypeptide that comprises the phenylpropanoid pathway, utilizing one or more of the methods described herein. Mutant populations can be made by chemical mutagenesis, radiation mutagenesis, and transposon or T-DNA insertions, or targeting induced local lesions in genomes (TILLING, see, e.g., Henikoff et al., 2004, Plant Physiol. 135(2): 630-636; Gilchrist & Haughn, 2005, Curr. Opin. Plant Biol. 8(2): 211-215). The methods to make mutant populations are well known in the art.

The nucleic acids of the invention can be used to identify mutant polypeptides that comprise the phenylpropanoid pathway in various plant species. In species such as maize or *Arabidopsis*, where transposon insertion lines are available, oligonucleotide primers can be designed to screen lines for insertions in the genes encoding polypeptides that comprise the phenylpropanoid pathway. Through breeding, a plant line may then be developed that is heterozygous or homozygous for the interrupted gene.

A plant also may be engineered to display a phenotype similar to that seen in null mutants created by mutagenic techniques. A transgenic null mutant can be created by a expressing a mutant form of a selected polypeptide that comprises the phenylpropanoid pathway to create a "dominant negative effect." While not limiting the invention to any one mechanism, this mutant protein will compete with wild-type protein for interacting proteins or other cellular factors. Examples of this type of "dominant negative" effect are well known for both insect and vertebrate systems (Radke et al., 1997, Genetics 145: 163-171; Kolch et al., 1991, Nature 349: 426-428).

Another kind of transgenic null mutant can be created by inhibiting the translation of mRNA encoding the phenylpropanoid pathway enzymes by "post-transcriptional gene silencing." The gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95: 13959-13964). In this regard, dsRNA containing sequences that correspond to part or all of at least one intron have been found particularly effective. In one embodiment, part or all of the coding sequence antisense strand is expressed by a transgene. In another embodiment, hybridizing sense and antisense strands of part or all of the coding sequence for polypeptides that comprise the phenylpropanoid pathway are transgenically expressed.

In another embodiment, phenylpropanoid pathway enzyme-encoding genes may be silenced through the use of a variety of other post-transcriptional gene silencing (RNA silencing) techniques that are currently available for plant systems. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner (for reviews of RNA silencing in plants, see Horiguchi, 2004, Differentiation 72: 65-73; Baulcombe, 2004, Nature 431: 356-363; Herr, 2004, Biochem. Soc. Trans. 32: 946-951).

Small interfering RNAs may be chemically synthesized or transcribed and amplified in vitro, and then delivered to the cells. Delivery may be through microinjection (Tuschl T et al., 2002), chemical transfection (Agrawal N et al., 2003), electroporation or cationic liposome-mediated transfection (Brummelkamp T R et al., 2002; Elbashir S M et al., 2002), or any other means available in the art, which will be appreciated by the skilled artisan. Alternatively, the siRNA may be expressed intracellularly by inserting DNA templates for siRNA into the cells of interest, for example, by means of a plasmid, (Tuschl T et al., 2002), and may be specifically targeted to select cells. Small interfering RNAs have been successfully introduced into plants. (Klahre U et al., 2002).

A preferred method of RNA silencing in the present invention is the use of short hairpin RNAs (shRNA). A vector containing a DNA sequence encoding for a particular desired siRNA sequence is delivered into a target cell by an common means. Once in the cell, the DNA sequence is continuously transcribed into RNA molecules that loop back on themselves and form hairpin structures through intramolecular base pairing. These hairpin structures, once processed by the cell, are equivalent to siRNA molecules and are used by the cell to mediate RNA silencing of the desired protein. Various constructs of particular utility for RNA silencing in plants are described by Horiguchi, 2004, supra. Typically, such a construct comprises a promoter, a sequence of the target gene to be silenced in the "sense" orientation, a spacer, the antisense of the target gene sequence, and a terminator. If expression in most or all plant tissues is desired, strong constitutive promoters, such as the CaMV 35S promoter, may be used. Likewise, tissue-specific, developmentally-specific or temporally-specific promoters may be selected in other embodiments, as discussed hereinabove.

Yet another type of synthetic null mutant can also be created by the technique of "co-suppression" (Vaucheret et al., 1998, Plant J. 16(6): 651-659). Plant cells are transformed with a copy of the endogenous gene targeted for repression. In many cases, this results in the complete repression of the native gene as well as the transgene. In one embodiment, a gene encoding a polypeptide that comprises the phenylpropanoid pathway from the plant species of interest is isolated and used to transform cells of that same species.

Mutant or transgenic plants produced by any of the foregoing methods are also featured in accordance with the present invention. Preferably, the plants are fertile, thereby being useful for breeding purposes. Thus, mutant or plants that exhibit one or more of the aforementioned desirable phenotypes can be used for plant breeding, or directly in agricultural or horticultural applications. They will also be of utility as research tools for the further elucidation of the participation of polypeptides that comprise the phenylpropanoid pathway in flavor, aroma and other features of coffee seeds associated with pigments and photosynthesis. Plants containing one transgene or a specified mutation may also be crossed with plants containing a complementary transgene or genotype in order to produce plants with enhanced or combined phenotypes.

The present invention also features compositions and methods for producing, in a seed-preferred or seed-specific manner, any selected heterologous gene product in a plant. A coding sequence of interest is placed under control of a seed-specific coffee promoter and other appropriate regulatory sequences, to produce a seed-specific chimeric gene. The chimeric gene is introduced into a plant cell by any of the transformation methods described herein or known in the art. These chimeric genes and methods may be used to produce a variety of gene products of interest in the plant, including but not limited to: (1) detectable gene products such as GFP or GUS, as enumerated above; (2) gene products conferring an agronomic or horticultural benefit, such as those whose enzyme activities result in production of micronutrients (e.g., pro-vitamin A, also known as beta-carotene) or antioxidants (e.g., ascorbic acid, omega fatty acids, lycopene, isoprenes, terpenes); or (3) gene products for controlling pathogens or pests, such as described by Mourgues et al., (1998), TibTech 16: 203-210 or others known to be protective to plant seeds or detrimental to pathogens.

The following examples are provided to describe the invention in greater detail. The examples are intended illustrate, not to limit, the invention.

EXAMPLE 1

Plant Material for RNA Extraction

Freshly harvested roots, young leaves, stems, flowers and fruit at different stages of development were harvested from *Coffea arabica* L. cv. *Caturra* T-2308 and young leaf tissues were harvested from *Coffea canephora* var. *Robusta* BP409 grown under greenhouse conditions at Tours (25° C., 70 RH). All other tissues from *Coffea canephora* BP-409 were grown in the field in East Java, Indonesia. The development stages are defined as follows: small green fruit (SG), large green fruit (LG), yellow fruit (Y) and red fruit (R). Fresh tissues were frozen immediately in liquid nitrogen, then stored at −80° C. until used for RNA extraction.

EXAMPLE 2

Protocols for Extraction of Total RNA, Generation of cDNA, and PCR Reaction Conditions To discover the DNA sequences encoding part, or all, of the coffee enzymes HCT (hydroxycinnamoyl-CoA shikimate/quinate hydroxycinnamoyltransferase), HQT (hydroxycinnamoyl-CoA quinate hydroxycinnamoyltransferase), C3H (p-coumaroyl 3' hydroxylase), and CCoAOMT (caffeoyl-CoA-3-O-methyltransferase), which control key steps in the synthesis of chlorogenic acids (CGA) in coffee, our coffee unigene sequences with high similarity to public database protein sequences encoding HCT, HQT, C3H, and CCoAOMT from plants such as tomato, tobacco and *Arabidopsis* were discovered using the TBLASTN algorithm (Altschul et al, 1990). One of the longest cDNA of each unigene with the best hits for each protein sequence were then fully sequenced. If the protein sequence encoded in the longest EST was deemed not to contain the complete ORF, either 5' RACE PCR or primer assisted genome walking was used to isolate the missing protein coding sequences. Once the complete open reading frame (ORF) sequence for each of these coffee genes was established, gene expression analysis was carried out for the respective genes to confirm the preliminary expression information observed from the EST database.

RNA was extracted from different tissues i.e., root, stem, leaves, flowers, pericarp and grain at four different maturation stages—Small Green ("SG"), Large Green ("LG"), Yellow ("Y"), and Red ("R") from *Coffea arabica* (T2308 04-2003) and *Coffea canephora* (BP409) according to the methods of Rogers et al. (1999).

From the extracted RNA, cDNAs were prepared according to two different methods. In the first method, each specific cDNA sample was prepared from 1 µg of total RNA and 50 ng oligo $dT_{(18)}$ (Sigma Chemical Co., St. Loius, Mo.) as follows: The 1 µg total RNA sample and oligo dT were suspended in a volume of 12 ul of DEPC-treated water. This mixture was incubated at 70° C. for 10 min and then rapidly cooled on ice. Next, 4.0 µl of first strand buffer 5× (Invitrogen), 2.0 µl of 0.1M DTT (Invitrogen) and 1.0 µl of dNTP mix (10 mM each, Invitrogen) were added. These reaction mixes were incubated at 42° C. for 2 min, and then 1.0 µl of SuperScript III Rnase H-Reverse transcriptase (200 U/µl) (Invitrogen) was added. The reaction was subsequently incubated at 25° C. for 10 min. and then at 42° C. for 50 min, and followed by enzyme inactivation by heating at 70° C. for 10 min. The cDNA samples generated were then diluted ten-fold in sterile water and stored at −20° C. for use in different experiments (RT-PCR, real time RT-PCR, 5' and 3' RACE, and the isolation of full length cDNA clones).

Under the second method, specific cDNA samples were prepared from 1 µg total RNA sample and 870 ng oligo dT (Proligo) suspended in a final volume of 13 µl with DEPC-treated water. This mixture was incubated at 65° C. for 5 min to denature the nucleic acids, and the samples were then placed on ice. Next, Transcriptor RT Reaction Buffer (Roche) was added to a IX concentration, and 10.0 U of Ribonuclease Inhibitor (Sigma), 1 mM final each dNTP (Roche) and 10 U of Transcriptor Reverse Transcriptase (20 U/µl, Roche) were added. The 20 µl reaction was mixed by vortexing and then briefly centrifuged. The mixtures were incubated at 55° C. for 50 min, and then 1.0 U of RNase H (Invitrogen) was added to the reaction, followed by an incubation at 37° C. for 30 min. The samples were then stored at −20° C.

Five different 5' RACE reactions were carried out using the 5' RACE system for Rapid Amplification of cDNA Ends kit (Invitrogen) according to the manufacturer's specifications. The cDNA preparations used in this experiment were first purified to remove any unincorporated nucleotides (as they would interfere in the dC tailing reaction). Purification was carried out using S.N.A.P Columns (Invitrogen) according to the instructions given by the manufacturer. Once purified, the cDNA were recovered in 50 µL of sterilized water and then stored at −20° C. before being used for 5'RACE PCR.

The 5' RACE experiments all began with a TdT tailing of each specific S.N.A.P. purified cDNA. The poly dC tailing reaction was as follows: 25 µl reactions were set up with 5 µl of the purified cDNA, 11.5 µl DEPC treated water, 5 µl 5×TdT tailing buffer (Invitrogen), and 2.5 µl 2 mM dCTP. The reactions were then incubated at 94° C. for 3 minutes, followed by chilling on ice. 1 µl of TdT was then added, and the reaction was incubated for 10 minutes at 37° C. The reactions were terminated by heating for 10 minutes at 65° C., and were then placed on ice.

The first round of 5' RACE PCR reactions were carried out in a final 50 µl volume, as follows: 5 µl of each tailed cDNA, 5 µL 10×PCR buffer (ThermoPol buffer), 400 nM each of the Gene Specific Primer 1 (GSP1) and the Abridged Anchor Primer (AAP) (the different GSP and other primers are in Table 1), 200 µM each dNTP, and 2.5 U of Taq DNA polymerase (BioLabs). The first round PCR cycling conditions were as follows: 94° C. for 2 min; then 94° C. for 1 min, annealing temperature (noted in Table 2) for 1 min and 72° C. for 2 min and 45 cycles. An additional final step of elongation was done at 72° C. for 7 min. PCR products were then analyzed by agarose gel electrophoresis and ethidium bromide staining.

The second round of PCR reactions were performed in a final 50 µl volume, as follows: 5 µl of 1% diluted PCR (First Round) product; 5 µL 10×PCR buffer (LA buffer II Mg++ plus), 200 nM each of the GSP2 primer (Gene Specific Primer 2) and the Abridged Universal Amplification Primer (AUAP) (see primers in Table 1), 200 µM each dNTP, and 0.5 U of DNA polymerase Takara LA Taq (Cambrex Bio Science). The cycling protocol was as follows: 94° C. for 2 min; then 94° C. for 1 min, annealing temperature (noted in Table 2) for 1 min and 72° C. for 1 min 30 and 40 cycles. An additional final step of elongation was done at 72° C. for 7 min. PCR products were then analyzed by agarose gel electrophoresis and ethidium bromide staining;

TABLE 1

Primers used for 5'Race PCR experiments.

| Primer Name | Sequence | Sequence Identifier No. |
|---|---|---|
| AAP | 5'GGCCACGCGTCGACTAGTACGGGI IGGGIIGGGIIG3' | 40 |
| AUAP | 5'GGCCACGCGTCGACTAGTAC3' | 41 |
| 22m12-GSP1 | 5'CAATGAACGGAGGGACAGCAATGG TGA3' | 42 |
| 22m12-GSP2 | 5'GGCCACGAGCTATGTCTGACCATG TATTGA3' | 43 |
| 22w14m23-GSP1 | 5'CCATCAGACTCGGCCTCCACGAAA AGCAC3' | 44 |
| 22w14m23-GSP2 | 5'CACTCAATCTCAATCCGCCCATCT TCGTCTCT3' | 45 |
| 122801-GSP1 | 5'TTGTAAGGGCAGTAAGCAGTAGGG AG3' | 46 |
| 122801-GSP2 | 5'AAGAGCATGGCAATCAACTGACCA GC3' | 47 |
| 119560-GSP1 | 5'AACTTCAAATGCTCCTTGATCAGG GTC3' | 48 |
| 119560-GSP2 | 5'AACACCAATCTCCAGTGTCTTCTT GGC3' | 49 |

TABLE 2

5' Race PCR experiments Primers and Annealing Temperatures.

| Experiment | Gene-Specific Primer | Sequence Identifier No. | Annealing Temperature |
|---|---|---|---|
| CcHQT-5' RACE | | | |
| First Round RACE PCR | 22m12-GSP1 | 42 | 57° C. |
| Second Round RACE PCR | 22m12-GSP2 | 43 | 61° C. |
| CaHQT-5' RACE | | | |
| First Round RACE PCR | 22m12-GSP1 | 42 | 57° C. |
| Second Round RACE PCR | 22m12-GSP2 | 43 | 59° C. |
| CcHCT-5' RACE | | | |
| First Round RACE PCR | 22w14m23-GSP1 | 44 | 55° C. |
| Second Round RACE PCR | 22w14m23-GSP2 | 45 | 61° C. |
| CcCCoAOMT-L1-5' RACE | | | |
| First Round RACE PCR | 122801-GSP1 | 46 | 55° C. |
| Second Round RACE PCR | 122801-GSP2 | 47 | 55° C. |
| CaCCoAOMT-L2-5' RACE | | | |
| First Round RACE PCR | 119560-GSP1 | 48 | 55° C. |
| Second Round RACE PCR | 119560-GSP2 | 49 | 55° C. |

The existing cDNA sequences, and the new 5' sequences obtained from 5' RACE or primer assisted genome walking experiments, were used to design primers in the 5' and 3' UTR sequences to amplify the target cDNA sequence which contains the complete ORF sequences of CcHCT, CaHCT, CcHQT, CaHQT, CaCCoAOMT-L1, and CcCCoAOMT-L2. All of the cDNA used to isolate these complete ORF DNA sequences were prepared using the first method of cDNA synthesis described above. The two gene specific primers were designed in the region upstream of the ATG start codon and in the 3' UTR for each gene and these are given in Table 3. The specific cDNA and annealing temperatures used for the different PCR reactions are given in Table 4.

For CcHCT (pML1) (SEQ ID NO:1), CaHCT (pML5) (SEQ ID NO:2), CcHQT (pML2) (SEQ ID NO:3), CaHQT (pML3) (SEQ ID NO:4) and CcCCoAOMT-L2 (pNT4) (SEQ ID NO:8), the PCR reactions were performed in 50 µl reactions as follows: 5 µl of cDNA (Table 4), 5 µl 10×PCR buffer (La PCR Buffer II $Mg^{++}$ plus), 800 µM of the each gene specific primer, 200 µM each dNTP, and 0.5 U of DNA polymerase Takara LA Taq (Cambrex Bio Science). After denaturing at 94° C. for 2 min, the amplification consisted of 35 cycles (except for CcCCoAOMT-L2 (SEQ ID NO:8) where the amplification was for 40 cycles) of 1 min at 94° C., 1 min at annealing temperature (Table 4), and elongation for 2 min at 72° C. An additional final step of elongation was done at 72° C. for 7 min. PCR products were then analyzed by agarose gel electrophoresis and ethidium bromide staining. Fragments of the expected size were then cloned in pCR4-TOPO using TOPO TA Cloning Kit for Sequencing (Invitrogen) according to the instructions given by the manufacturer. The inserts of the plasmids generated were then sequenced entirely.

For CaCCoAOMT-L1 (pNT8) (SEQ ID NO:7), the PCR reaction was performed in 50 µl reactions as follows: 5 µL of cDNA (Table 4), 5 µl 10×PCR buffer (Cloned Pfu Reaction Buffer), 400 nM of the each gene specific primer, 200 µM of each dNTP, and 1.25 U of Pfu Turbo DNA polymerase. After denaturing at 94° C. for 2 min, the amplification consisted of 40 cycles of 1 min at 94° C., 1 min at 55° C. and 2 min at 72° C. An additional final step of elongation was done at 72° C. for 7 min. PCR product was then analyzed by agarose gel electrophoresis and ethidium bromide staining. The fragment of the expected size was then cloned in a 5' to 3' orientation in pENTR/D-TOPO according to the instructions given by the manufacturer (pENTR Directional TOPO Cloning kit, Invitrogen). The insert of the plasmid generated (pNT8) was then sequenced entirely.

TABLE 3

Primers used for amplification of CcHQT (pML2), CaHQT (pML3), CcHCT (pML1), CaHCT (pML5), CcCCoAOMT1 (pNT15), CaCCoAOMT-L1 (pNT8), CcCCoAOMT-L2 (pNT4), and CcCCoAOMT-L2 (pNT10) cDNA.

| Primers | Sequences | Sequence Identifier No. |
|---|---|---|
| HCT-FULLUP1 | 5'CCATGAAAATCGAGGTGAA GGA3' | 50 |
| CCHCT-R1 | 5'GAAACCACCACCGCATGA A3' | 51 |
| HQT-FULLUP2 | 5'CTTCTCCATCCCAGCTCGT TTCT3' | 52 |
| HQT-FULLLOW2 | 5'GAGTCCCAATCCAATGACA AGT3' | 53 |
| CCoAOMT1-FullUp | 5'CACCATGGCCAGAATGGAG AAGG3' | 54 |
| CCoAOMT1-FullLow | 5'AGTAGGGAAATTAATTAGC TGACGC3' | 55 |
| CCoAOMT-L1-FullUp | 5'CACCATGGAAAACAAGGGA TTGTTGCAGAG3' | 56 |
| CCoAOMT-L1-FullLow | 5'AAGTAAGTAGTCCAGCATA AGATTTAGTGG3' | 57 |
| CCoAOMT-L2-FullUp | 5'CACCATGGCCAAGGAAGGA GGTTC3' | 58 |
| CCoAOMT-L2-FullLow | 5'ATCATGTCAGCTAAGCGAT GATGC3' | 59 |

TABLE 4

ORF Isolation Annealing Temperatures.

| Gene | cDNA and (Tissue) | Gene-Specific Primers | Sequence Identifier Nos.: | Annealing Temp. |
|---|---|---|---|---|
| CcHCT | BP409 (Yellow Grain) | HCT-FullUp1/ CcHCT-R1 | 50/51 | 54° C. |
| CaHCT | T2308 (Yellow Grain) | HCT-FullUp1/ CcHCT-R1 | 50/51 | 56° C. |
| CcHQT | BP409 (Sm. Green Pericarp) | HQT-FullUp2/ HQT-FullLow2 | 52/53 | 59° C. |
| CaHQT | T2308 (Flower) | HQT-FullUp2/ HQT-FullLow2 | 52/53 | 55° C. |
| CaCCoAOMT-L1 (pNT8) | T2308 (Yellow Grain) | CCoAOMT-L1-FullUp/ CCoAOMT-L1-FullLow | 56/57 | 55° C. |
| CcCCoAOMT-L2 (pNT4) | BP409 (Yellow Grain) | CCoAOMT-L2-FullUp/ CCoAOMT-L2-FullLow | 56/57 | 55° C. | cDNAs subcloned into plasmids were sequenced according to the following protocol. Plasmid DNA was purified from the host using Qiagen kits according to the instructions given by the manufacturer. Prepared recombinant plasmid DNA and PCR products were sequenced by GATC Biotech AG (Konstanz, Germany) by the Sanger et al. dideoxy termination method. The unique PCR fragments produced from the 5' RACE and genome walking experiments were either sequenced without purification and cloning with the specific primers used for their amplification, or sequenced after cloning. Computer analysis were performed using the Laser Gene software package (DNASTAR). Sequence homologies were verified against GenBank databases using the BLAST programs. (Altschul et al. 1990).

Real time RT-PCR was carried out according to the following protocol. cDNA prepared by the first method described above was amplified using TaqMan-PCR kits as recommended by the manufacturer (Applied Biosystems, Perkin-Elmer), and as described previously by Privat et al., 2004. The TaqMan buffer contains AmpErase® UNG (Uracil-N-glycosylase), which is active during the first 2 min at 50° C. and is then inactivated at 95° C. at the start of the PCR cycling.

Q-PCR primers and TaqMan probes used were designed using the PRIMER EXPRESS software (Applied Biosystems) and are listed in Table 5. Quantification was carried out using the method of relative quantification, with the constitutively expressed ribosomal protein rpl39 as the baseline reference. In order to use the method of relative quantification, it was necessary to show that the amplification efficiency for the candidate cDNA sequences was roughly equivalent to the amplification efficiency of the reference sequence (rpl39 cDNA sequence) using the defined primers and probes. To determine this relative equivalence, plasmid DNA containing the appropriate cDNA sequences were diluted 1/1000, 1/10,000, 1/100,000, and 1/1,000,000 fold, and using the Q-PCR conditions described above; the slope of the curve Ct=f(Log quantity of DNA) was calculated for each plasmid/primer/TaqMan probe set. Plasmid/primer/TaqMan probe sets giving curves with slopes close to 3.32, which represents an efficiency of 100%, are considered acceptable. The plasmid/primer/TaqMan probe sets presented in Table 5 all gave acceptable values for Ct=f(Log quantity of DNA). All MGB Probes were labelled at the 5' end with the fluorescent reporter dye 6-carboxyfluorescein (FAM) and at the 3' with quencher dye 6-carboxy-tetramethyl-rhodamine (TAMRA), except RPL39 probe which was labelled at the 5' end with the fluorescent reporter dye VIC and at the 3' end with quencher TAMRA.

TABLE 5

Primers and TaqMan probes used for Q-RT-PCR experiments.

| Primers and Probes | Sequences | Sequence Identifier No.: |
|---|---|---|
| Rpl39-F1 | 5'GAACAGGCCCATCCCTTATTG3' | 60 |
| Rpl39-R1 | 5'CGGCGCTTGGCATTGTA3' | 61 |
| Rpl39-MGB1 | 5'ATGCGCACTGACAACA3' | 62 |
| CcC3H-F1 | 5'CTCTTGTTACTAAATTTTCAGCTTGCA3' | 63 |
| CcC3H-R1 | 5'GGAGAATCCAACAAGTTCTTCACA3' | 64 |
| CcC3H-MGB1 | 5'AGTTGCTTCACTTCCAAC3' | 65 |
| CcHCT-F1 | 5'GGGAGCACATCACATGAATTTTC3' | 66 |
| CcHCT-R1 | 5'GAAACCACCACCGCATGAA3' | 67 |
| CcHCT-MGB1 | 5'CGGTTCCGGGCCAG3' | 68 |
| CcHQT-F1 | 5'TTGCCAAGTCCAGGCAAAG3' | 69 |
| CcHQT-R1 | 5'CATGTGATCGGCATCTAAGCA3' | 70 |
| CcHQT-MGB1 | 5'CAGGACTTTATCGTTAGCTG3' | 71 |
| CcCCoAOMT1-F1 | 5'TGCGGAAAGTTGGGAATCA3' | 72 |
| CcCCoAOMT1-R1 | 5'AAGAGGAGGAAGCAAAAGAAGTAGGT3' | 73 |
| CcCCoAOMT1-MGB1 | 5'TGCAAATGAAAAATAGCCCA3' | 74 |
| CcCCoAOMT-L1-F1 | 5'GCTAGCTGCTGATACCCGAGTT3' | 75 |

TABLE 5-continued

Primers and TaqMan probes used for Q-RT-PCR experiments.

| Primers and Probes | Sequences | Sequence Identifier No.: |
|---|---|---|
| CcCCoAOMT-L1-R1 | 5'GACGCTTACAAATAGTAATCCCATCAC3' | 76 |
| CcCCoAOMT-L1-MGB1 | 5'TATCCCAGGTTCCTCTG3' | 77 |
| CcCCoAOMT-L2-F1 | 5'GTTACATTGTGTAGGCGCATCATC3' | 78 |
| CcCCoAOMT-L2-R1 | 5'TGCTACCGTAGCAGTTGCACTATT3' | 79 |
| CcCCoAOMT-L2-MGB1 | 5'TAGCTGACATGATATTTTAC3' | 80 |

EXAMPLE 3

Isolation and Characterization of a *Coffea canephora* cDNA Clone Encoding Hydroxycinnamoyl-CoA Shikimate/Quinate Hydroxycinnamoyltransferase (CcHCT)

To find a cDNA encoding the coffee HCT, the *Nicotiana tabacum* HCT protein sequence (accession number CAD47830 (SEQ ID NO:20)); Hoffmann et al., 2003) served as the query sequence for a BLAST search against the "unigene" set 5 using the tblastn algorithm. The best hit obtained was unigene #123197 (e value=e−150), although a second coffee unigene (#125212) was also found to be highly related to the *N. tabacum* HCT sequence (e value=e−108). Alignment of the in silico DNA and protein sequences of the unigenes #123197 and #125212 indicated that although they were potentially related, these two unigene sequences encoded different coffee genes.

Figure 2A:
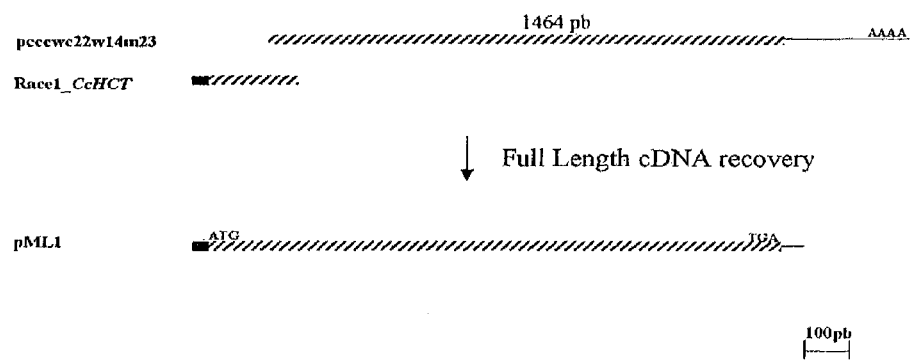
FIG. 2. Isolation and characterization of the complete ORF for CcHCT from *Coffea canephora*. A) Isolation of a cDNA containing the complete ORF of HCT from *C. canephora*. Two cDNA clones were obtained covering the complete ORF of CcHCT, the 5' RACE product (Race1_CcHCT) (SEQ ID NO:17) containing the 5' end of the *C. canephora* HCT and a partial cDNA clone pcccwc22w14m23 (SEQ ID NO:18) containing the remaining 3' end of this gene (see methods in examples). These sequences were used to design the new primers to PCR amplify a 1388 bp fragment (CcHCT in pML1) (SEQ ID NO:1) from *C. canephora* BP409 cDNA (grain, yellow stage). The 5' untranslated region is shown as a thick black bar, the ORF region is shown as a hatched bar, and the translation initiation start (ATG) and stop (TGA) codons are indicated. The 3' untranslated region is shown in thin black line. B) The insert sequence of pML1 (SEQ ID NO:1) was aligned with the cDNA sequences pcccwc22w14m23 (SEQ ID NO:18) and Race1_CcHCT (SEQ ID NO:17). The alignment was done using the CLUSTAL W program (Lasergene package, DNASTAR) and manually optimized. Nucleic acids marked in gray match the pML1 (CcHCT) insert sequence (SEQ ID NO:1).

A cDNA representing the 5' end of unigene #123197 (pcccwc22w14m23) (SEQ ID NO:18), and thus encoding the longest coffee cDNA in the database related to the tobacco HCT, was isolated and sequenced. The insert of pcccwc22w14m23 (SEQ ID NO:18) was found to be 1465 bp long, and to encode a partial ORF sequence of 389 amino acids. Because the full length tobacco protein was 435 amino acids long, it was assumed that this coffee HCT cDNA was lacking approximately 150 base pairs (i.e., the full length coffee HCT cDNA would be expected to encode another approximately 46 amino acids). Based on the significant part of the coffee HCT sequence encoded by pcccwc22w14 m23 (SEQ ID NO:18), specific primers for use in the well-established technique of 5' RACE PCR were devised to isolate the 5' end of the corresponding gene sequence. This experiment, using cDNA made by the second Method described above in Example 2 from RNA of *C. canephora* (BP409) grain at the Red developmental stage, and using the gene specific primers 22w14m23-GSP1 (SEQ ID NO:44) in first round PCR and 22w14m23-GSP2 (SEQ ID NO:45) in second round PCR, produced an approximately 300 base pair PCR fragment (length estimated in agarose gel) that was directly sequenced with gene specific primer 22w14m23-GSP2 (SEQ ID NO:45). The resulting sequence (Race1_CcHCT) (SEQ ID NO:17) was 209 bp long and overlapped the 5' end of the cDNA clone pcccwc22w14m23 (SEQ ID NO:18) (FIG. 2a: 60 bp of overlapping sequence).

Figure 2B:
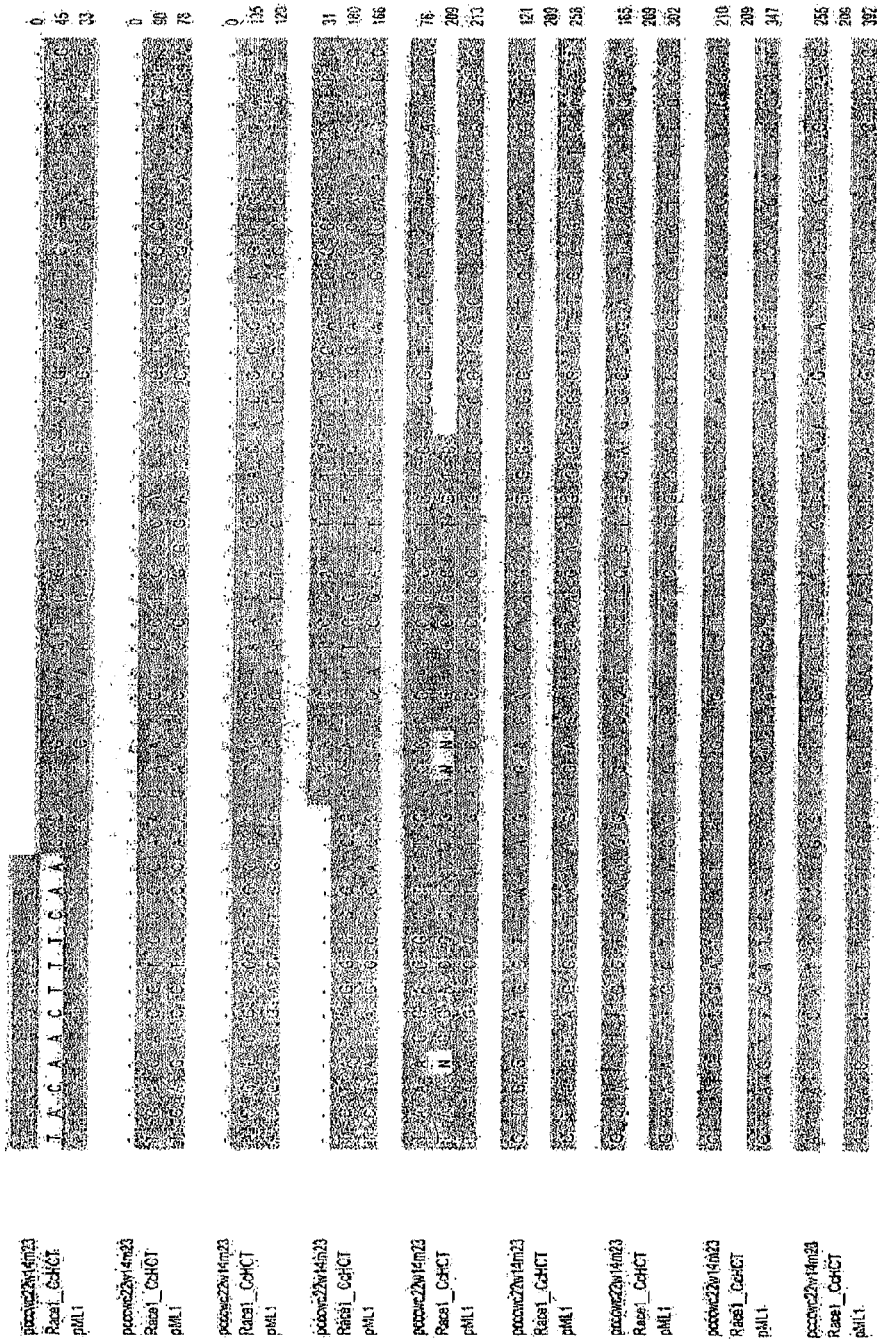
Figure 4:
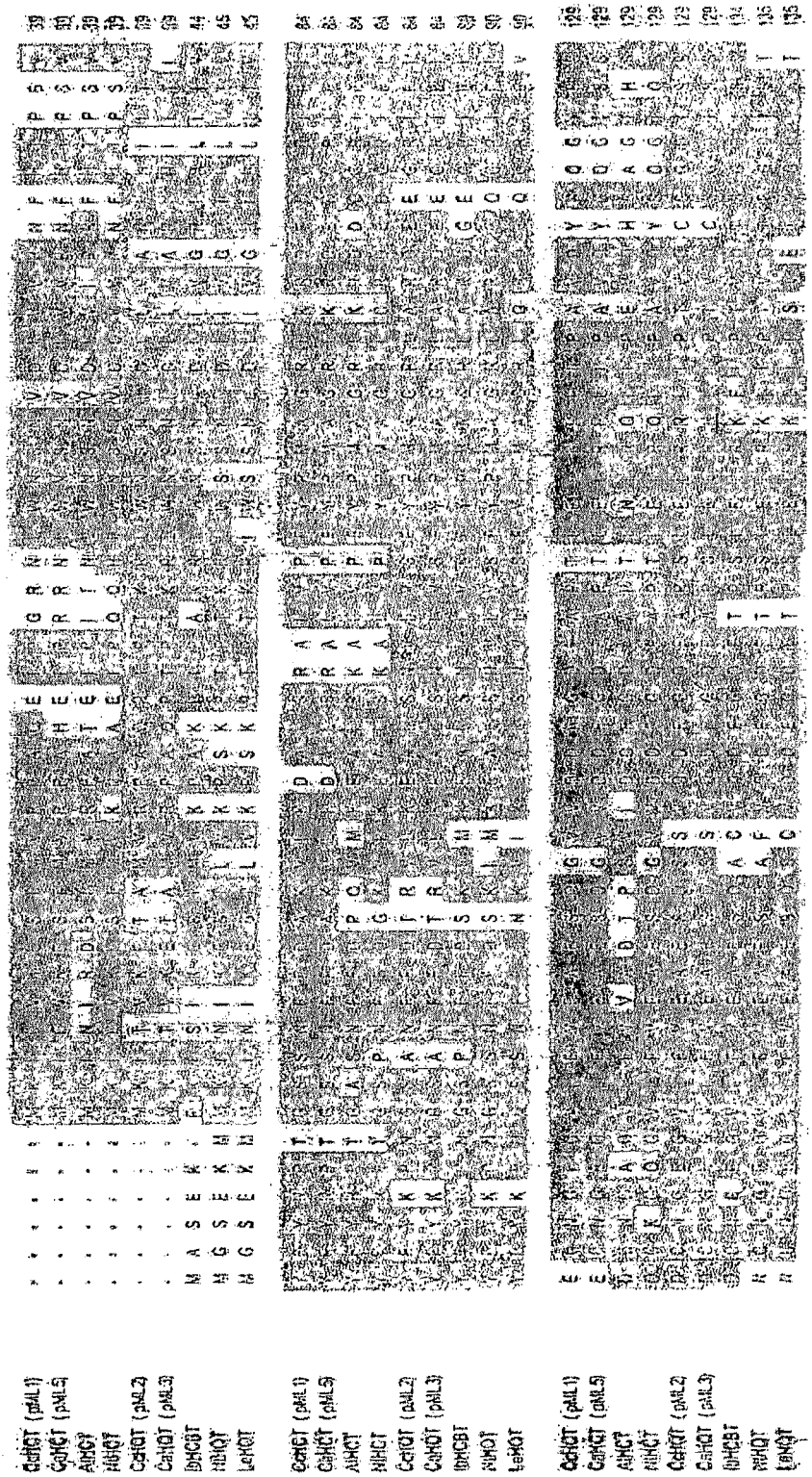
FIG. 4. Protein sequence alignment of CcHCT, CaHCT, CcHQT and CaHQT with other plant HCT and HQT protein sequences. The alignment of protein encoding sequences of CcHCT (SEQ ID NO:9), CaHCT (SEQ ID NO:10), CcHQT (SEQ ID NO:11) and CcHQT (SEQ ID NO:12) genes with other HCT and HQT proteins available in the NCBI database was done using the CLUSTAL W (Lasergene package, DNASTAR). Amino acids marked in gray denote the most frequently found residues. Gene names are listed, with accession numbers given in parentheses. NtHCT (*Nicotiana tabacum*, CAD47830 (SEQ ID NO:20)), AtHCT (*Arabidpsis thaliana*, NP_199704 (SEQ ID NO:21)), IbHCBT (*Ipomea batatas*, BAA87043.1 (SEQ ID NO:22)), NtHQT (*Nicotiana tabacum*, CAE46932.1 (SEQ ID NO:23)), and LeHQT (*Lycopesicon esculentum*, CAE46933.1 (SEQ ID NO:24)). The green and blue boxes indicate conserved amino acids residues, HXXXD (SEQ ID NO:25) and DFGWG (SEQ ID NO:26) respectively. The circled X at position 272 in the pML3 protein sequence represents a stop codon encoded by the pML3 insert sequence. But, as determined in Example 6, this stop codon was inserted during the PCR step as it has been shown that the genomic sequence encodes a Q at this position.
Figure 4:
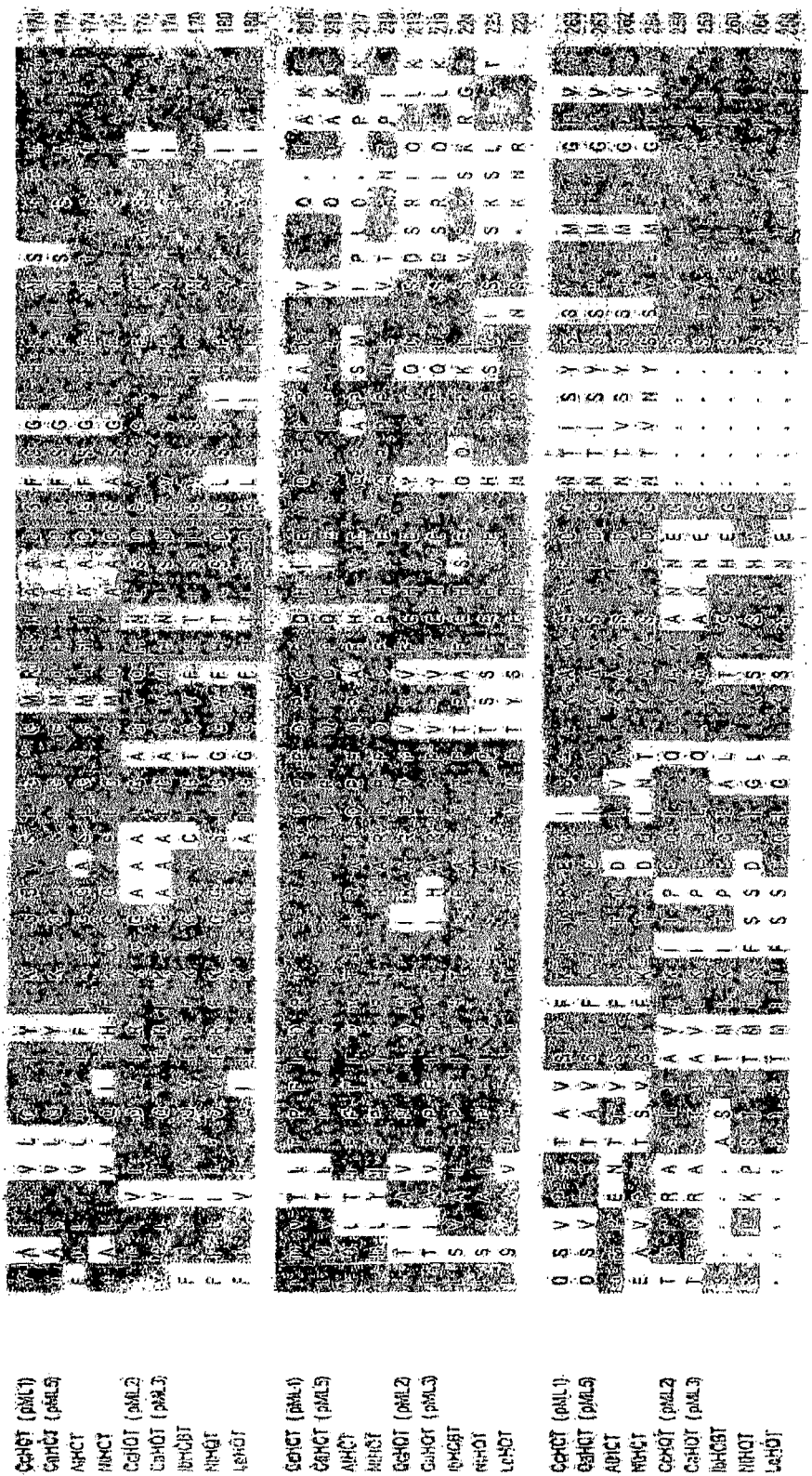
Figure 4:
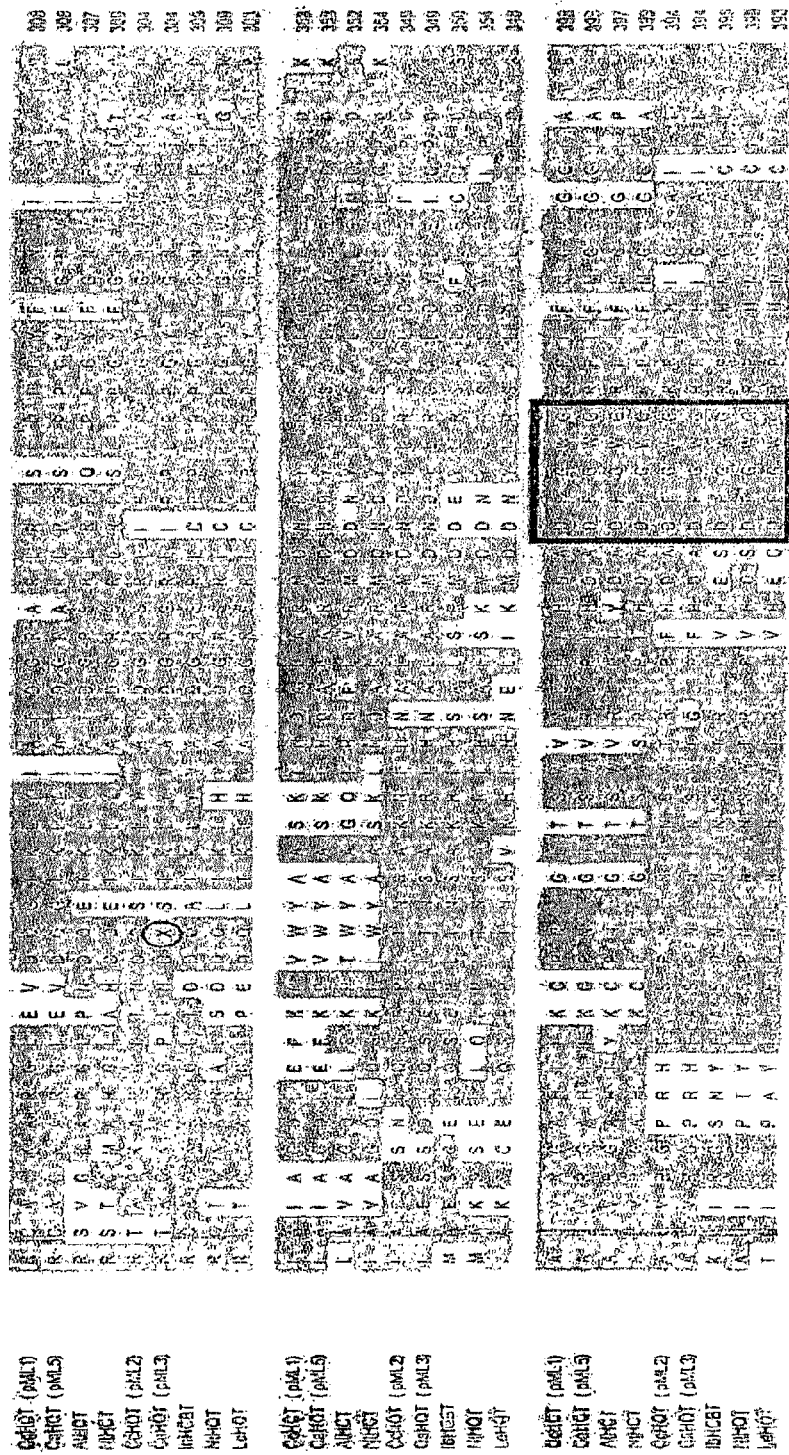
Figure 4:
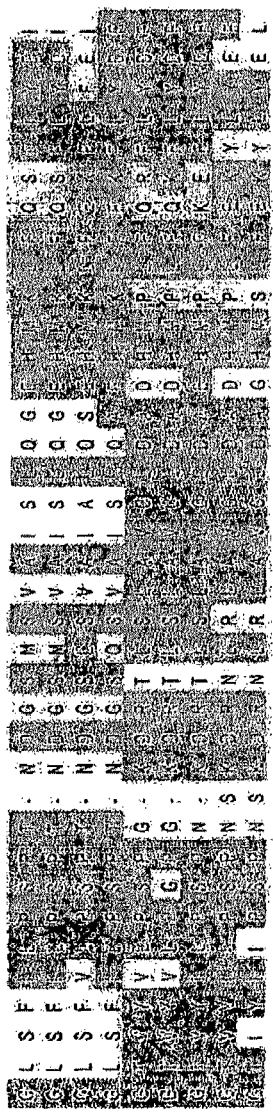

This newly isolated coffee 5' end HCT sequence (Race1_CcHCT) (SEQ ID NO:17), and the nearly full-length coding sequence in the cDNA pcccwc22w14m23 (SEQ ID NO:18), allowed the design of two new primers (HCT-Ful-lUp1 (SEQ ID NO:50) and CcHCT-R1 (SEQ ID NO:51), Tables 3 and 4) for specific amplification of the complete ORF sequence of the coffee HCT using cDNA made by Method 1 from RNA of C. canephora (BP-409) grain at the yellow development stage. This PCR amplification experiment resulted in the generation of the cDNA sequence CcHCT (SEQ ID NO:1) contained in the plasmid pML1 (FIG. 2b). Sequence analysis of the pML1 insert (SEQ ID NO:1) indicated that this cDNA was 1388 bp long, with a complete ORF of 1305 bp encoding a polypeptide of 434 amino acids (SEQ ID NO:9) having an estimated molecular weight of 48.06 kDa. Alignment of the complete HCT protein sequence (SEQ ID NO:9) with protein sequence of the tobacco HCT and a related sequence from Arabidopsis thaliana (accession number CAD47830 (SEQ ID NO:20) and NP_199704 (SEQ ID NO:21), respectively, see FIG. 4) confirmed that the initial annotation of this coffee sequence using BLAST, i.e., the ORF of pML1 (SEQ ID NO:1) encodes a coffee HCT protein. At the protein level, the coffee sequence (SEQ ID NO:9) exhibits 86.9% and 78.3% homology with the tobacco and A. thaliana sequences, respectively (FIG. 4). At the nucleic level, the complete ORF of the coffee sequence exhibits 78.5% and 70% homology with the tobacco and A. thaliana complete ORF sequences, respectively. The protein sequence alignment also shows that the coffee HCT sequence of pML1 has two conserved sequences, HXXXD (SEQ ID NO:25) and DFGWG (SEQ ID NO:26), which have been identified as key regions in acyltransferases class of plant proteins.

EXAMPLE 4

Isolation and Characterization of a *Coffea arabica* cDNA Clone Encoding Hydroxycinnamoyl-CoA Shikimate/Quinate Hydroxycinnamoyltransferase (CaHCT)

Total genomic DNA was extracted from fresh leaves of C. arabica T2308 harvested from the greenhouse using the method of Crouzillat et al., (1996). Primer assisted walking was performed using the Universal GenomeWalker kit (BD Biosciences) according to the protocol suggested by the manufacturer. The four GenomeWalker libraries used here were previously constructed from C. arabica T2308 genomic DNA that had been digested with DraI, EcoRV, PvuI, StuI and then blunt-end ligated to the GenomeWalker Adaptor of the Universal GenomeWalker kit. Both the genomic DNA digestions and the GenomeWalker Adaptor ligation reactions were carried out in accordance with the manufacturer's instructions. The four libraries were then used as templates in PCR reactions using the HCT-GSP gene-specific primers (Table 6). The PCR reaction mixtures contained 10 µl of GenomeWalker library template (1/100 diluted), 5 µL 10×PCR buffer (LA buffer II Mg++ plus), 200 µM of each dNTP, 400 nM of each primer (AP1 and HCT-GSP1), and 0.5 U of DNA polymerase Takara LA Taq (Cambrex Bio Science) in a final volume of 50 µl. The following conditions were used for the first PCR: after denaturing for 2 minutes at 95° C., the first seven cycles were performed at 95° C. for 25 s, followed by an annealing and elongation at 72° C. for 3 min. A further 31 cycles were carried out, at 95° C. for 25 s, with an annealing/elongation temperature of 67° C. for 3 min. An additional final step of elongation was carried out at 67° C. for 7 minutes.

Figure 3A:
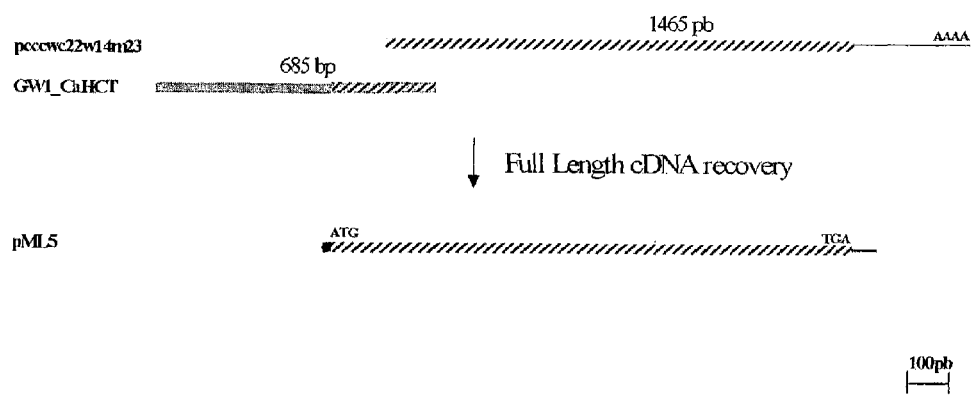
FIG. 3. Isolation and characterization of the complete ORF for CaHCT from *Coffea arabica*. A) Isolation of a cDNA containing the complete ORF of HCT from *Coffea arabica*. A genomic DNA fragment (GW1_CaHCT) (SEQ ID NO:19) encoding the 5' end of a *C. arabica* HCT was obtained (see methods in examples) that contains an overlap with the *C. canephora* HCT cDNA pcccwc22w14 m23 (SEQ ID NO:18). The *C. arabica* genomic sequence contained nearly an identical match to the 5' end primer sequence HCT-FullUp1 (SEQ ID NO:50), so this primer was used with CcHCT-R1 to PCR amplify a 1388 bp fragment (CaHCT in pML5) (SEQ ID NO:2) from *C. arabica* T2308 cDNA (grain, yellow stage). The 5' untranslated region is shown as a thick black bar, the ORF region is shown as a hatched bar, the translation initiation start (ATG) and stop (TGA) codons are indicated. The 3' untranslated region is shown as a thin black line. The genomic region is shown as a thick gray line. It is noted that the majority of the 5' untranslated region of this gene has not yet been defined. B) The insert sequence of pML5 was aligned with the *C. arabica* genomic sequence GW1_CaHCT (SEQ ID NO:19) and the *C. canephora* cDNA sequence pcccwc22w14m23 (SEQ ID NO:18) using CLUSTAL W and manually optimized. Nucleic acids marked in gray match the pML5 (CaHCT) (SEQ ID NO:2) insert sequence.
Figure 3B:
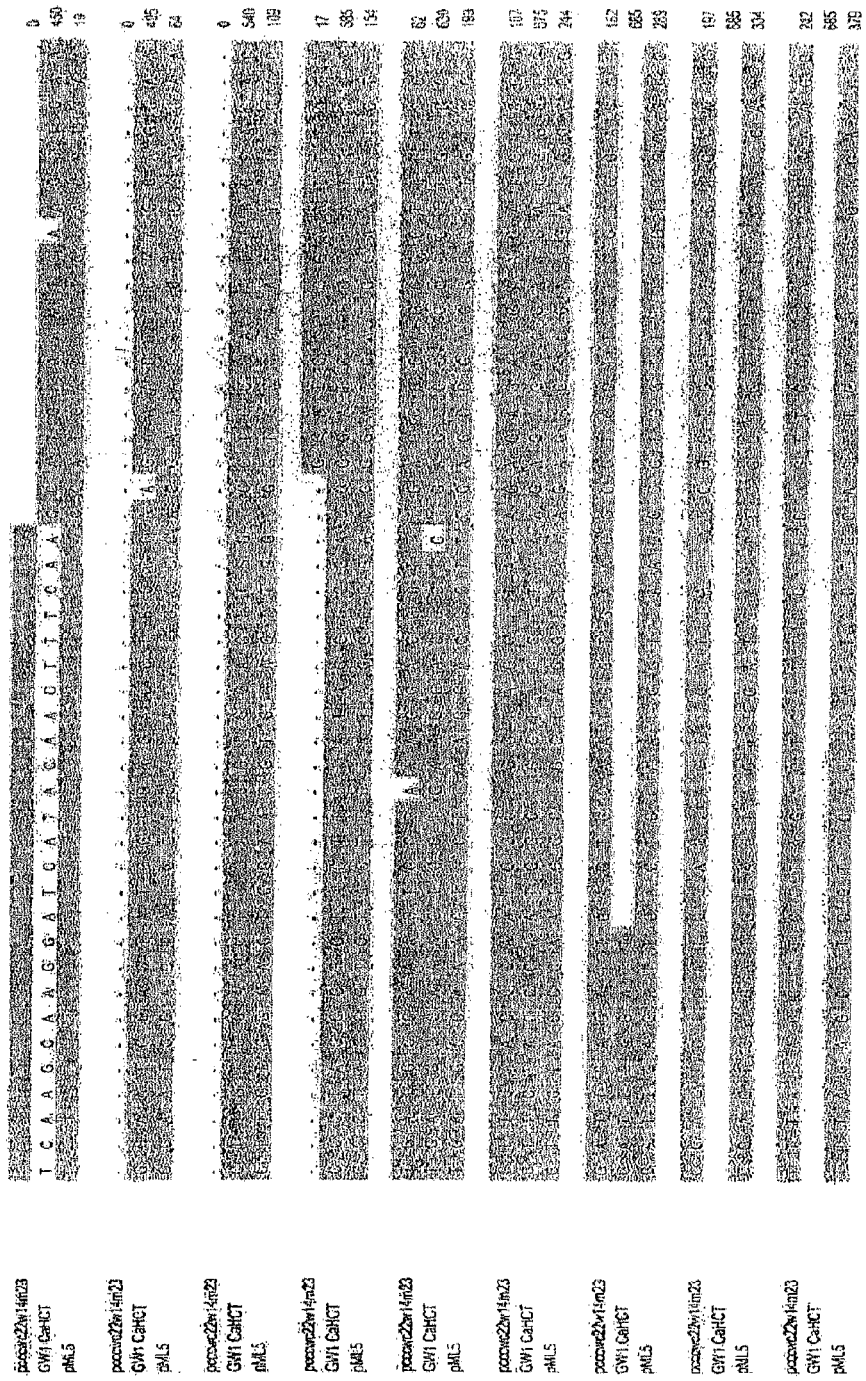
Figure 3B:
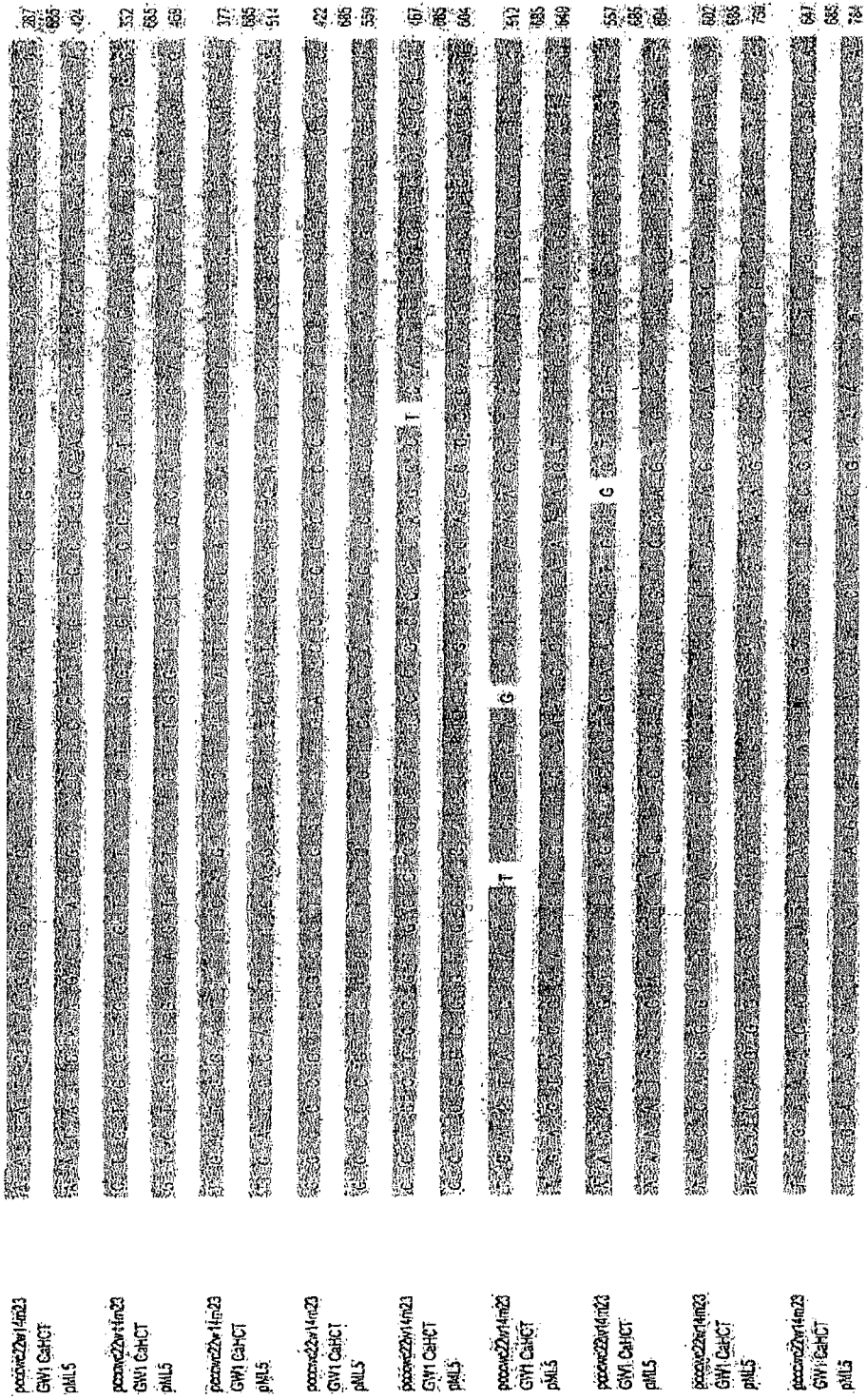
Figure 3B:
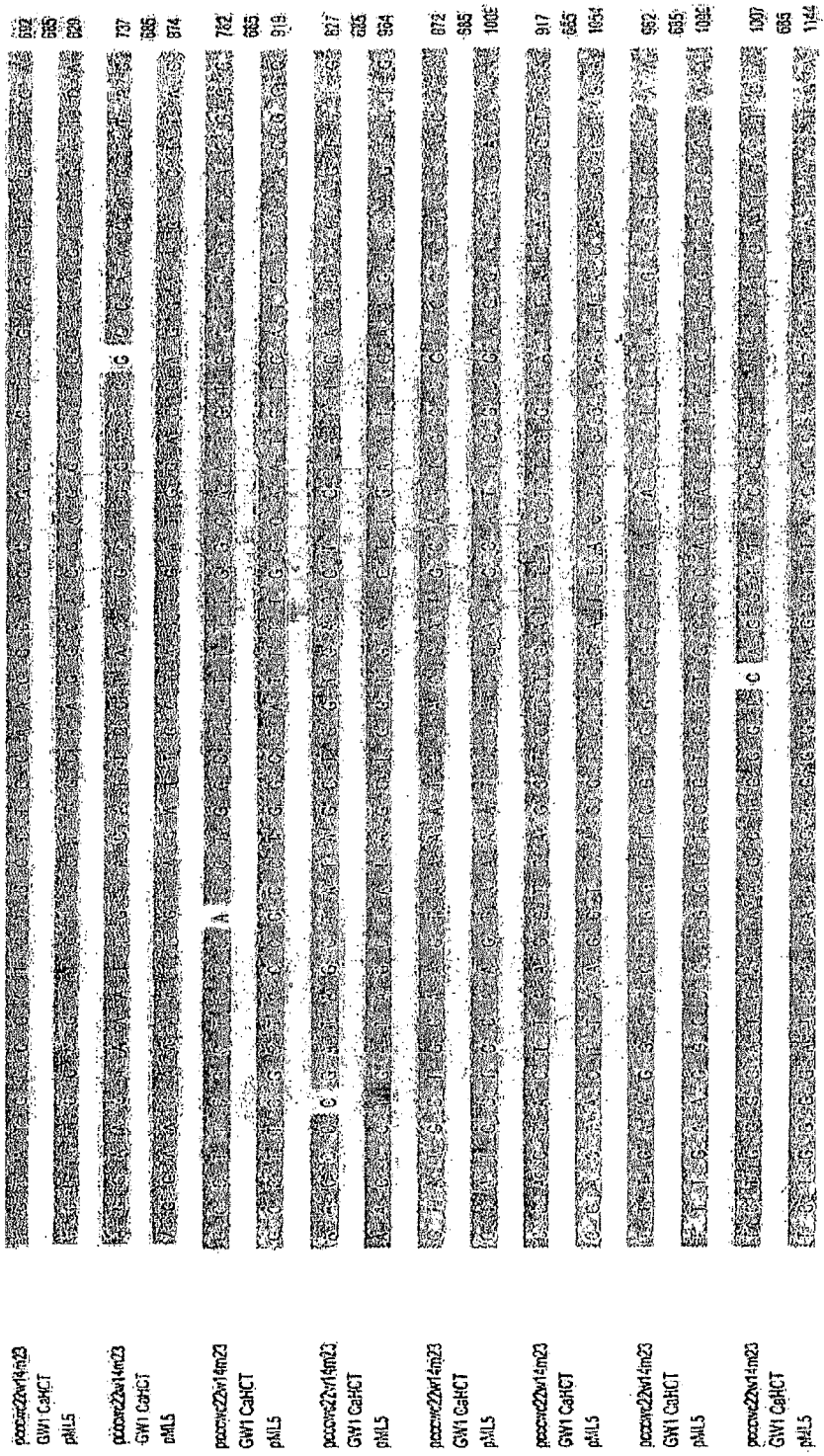
Figure 3B:
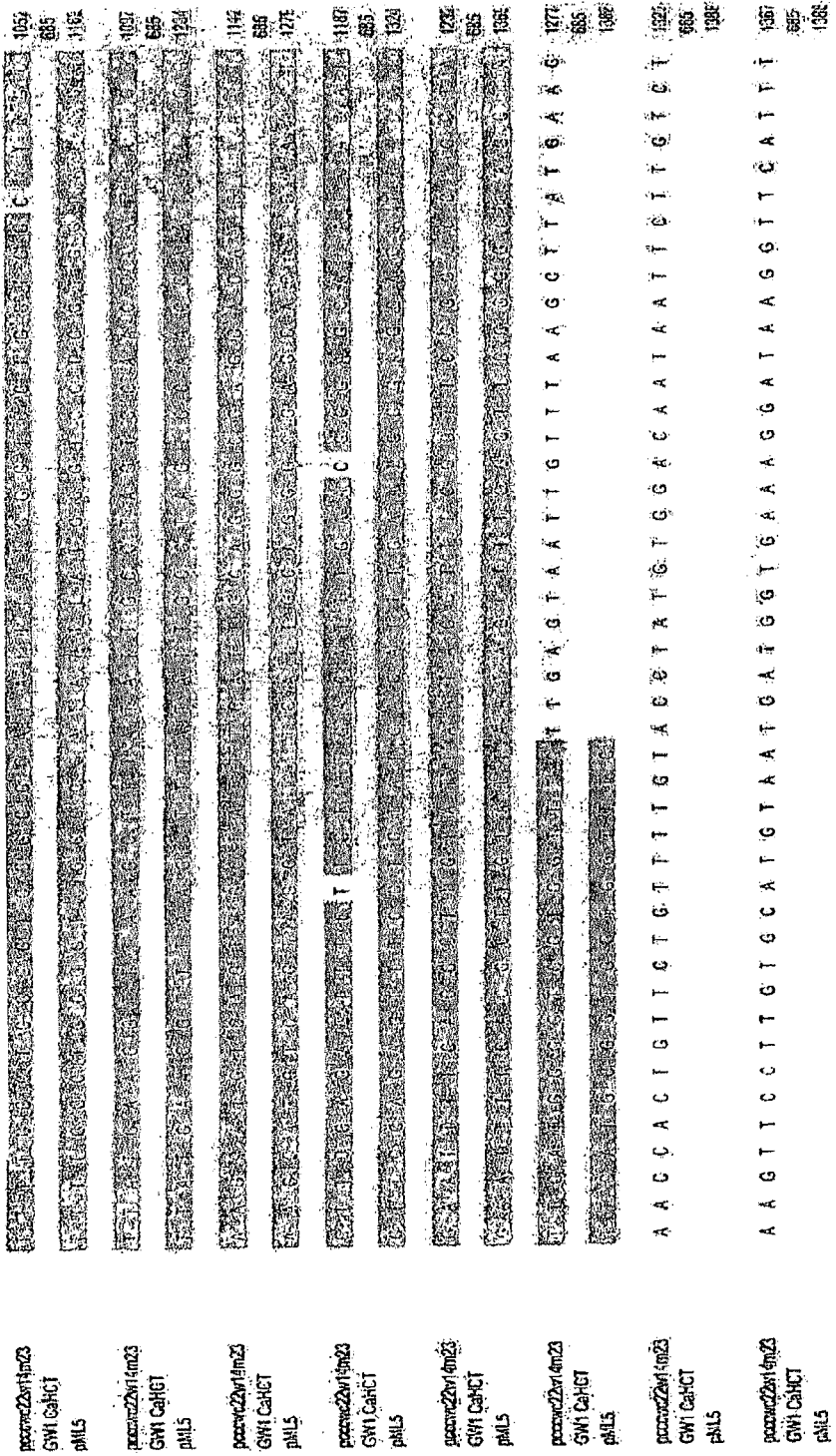

The second PCR reaction was set up exactly as described above for the first round, except the DNA substrate was 1 µl of the first amplification reaction which had been diluted 1/50 from the first reaction. The PCR cycling conditions were 5 cycles of denaturing at 94° C. during 25 s, annealing and elongation 72° C. for 3 min. A further 25 cycles were carried out, at 95° C. for 25 s and an annealing/elongation temperature of 67° C. for 3 min. An additional final step of elongation was carried out at 67° C. for 7 minutes. The resulting PCR fragments were separated by agarose gel electrophoresis. One PCR product from the StuI library named GW1_CaHCT, showing a unique band, was then cloned in pCR4-TOPO using TOPO TA Cloning Kit for Sequencing (Invitrogen), then PCR was carried out on positive isolated colonies. The PCR product with the expected length was then sequenced with T7 and T3 primers. The resulting sequence (GW1-CaHCT) (SEQ ID NO:19) was 685 bp long and overlapped the sequence in pcccwc22w14m23 (SEQ ID NO:18) over 117 bp (FIG. 3A, 3B). It is noted that this genomic sequence probably encodes approximately 430 bp of the 5' non coding region of the CaHCT gene, and thus encodes at least part of this genes promoter.

TABLE 6

Primers used for GenomeWalker experiments.

| Primers | Sequences | Sequence Identifier No: |
|---------|-----------|-------------------------|
| AP1 | 5'GTAATACGACTCACTATAGGGC3' | 81 |
| AP2 | 5'ACTATAGGGCACGCGTGGT3' | 82 |
| HCT-GSP1 | 5'CCATCAGACTCGGCCTCCACGAAAAGCAC3' | 83 |
| HCT-GSP2 | 5'CACTCAATCTCAATCCGCCCATCTTCGTCTCT3' | 84 |

The same set of specific primers and PCR conditions used to isolate the complete ORF of C. canephora HCT (CcHCT) were employed to isolate a cDNA encoding a complete ORF for C. arabica HCT (see Example 2 and Tables 3 and 4 for details). cDNA was made using Method 1 from RNA isolated from C. arabica (T2308) grain at the yellow stage and cloned into plasmid pML5 (FIG. 3b). Sequence analysis of the pML5 insert (SEQ ID NO:2) indicated that this cDNA was 1388 bp long, with a complete ORF of 1305 bp encoding a polypeptide (SEQ ID NO:10) of 434 amino acids having an estimated molecular weight of 48,186 kDa. An optimal alignment of the inserts in and pML1 (CcHCT) (SEQ ID NO:1) and pML5 (CaHCT) (SEQ ID NO:2) using ClustalW shows that the two sequences have 98.9% identity at the DNA level, with 14 single nucleotides differences being observed between the two sequences. These differences within the DNA sequence for the ORF's translate into 5 alterations in the amino acid sequence (FIG. 4). It is noted that more significant sequence variations could be expected in the 5' and 3' UTR sequences of these genes, most of which are missing from pML1 and pML5. As shown in FIG. 4, all four HCT sequences have the same sequence (HHAAD) (SEQ ID NO:85) in the highly conserved HXXXD (SEQ ID NO:25) box. This further supports the contention that pML1 and pML5 encode coffee HCT proteins.

EXAMPLE 5

Isolation and Characterization of a *Coffea canephora* cDNA Clone Encoding Hydroxycinnamoyl-CoA Quinate Hydroxycinnamoyltransferase (CcHQT)

The recently published protein sequences for tobacco HQT (NtHQT, accession number CAE46932; Niggeweg et al., 2004) and tomato HQT (LeHQT, accession number CAE46933, Niggeweg et al., 2004) were employed in a search against the "unigene" set 5 using the tblastn algorithm. Using tobacco NtHQT as the query sequence, the two best hits were unigene #125212 (e value=e−119) and unigene #123197 (e value=e−100). Using tomato LeHQT as the query sequence, the two best hits were also unigene #125212 (e value=e−127) and unigene #123197 (e value=e−103). The very high e value scores for unigene #125212 from the BLAST searches with the NtHQT and LeHQT protein sequences strongly indicated that this in silico unigene sequence was likely to encode a HQT protein.

One of the longest EST for unigene #125212, (pcccs30w13p12) (SEQ ID NO:28) was isolated from the pericarp library and fully sequenced. Sequence analysis showed this cDNA encoded a 1056 bp insert containing a partial ORF encoding 292 amino acids. The polypeptide sequence encoded by pcccs30w13p12 (SEQ ID NO:28) was aligned with the tobacco and tomato HQT protein sequences using the Megalign software (Laser Gene software package, DNASTAR). These manually optimized alignments confirmed that the partial ORF of pcccs30w13p12 (SEQ ID NO:28) probably encoded a HQT protein. These alignments also indicated that this cDNA clone did not contain a complete ORF. The polypeptide sequence encoded by pcccs30w13p12 (SEQ ID NO:28) was also aligned with the polypeptide sequence encoded by longest cDNA of unigene 123197 (pcccwc22w14m23) (SEQ ID NO:18). This protein alignment showed that these two sequences were significantly different (approximately 61.3% identity at the amino acid level using the ClustalW Method), and thus, these sequences represent different genes.

Figure 5A:
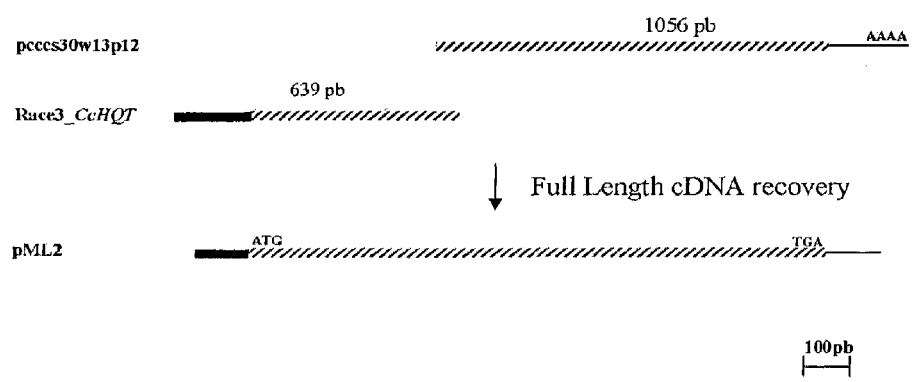
FIG. 5. Isolation and characterization of the complete ORF for CcHQT from *Coffea canephora*. A) Isolation of a cDNA containing the complete ORF for CcHQT from *C. canephora*. Two cDNA fragments (Race3_CcHQT (SEQ ID NO:27) and pcccs30w13p12 (SEQ ID NO:28)) were obtained covering the complete ORF of CcHQT (see methods in examples). These sequences were used to design the primers to PCR amplify the 1534 bp fragment (CcHQT in pML2) (SEQ ID NO:3) from *Coffea canephora* BP409 (pericarp, small green stage). The protein-coding region is shown as a hatched line, the translation initiation start (ATG) and stop (TGA) codons are indicated. The 3' untranslated region is shown in thin black line. Symbols are the same as for FIGS. 2 and 3, B) The insert sequence of pML2 was aligned with the cDNA sequences Race3_CcHQT (SEQ ID NO:27) and pcccs30w13p12 (SEQ ID NO:28). The alignment was done using the CLUSTAL W and manually optimized. Nucleic acids marked in gray match the pML2 (CcHQT) insert sequence (SEQ ID NO:3).

The alignment of the tomato and tobacco HQT protein sequences with the partial ORF sequence of pcccs30w13p12 (SEQ ID NO:28) showed that this coffee HQT sequence lacked approximately 140-150 amino acids at the N-terminal end. However, based on the significant part of the coffee HQT sequence encoded by pcccs30w13p12 (SEQ ID NO:28), specific primers for use in the well established technique of 5' RACE PCR were devised to isolate the missing 5' end of the coffee HQT coding sequence. Using the cDNA prepared by Method 1 using RNA isolated from *C. canephora* (BP 409) pericarp (all developmental stages mixed) and the primers and PCR conditions set forth in Example 2 above, a unique fragment of approximately 750 bp was obtained and directly sequenced using specific primer 22m12-GSP2 (SEQ ID NO:43) for amplification of the fragment. The resulting sequence (RACE3_CcHQT) (SEQ ID NO:27) was 639 bp long and, overlapped the 5' end of the sequence in pcccs30w13p12 (SEQ ID NO:28) by 62 bp. (FIG. 5a).

Figure 5B:
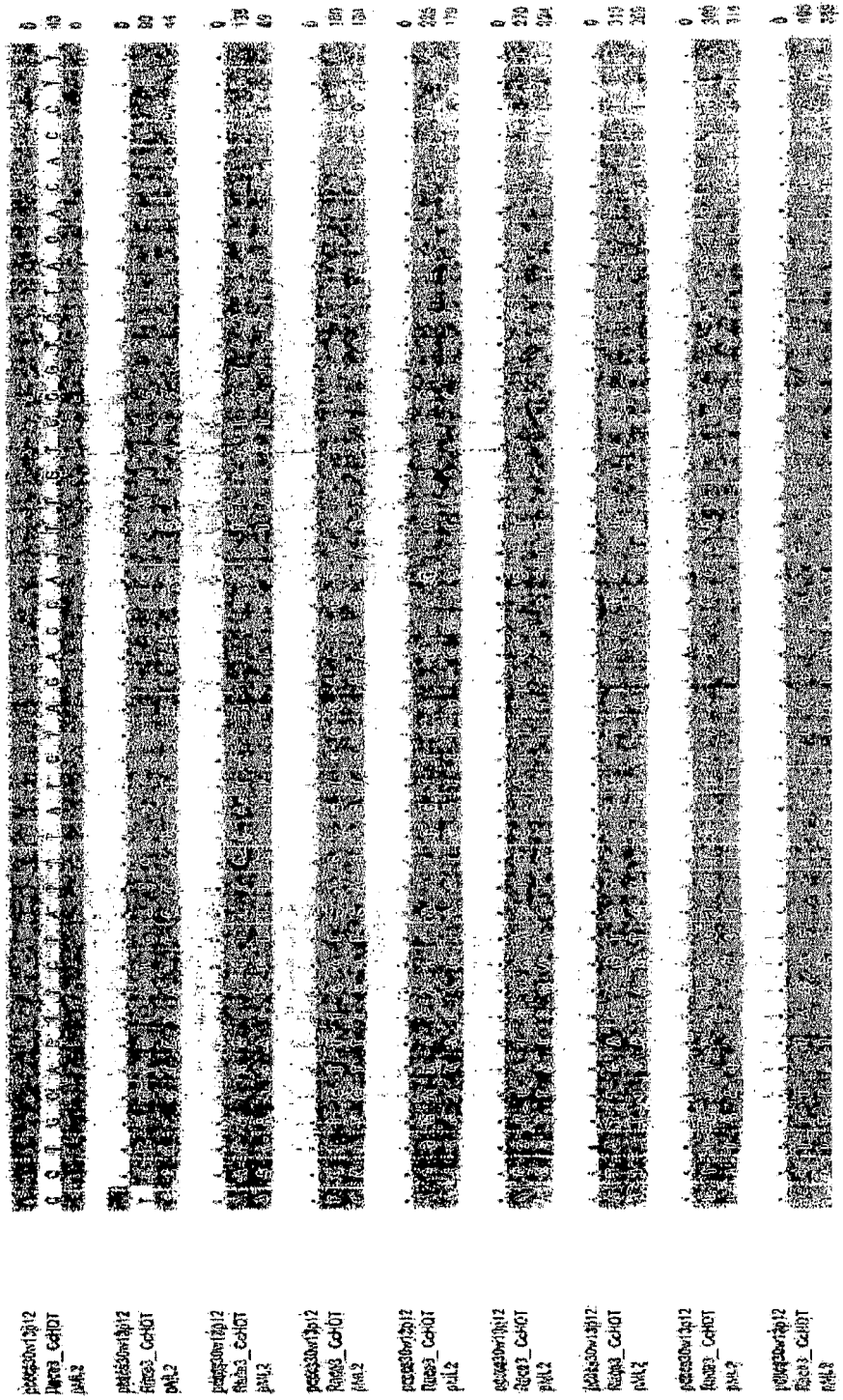
Figure 5B:
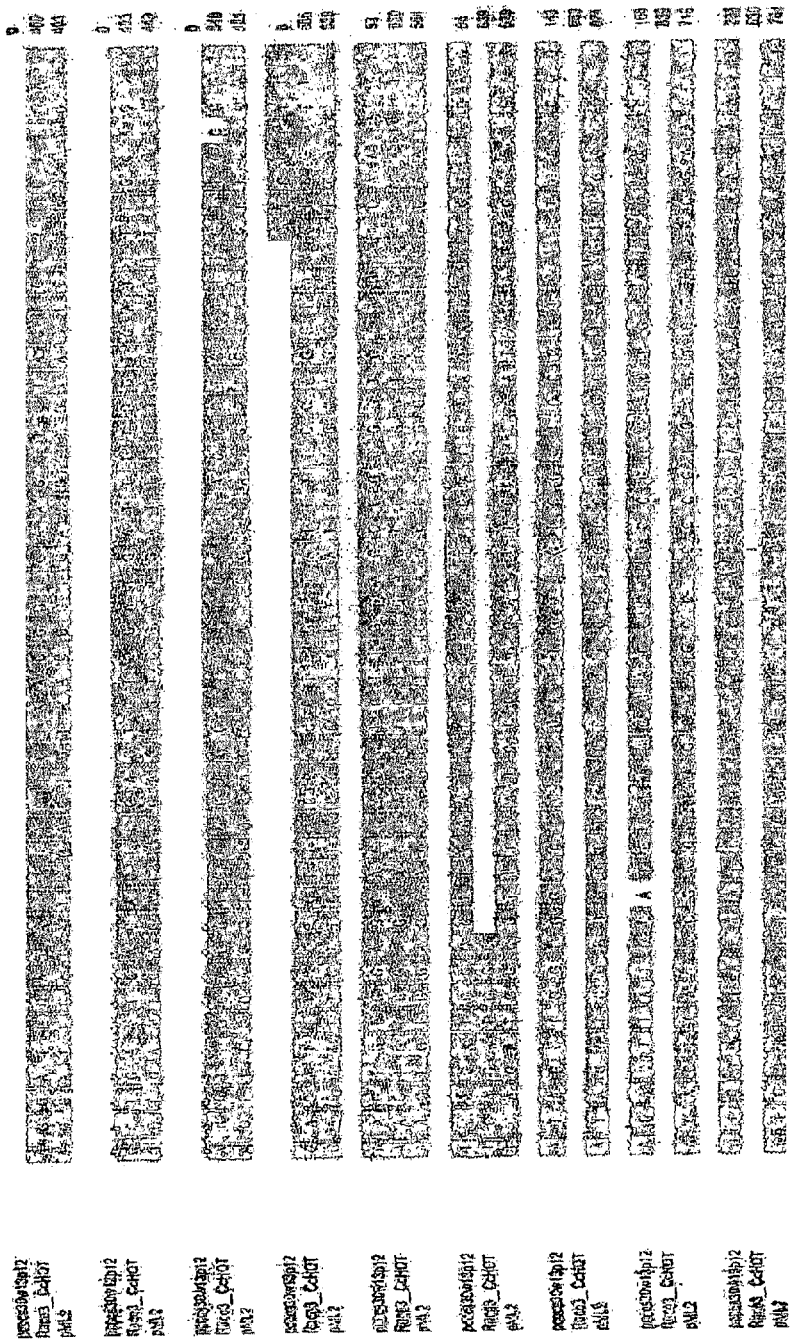
Figure 5B:
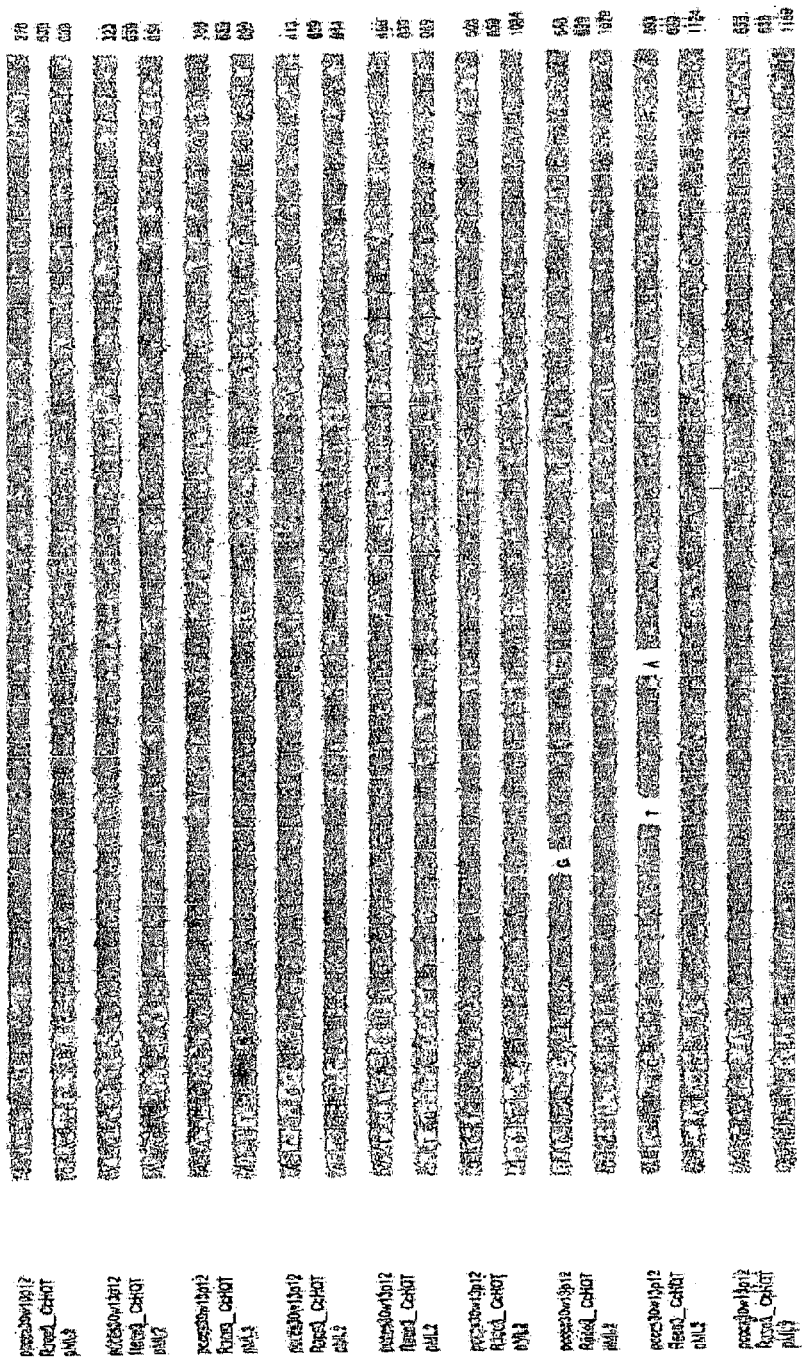
Figure 5B:
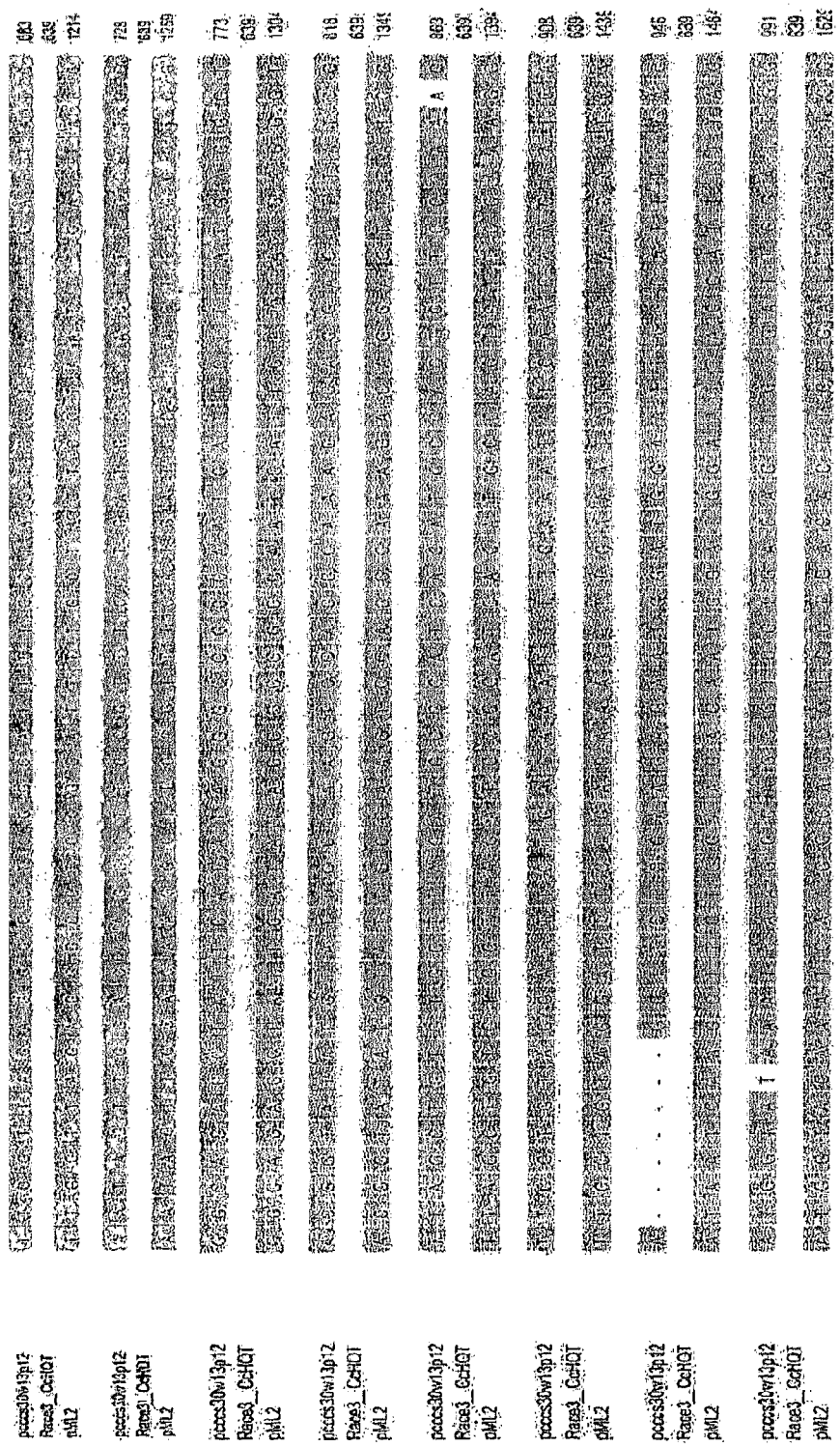
Figure 6A:
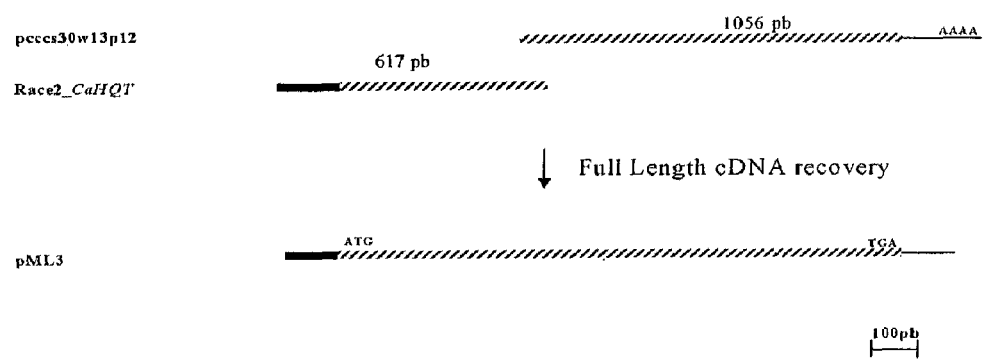
FIG. 6. Isolation and characterization of the complete ORF for CaHQT from *Coffea arabica*. A) Isolation of a cDNA containing a complete ORF encoding CaHQT from *C. arabica*. A 5' RACE cDNA fragment (Race2_CaHQT) (SEQ ID NO:29) was obtained which encodes the 5' end of a *C. arabica* HQT. The primers HQT-Fullup2 (SEQ ID NO:52) and HQT-FullLow2 (SEQ ID NO:53) previously used to PCR amplify CcHQT were also successfully used to amplify a 1533 bp fragment (CaHQT in pML3) (SEQ ID NO:4) from *C. arabica* T2308 cDNA (whole flowers). Symbols are the same as for FIGS. 2 and 3. B) The insert sequence (SEQ ID NO:4) of pML3 was aligned with the *C. arabica* cDNA sequence Race2_CaHQT (SEQ ID NO:29) and the *C. canaphora* sequence pcccs30w13p12 (SEQ ID NO:28). The alignment was done using CLUSTAL W and manually optimized. Nucleic acids marked in gray match the pML3 (CaHQT) sequence (SEQ ID NO:4). The encircled base shows a stop codon in the ORF of pML3 (SEQ ID NO:4), as discussed in the text and in the legend for FIG. 4.
Figure 6B:
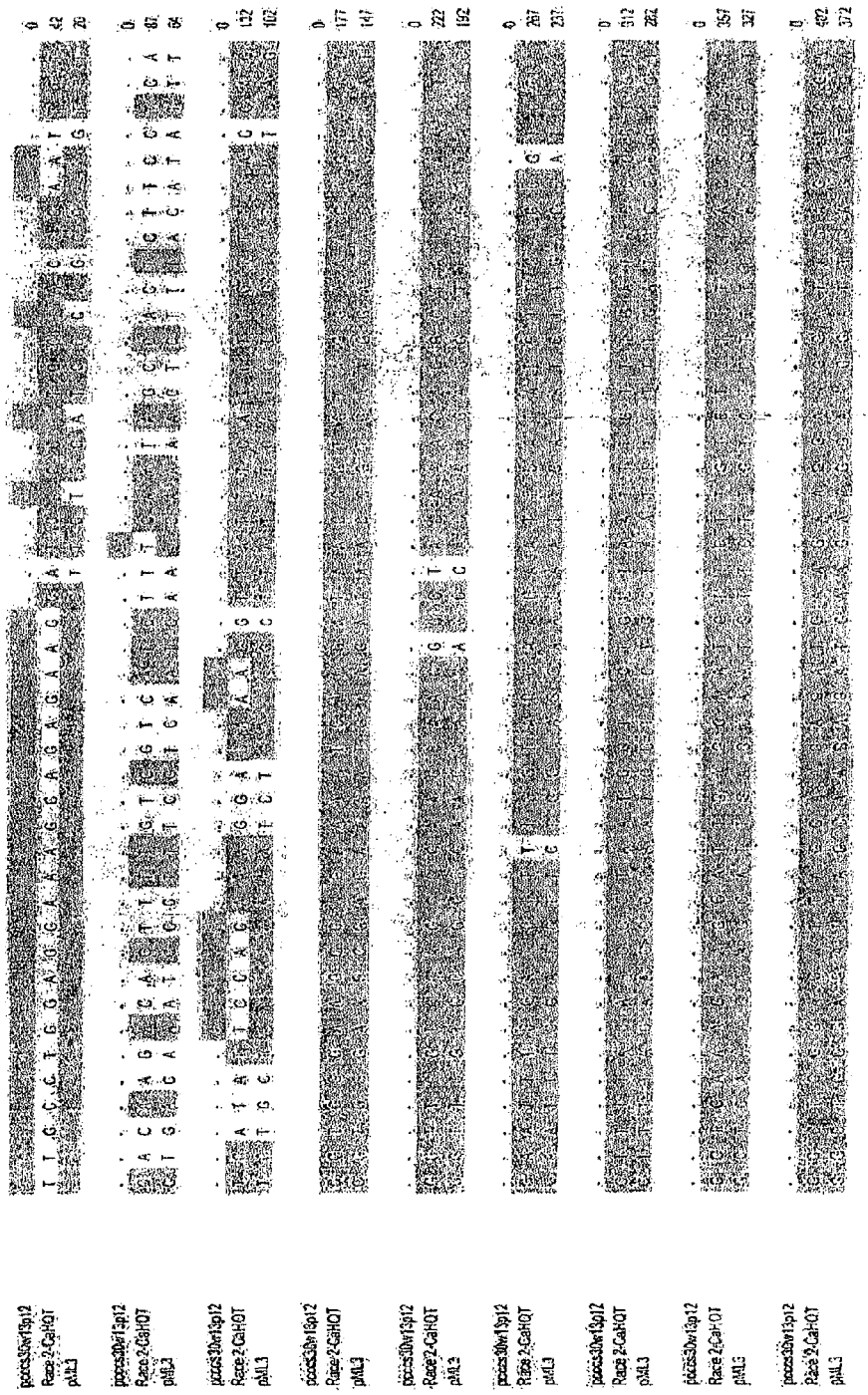
Figure 6B:
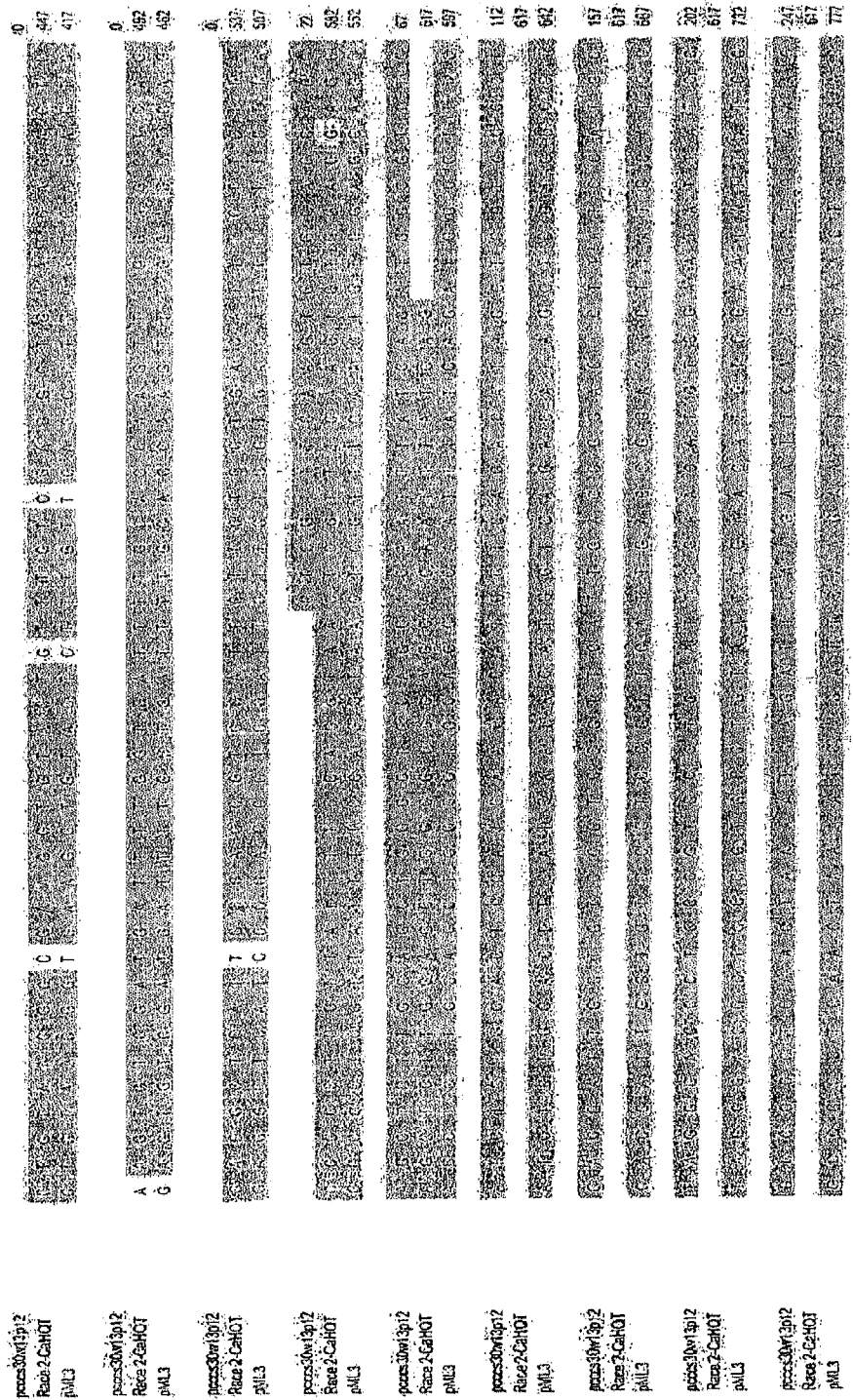
Figure 6B:
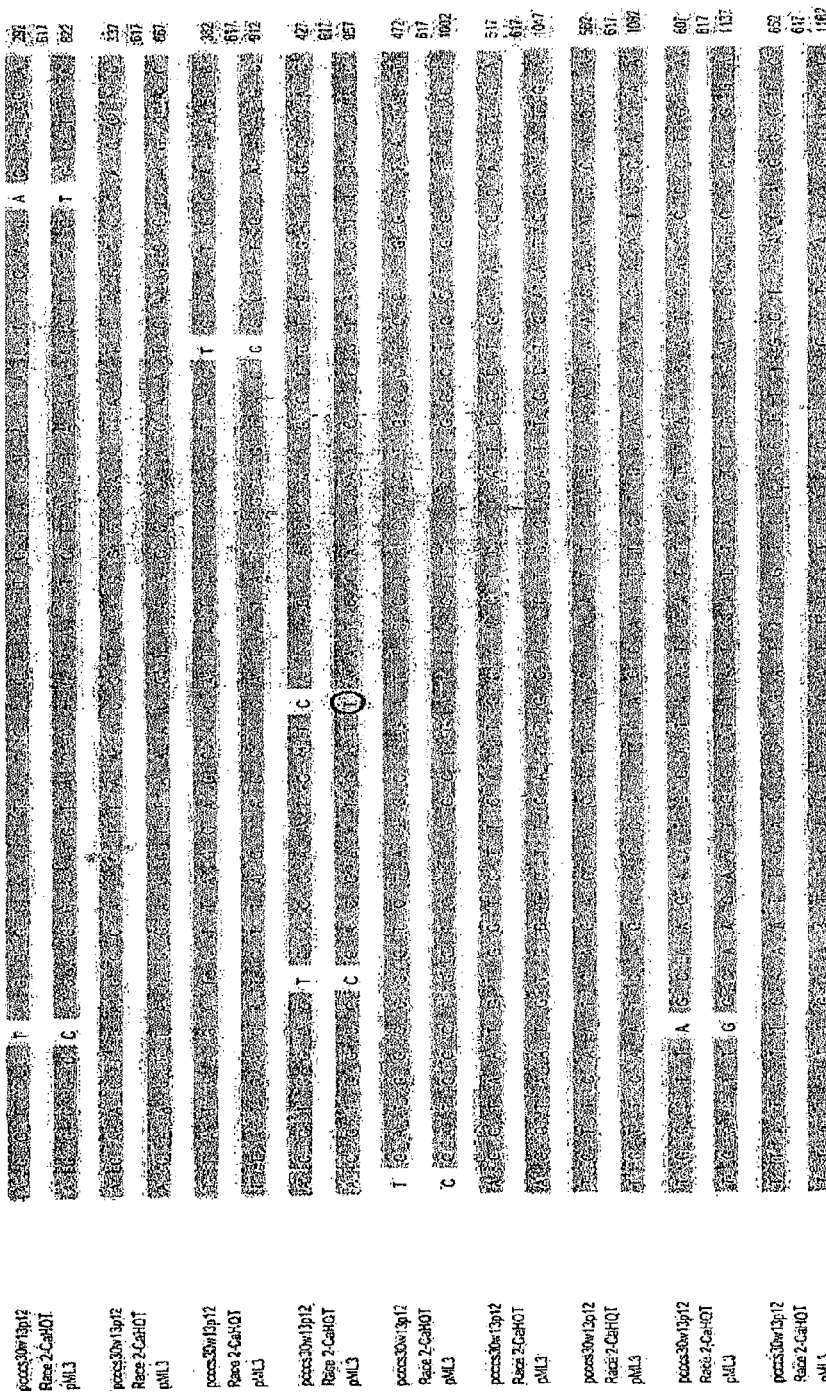

This newly isolated *C. canephora* 5' end HQT sequence (RACE3_CcHQT) (SEQ ID NO:27), and the coding sequence in the cDNA pcccs30w13p12 (SEQ ID NO:28), allowed the design of two new primers capable of specifically amplifying the complete ORF sequence of a CcHQT from coffee HCT using cDNA made from RNA of *C. canephora* (BP-409) pericarp at the small green stage. (Tables 3 and 4). The cDNA obtained was cloned into plasmid pML2 (FIGS. 5A and 5B). Sequence analysis of the insert in pML2 (SEQ ID NO:3) indicated that this cDNA was 1534 bp long and had a complete ORF of 1293 bp, encoding a polypeptide (SEQ ID NO:11) of 430 amino acids having an estimated molecular weight of 47.72 kDa.

Alignment of the complete CcHQT ORF sequence (SEQ ID NO:3) with the previously characterized tobacco and tomato HQT sequences, and the highly-related sequence from *Ipomea batatas* IbHCBT accession number BAA87043 (SEQ ID NO:22) confirms the initial annotation of this coffee sequence from the BLAST analysis, i.e., the complete ORF of pML2 (SEQ ID NO:3) encodes a coffee HQT protein (SEQ ID NO:11) (FIG. 4). At the protein level, the coffee HQT protein sequence exhibits 75.8%, 75.1% and 78.1% homology to the tobacco, tomato and *I. batatas* sequences, respectively. At the nucleotide level, the coffee HQT ORF sequence exhibits 72.1%, 70.1% and 71.1% identity with the tobacco, tomato and *I. batatas* ORF sequences, respectively.

The alignment in FIG. 4 also shows the coffee HQT sequence of pML2 (SEQ ID NO: 11) has the two conserved sequences, HXXXD (SEQ ID NO:25) and DFGWG (SEQ ID NO:26), which have been identified as key regions in the acyltransferases class of plant proteins (Yang et al. 1997, St-Pierre et al. 2000, Hoffmann et al. 2003). As shown in FIG. 4, all five HQT sequences have nearly the same sequence (HT/NLSD) in the highly conserved HXXXD (SEQ ID NO:25) box, further supporting the contention that pML2 encodes a coffee HQT protein.

EXAMPLE 6

Isolation and Characterization of a *Coffea arabica* cDNA Clone Encoding Hydroxycinnamoyl-CoA Quinate Hydroxycinnamoyltransferase (CaHQT)

The same set of specific primers and PCR conditions used to isolate the complete ORF of *C. canephora* HQT were employed to isolate a cDNA encoding a complete ORF for *C. arabica* HQT (see Example 2 and Table 3 and 4). The cDNA employed was prepared, using Method 1, from RNA isolated from *C. arabica* (T2308) flowers and the specific CaHQT fragment amplified was subcloned to generate the plasmid pML3 (FIG. 6). Sequence analysis of the insert in pML3 revealed that this cDNA was 1533 bp long and had a potentially complete ORF of 1293 bp that was interrupted by a single stop codon at position 814-816 in the ORF sequence (position 272 in the protein). It is presumed that this mutation resulted from a single base pair mutation (CAA to TAA) during the PCR amplification with Taq DNA polymerase. To ensure the stop codon was generated by Taq and is not a genome-encoded stop codon, cDNA was prepared using Method 1 from RNA isolated from *C. arabica* T2308 roots. This cDNA was then used to PCR-amplify the region of the stop codon.

The PCR reaction was performed in a final 50 µl volume, as follows; 5 µL of cDNA; 10×PCR buffer (LA buffer II Mg$^{++}$ plus), 500 nM of the primer HQT-FullLup1 (5' CTGGAG-GAAAGCAGAGAAGCAT 3') (SEQ ID NO:86) and HQT-FullLow2 (SEQ ID NO:52) (Table 3A) primers, 200 µM each dNTP, 0.5 U of DNA polymerase Takara LA Taq (Cambrex Bio Science). The PCR reaction conditions were as follows: 94° C. for 2 min; then 94° C. for 1 min, 56° C. for 1 min and 72° C. for 2 and 40 cycles. An additional final step of elongation was carried out at 72° C. for 7 min. The PCR product was then analyzed by agarose gel electrophoresis and ethidium bromide staining.

This PCR amplification produced a unique fragment of approximately 1600 bp. This unique fragment (R-CaHQT)

was then directly sequenced using the HQT-FullLow2 primer (SEQ ID NO:52) (Table 4). A 626 bp sequence was obtained that overlapped completely with the pML3 (CaHQT) sequence (SEQ ID NO:4). The sequence of this new cDNA fragment encoded the region containing the mutation site (98.9% homologous over in the 626 bp overlapping region), and at the mutation site, it had CAA (for expected amino acid Q) and not TAA (STOP) as found in pML3.

Comparison of the cDNA sequences cloned for CcHQT (SEQ ID NO:3) and CaHQT (SEQ ID NO:4) revealed 15 single nucleotide differences. The optimized alignment of the polypeptide sequences of CcHQT (SEQ ID NO:11) and CaHQT (SEQ ID NO:12) revealed 7 amino acid differences (FIG. 4).

EXAMPLE 7

Isolation and Characterization of a *Coffea canephora* cDNA Clone Encoding p-coumaroyl 3' Hydroxylase CcC3H To find coffee cDNA encoding the enzyme p-coumaroyl shikimate 3'-hydroxylase (C3H), two protein sequences encoding biochemically well characterized C3H activities, the *Ocimun basilicum* p-coumaroyl shikimate 3'-hydroxylase isoform 2 (Gang et al., 2002; accession number AAL99201) and the *Arabidopsis* cytochrome P450 CYP98A3 (Schoch et al., 2001; accession number O22203) were used to search the "unigene" set 5 using the tblastn algorithm. This search uncovered one unigene (#124852) exhibiting a very high level of homology to the *O. basilicum* and *Arabidopsis* C3H protein sequences. A cDNA representing the 5' end of the unigene #124852 (pcccl20d10 (SEQ ID NO:5)), potentially encoding the full ORF of this protein, was then isolated and sequenced.

Figure 7:
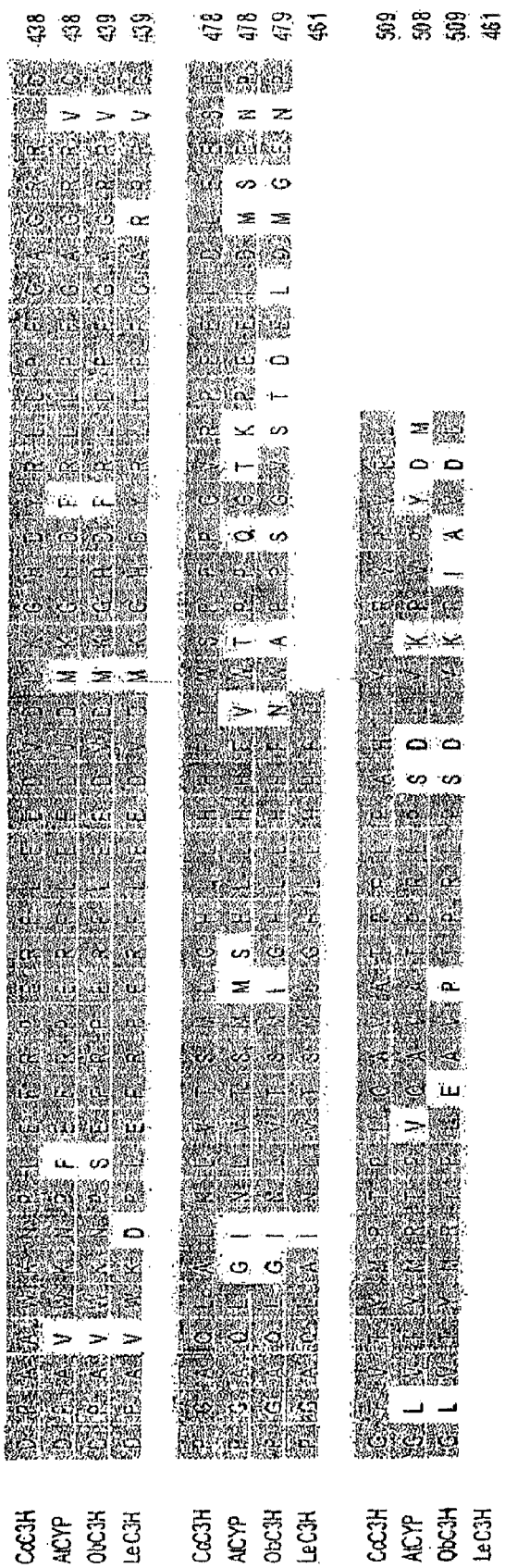
FIG. 7. Alignment of CcC3H with other plant C3H protein sequences. The alignment of the protein sequence (SEQ ID NO:13) encoded by CcC3H (in pcccl20d10 (SEQ ID NO:5)) with other highly related C3H proteins in the NCBI database was done using CLUSTAL W (Note: these proteins are CYP related proteins, thus the *Arabidopsis* protein was originally AtCYP). Amino acids marked in gray match those in the CcC3H sequence (SEQ ID NO:13). AtCYP (*Arabidopsis thaliana* 22203) (SEQ ID NO:30), ObC3H (*Ocinum basilicum*, AAL99201) (SEQ ID NO:31), LeC3H putative (*Lycopersicon esculentum*, TC163965 (TIGR Tomato Gene Index annotation) (SEQ ID NO:32)).

The insert of pcccl20d10 (SEQ ID NO:5) was determined to be 1728 bp long, and to encode an ORF of 1527 bp. The deduced protein sequence (SEQ ID NO:13) comprises 508 amino acids, and has a predicted molecular weight of 57.9 kDa. The protein sequence (SEQ ID NO:13) of pcccl20d10 (SEQ ID NO:5) was aligned with homologous C3H protein sequences from *O. basilicum*, *A. thaliana*, and an orthologous sequence from *L. esculentum* (FIG. 7). This alignment demonstrated that the protein (SEQ ID NO:13) encoded by pcccl20d10 (SEQ ID NO:5) shares, respectively, 75.1%, 73.9% and 82.9% homology with these protein sequences. Thus, it can be concluded that pcccl20d10 (SEQ ID NO:5) encodes a full length cDNA for a *C. canephora* p-coumaroyl shikimate 3'-hydroxylase (CcC3H). An alignment of the DNA sequence encoding the ORF sequence contained in pcccl20d10 (SEQ ID NO:5) with the DNA sequences encoding the ORF sequences of C3H from *O. basilicum* and of the cytochrome P450 CYP98A3 from *A. thaliana* demonstrated that the ORF DNA sequence of CcC3H shares 69.4% and 69.2% identity with the *O. basilicum* C3H and the *A. thaliana* P450 CYP98A3 DNA sequences.

EXAMPLE 8

Isolation and Characterization of Three *Coffea canephora* cDNA Clones Encoding CCoAOMT To find coffee cDNA encoding the enzyme CCoAOMT, two protein sequences encoding well-characterized CCoAOMT activities, CCoAOMT of *Nicotiana tabacum* (accession number AAC49913 (SEQ ID NO:38) Martz et al., 1998) and CCoAOMT of *Medicago sativa* (alfalfa) (accession number AAC28973 (SEQ ID NO:37), Ferrer et al, 2005) were used to search the "unigene" set 5 using the tblastn algorithm. This analysis uncovered 3 unigenes exhibiting relatively high levels of homology to the *N. tabacum* CCoAOMT protein sequences, #119965 (e value=e–125), #122801 (e value=e–63), and #119560 (e value=e–56). These unigenes were also shown to have relatively high homologies to the M sativa protein sequence, ie. #119965 (e value=e–127), #122801 (e value=e–64), and #119560 (e value=e–59).

Figure 12:
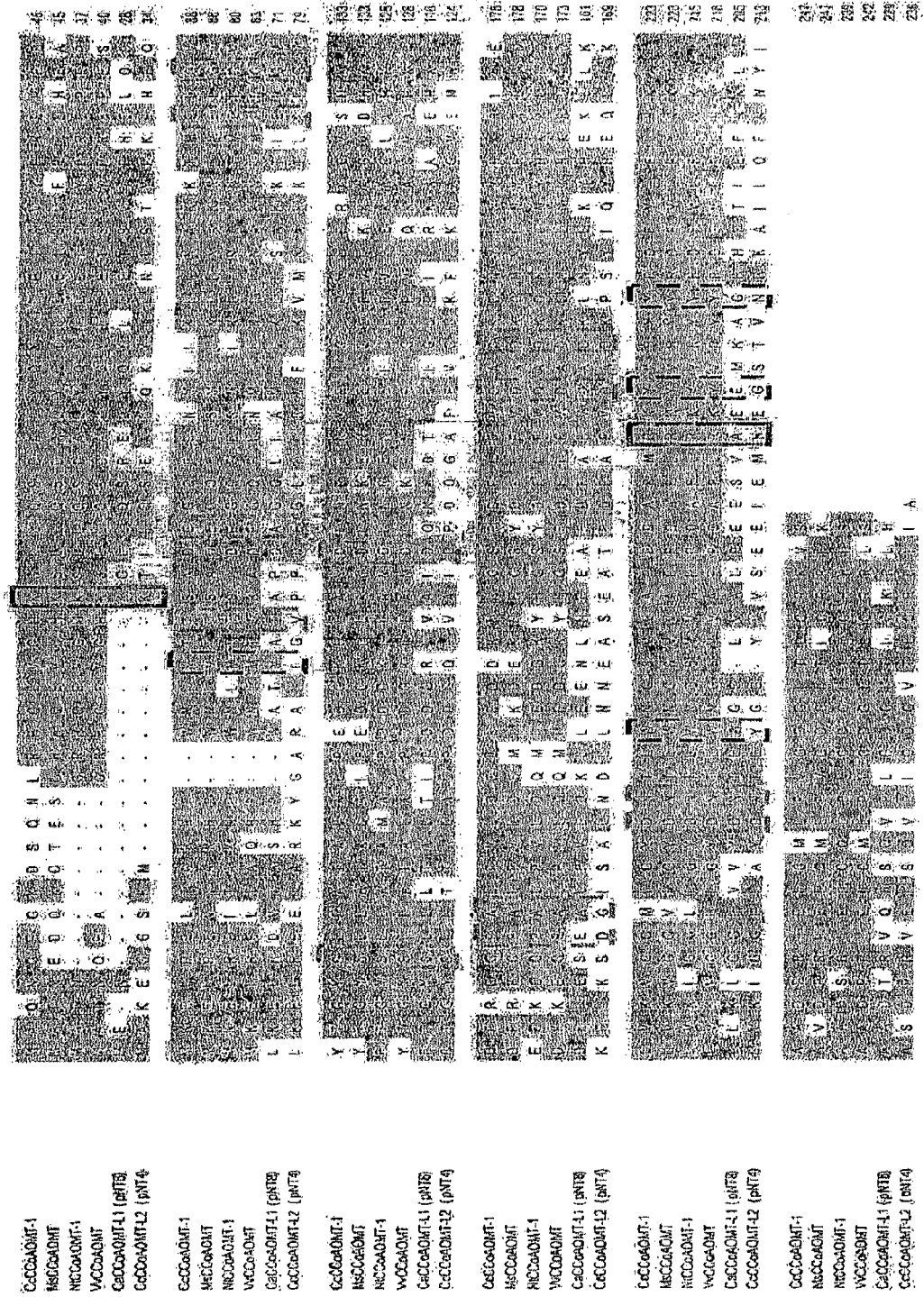
FIG. 12. Protein sequence alignment of CcCCoAOMT-1 (pcccl15a11), MsCCoAOMT, NtCCoAOMT, VvCCoAOMT, CaCCoAOMT-L1 (pNT8), and CcCCoAOMT-L2 (pNT4). An alignment of MsCCoAOMT (SEQ ID NO:37), NtCCoAOMT (SEQ ID NO:38) and VvCCoAOMT (SEQ ID NO:39) protein sequences available in the NCBI database with the protein sequences encoded by CcCCoAOMT-1, CaCCoAOMT-L1 and CcCCoAOMT-L2 genes (SEQ ID NOs:6, 7, 8, respectively) was done using CLUSTAL W and manually optimized. Amino acids marked in gray match the residue most frequently found in that position. The following amino acid interactions were characterized in the recent crystal structure of the alfalfa (*Medicago sativa*) CCoAOMT complexed with reaction products (Ferrer and al, 2005): the pink boxes indicate amino acids which interact with the negatively charged 3'-phosphate group of the adenosine 3'-5' diphosphate moiety of CoA, the blue boxes indicate amino acids involved in substrate recognition, and the green boxes indicate amino acids involved in divalent metal ion and cofactor binding. Accession numbers for protein sequences available in the NCBI database are given in parentheses: MsCCoAOMT (*Medicago sativa*, AAC28973 (SEQ ID NO:37)), NtCCoAOMT (*Nicotiana tabacuin*, AAC49913 (SEQ ID NO:38)), and VvCCoAOMT (*Vitis vinifera*, CAA90969 (SEQ ID NO:39)).

One of the longest cDNA representing the 5' end of the unigene #119965 (pcccl15a11 (SEQ ID NO:6)), and potentially encoding the full ORF of this protein, was then isolated from the leaf library and fully sequenced. The insert of pcccl15a11 (SEQ ID NO:6) was determined to be 1144 bp long and to encode an ORF of 744 bp. The deduced full length protein sequence (SEQ ID NO:14) was determined to be 247 amino acids, with a predicted molecular weight of 27.97 kDa. FIG. 12 shows an optimized alignment of the protein sequence (SEQ ID NO:14) of pcccl15a11 (SEQ ID NO:6) with the CCoAOMT protein sequences from *N. tabacum*, and M sativa revealed that the pcccl15a11 protein shares 85.1%, and 86.3% homology with these protein sequences, respectively. This alignment also demonstrates that the CcCCoAOMT1 protein (SEQ ID NO:14) contains all the amino acid residues which have been determined by Ferrer et al. 2005. The Ferrer group determined the structure of the alfalfa Caffeoyl Coenzyme A 3-O-Methyltransferase by x-ray crystallography to a) interact in Co-enzyme A recognition, b) be involved in substrate recognition, and c) be involved in metal ion divalent and cofactor binding. Thus, this alignment data supports the claim that pcccl15a11 (SEQ ID NO:6) encodes a full length cDNA for a *C. canephora* Caffeoyl CoA-O MethylTransferase (CcCCoAOMT1) (SEQ ID NO:14).

It is noted that the public databases contain a partial cDNA sequence from *C. canephora* (Accession Number AF534905, encoding an ORF of 108aa). When aligned with CcCCoAOMT1 (SEQ ID NO:14), this database sequence exhibits 97.5% identity over the appropriate regions at the DNA level indicating the partial *C. canephora* cDNA (Accession Number AF534905) is probably allelic to the complete cDNA in CcCCoAOMT1, and that there thus are two different *Coffea canephora* alleles of the same gene.

The longest cDNA representing the 5' end of the unigene #122801 (cccs30w29k18), and potentially encoding a CcCCoAOMT-like protein, was isolated from the 30 weeks grain library (30 weeks after flowering) and fully sequenced. The insert of pcccs30w29k18 (SEQ ID NO:34) was determined to be 722 bp long and to encode a partial ORF of 576 bp long. The deduced partial protein sequence was determined to encode 191 amino acids. The partial polypeptide sequence encoded by pcccs30w29k18 (SEQ ID NO:34) was aligned and compared with the CCoAOMT protein sequences from *N. tabacum*, and M sativa. This alignment showed that the insert ORF sequence of pcccs30w29k18 (SEQ ID NO:34) shared 56.2% identity with both these plant CCoAOMT protein sequences, suggesting this protein was potentially a CCoAOMT-LIKE protein. This alignment also indicated that this cDNA clone does not contain a complete ORF.

Figure 9A:
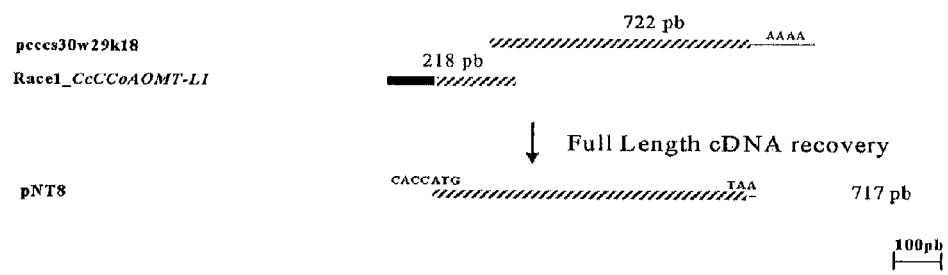
FIG. 9. Isolation and characterization of the complete ORF for CaCCoAOMT-L1 (pNT8) from *Coffea arabica* A) Isolation of cDNA containing the complete ORF for CCoAOMT-L1 (SEQ ID NO:7) from *C. arabica*. One cDNA fragment (Race1_CcCCoAOMT-L1) (SEQ ID NO:33) was obtained from *coffea canephora* (Grain, yellow stage) covering the complete 5' end of ORF of *coffea canephora* CCoAOMT-L1 (SEQ ID NO:7) (see methods in examples). This sequence and the sequence of the insert contained in pcccs30w29k18 (SEQ ID NO:34) were used to design the primers CCoAOMT-L1-FullUp (SEQ ID NO:56) and CCoAOMT-L1FullLow (SEQ ID NO:57) to amplify a fragment from *Coffea arabica* T2308 (Grain, yellow stage) containing the complete ORF (CaCCoAOMT-L1 in pNT8) (SEQ ID NO:7). Symbols are the same as for FIGS. 2 and 3. B) The insert sequence of pNT8 (SEQ ID NO:7) was aligned with the cDNA sequences Race1_CcCCoAOMT-L1 (SEQ ID NO:33) and pcccs30w29k18 (SEQ ID NO:34) using the CLUSTALW and manually optimized. Bases marked in gray match the base most frequently found in that position.

Based on the sequence encoded by pcccs30w29k18 (SEQ ID NO:34), specific primers were devised to isolate the 5' end of the corresponding gene sequence using the well-established technique of 5' RACE PCR. Using the RACE PCR conditions described in Example 2 and Table 2 above, the gene specific primers 122801-GSP1 (SEQ ID NO:46) (first round RACE PCR) and 122801-GSP2 (SEQ ID NO:47) (second round RACE PCR), and cDNA prepared by Method 1 using RNA isolated from *C. canephora* BP409 grain at yellow stage of development produced a 218 base pair PCR fragment that was cloned in pCR4-TOPO according to the protocol described previously and sequenced. The resulting sequence (Race1_CcCCoAOMT-L1 in pNT13 (SEQ ID NO:33)) overlapped the 5' end of the cDNA clone pcccs30w29k18 (SEQ ID NO:34) (FIG. 9A: 61 bp of overlapping sequence). This newly isolated coffee 5' end CcCCoAOMT-LIKE sequence (Race1_CcCCoAOMT-L1 (SEQ ID NO:33)), and the partial coding sequence in the cDNA pcccs30w29k18 (SEQ ID NO:34), allowed the design of two new primers (CCoAOMT-L1-Fullup (SEQ ID NO:54) and CCoAOMT-L1-FullLow (SEQ ID NO:55), Tables 3 and 4) to specifically amplify the complete ORF sequence of the coffee CaCCoAOMT-L1 (SEQ ID NO:15) using cDNA made from RNA isolated from *C. arabica* (T2308) grain (yellow development stage) (Table 4).

Figure 9B:
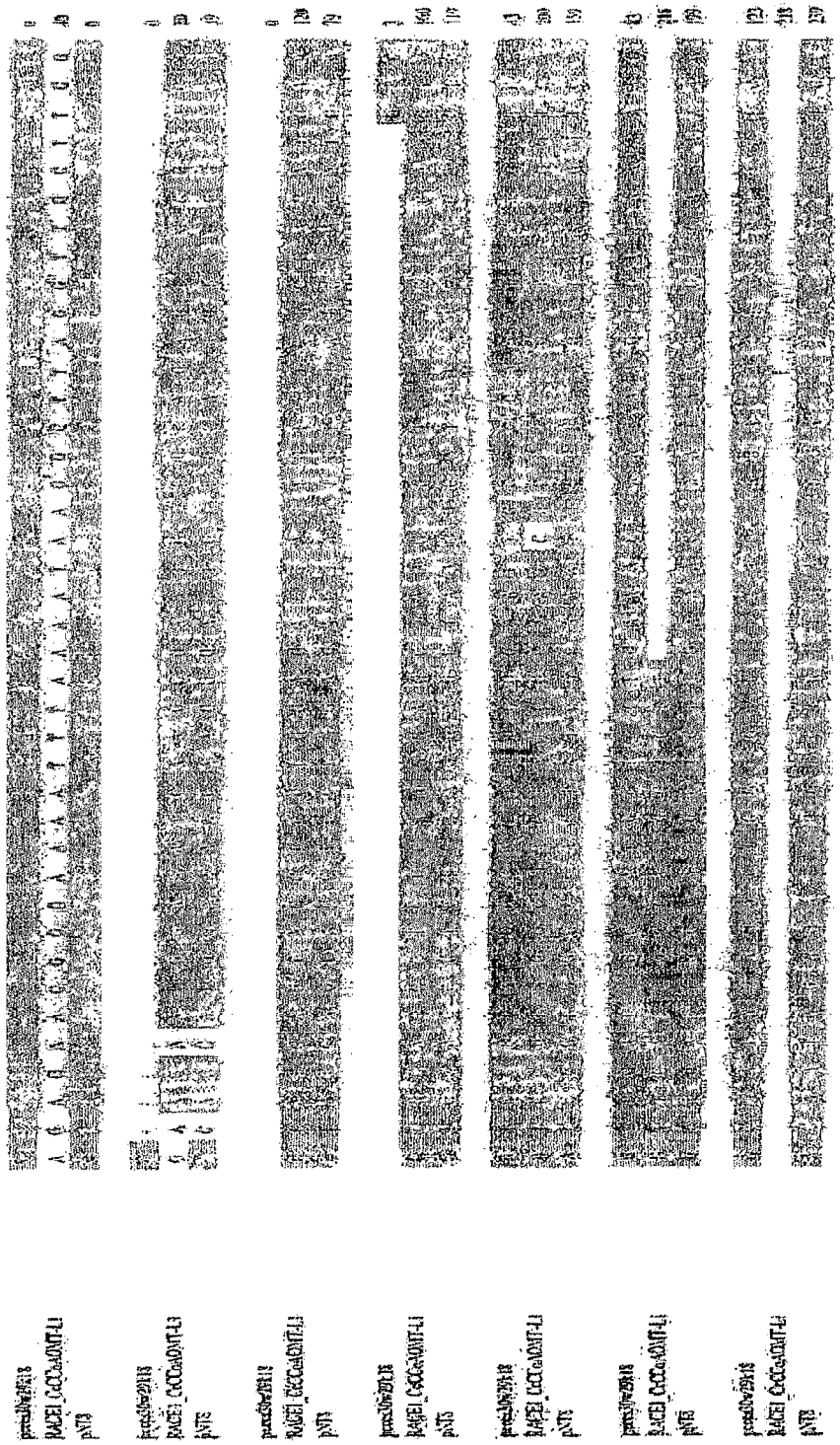
Figure 9B:
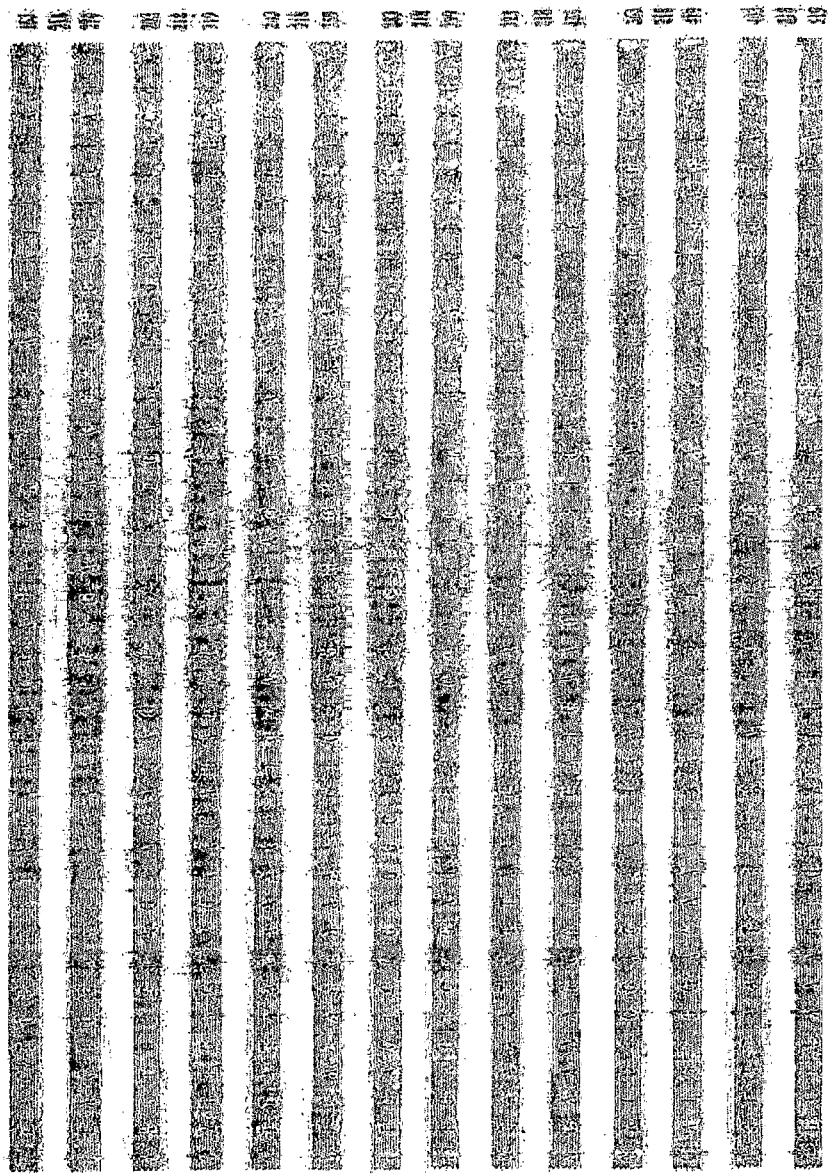
Figure 9B:
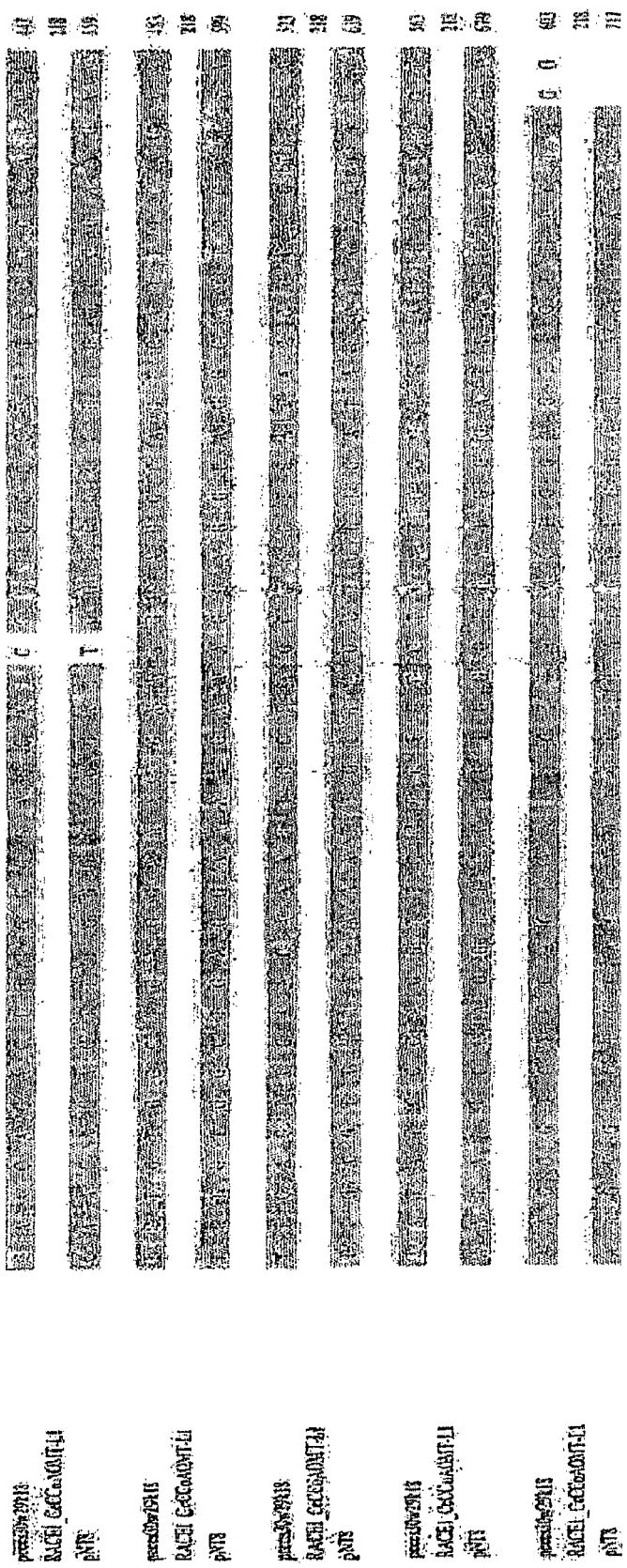

The PCR amplification was carried out in a final 50 µl volume, as follows: 5 µl of cDNA, 5 µL 10×PCR buffer (cloned Pfu Reaction Buffer), 400 nM of both specific primers, 200 µM each dNTP, and 1.25 U of Pfu Turbo DNA polymerase (Stratagene). The PCR cycling conditions were as follows: 94° C. for 2 min; then 40 cycles of 94° C. for 1 min, annealing temperature 55° C. for 1 min, and 72° C. for 2 min. An additional final step of elongation was done at 72° C. for 7 min. This PCR resulted in the generation of a cDNA fragment that was directly cloned in pENTR/D-TOPO vector to form the plasmid pNT8 (FIG. 9B). Sequence analysis of the pNT8 insert (SEQ ID NO:7) indicated that this cDNA was 717 bp long (including the CACC sequence used in cloning). The plasmid pNt8 has a complete ORF of 690 bp encoding a polypeptide (SEQ ID NO:15) of 229 amino acids having an estimated molecular weight of 25.71 kDa.

Figure 11:
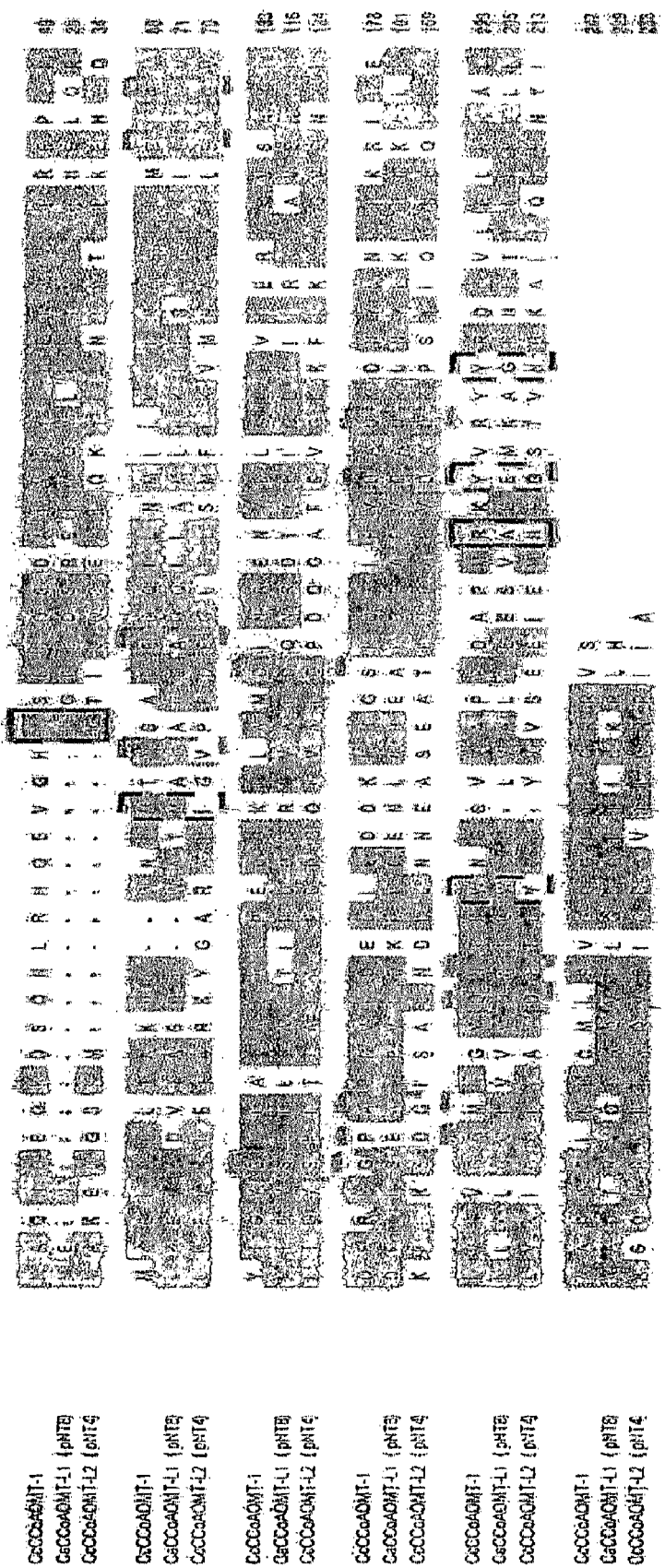
FIG. 11. Protein sequence alignment of CcCCoAOMT-1 (pcccl15a11), CaCCoAOMT-L1 (pNT8), and CcCCoAOMT-L2 (pNT4). An alignment of protein sequences CcCCoAOMT-1, CaCCoAOMT-L1 and CcCCoAOMT-L2 (SEQ ID NOs:14, 15, 16, respectively) encoded by (SEQ ID NOs: 6, 7, 8, respectively) was done using CLUSTALW and manually optimized. Amino acids marked in gray match the residue most frequently found in that position. The following amino acid interactions were characterized in the recent crystal structure of the alfalfa (*Medicago sativa*) CCoAOMT complexed with reaction products (Ferrer et al, 2005): the pink boxes indicate amino acids which interact with the negatively charged 3'-phosphate group of the adenosine 3'-5' diphosphate moiety of CoA, the blue boxes indicate amino acids involved in substrate recognition, and the green boxes indicate amino acids involved in divalent metal ion and cofactor binding.

The alignment presented in FIG. 11 confirms that the ORF of CaCCoAOMT-L1 (pNT8) in not an allele of CcCCoAOMT-1 but is clearly a different gene product. Effectively, the CaCCoAOMT-L1 protein sequence (SEQ ID NO:15) encoded by ORF contained in pNT8 (SEQ ID NO:7) (54.6% identity CcCCoAOMT-1). In addition, this proteins shows only 54.2%, 57.8% and 57.4% identity with characterized MsCCoAOMT, NtCCoAOMT and VvCCoAOMT proteins (Genbank Accession numbers are respectively AAC28973 (SEQ ID NO:37), AAC49913 (SEQ ID NO:38), and CAA90969 (SEQ ID NO:39), see FIG. 12). As shown in FIG. 12, five of the characterized sites described in the crystal structure of the alfalfa CCoAOMT are different in the *coffea* protein sequence CCoAOMT-L1. Two of twelve conserved amino acids that have been determined be implied in the cofactor's binding (Ferrer et al. 2005): i.e., Glu67 and Pro139 of MsCCoAOMT are replaced respectively by a Ala and a Glu residues in CaCCoAOMT-L1 (SEQ ID NO:15), and three of six residues involved in substrate recognition (Ferrer et al. 2005): i.e., Arg206, Tyr208 and Tyr212 are replaced in CaCCoAOMT-L1 (SEQ ID NO:15) protein by an Ala, a Glu, and a Gly residue, respectively.

The longest cDNA representing the 5' end of the unigene #119560 (cccs46w30m24), and potentially encoding a partial ORF of this protein, was then isolated from the 46 weeks grain library (46 weeks after flowering) and fully sequenced. Sequence analysis showed this cDNA (SEQ ID NO:36) encoded a 934 bp insert. An alignment of the DNA sequence of this insert with the well characterized NtCCoAOMT and MsCCoAOMT (Genbank Accession numbers AAC49913 (SEQ ID NO:38) and AAC28973 (SEQ ID NO:37), respectively) protein sequences using CLUSTALW indicates this cDNA probably contains an intron. The optimized alignment of the NtCCoAOMT and MsCCoAOMT DNA sequences with insert of pcccs46w30m24 by the CLUSTALW program produced an insertion of 72 bp within the ORF DNA sequences of the other characterized plant cDNA sequences compared to the sequence of the pcccs46w30m24 insert. Additionally, the ORF of cccs46w30m24 insert encoded a truncated protein sequence 92 amino acids shorter than the NtCCoAOMT and MsCCoAOMT at the C-terminus due to a stop codon within the proposed intron sequence of pcccs46w30m24.

Based on the observation that pcccs46w30m24 cDNA sequence (SEQ ID NO:36) contains an intron, a processed sequence was generated in silico. The splice processing was carried out at bp 426 to 497, which represented the hypothetical intron. Sequence analysis of the resulting spliced 862 bp sequence (pcccs46w30m24 sequence minus hypothetical intron) revealed that this cDNA contained a 702 bp ORF, encoding a partial protein of 233 amino acids, This hypothetical polypeptide sequence was then aligned with the NtCCoAOMT and MsCCoAOMT protein sequences described in the previous section (FIG. 12), revealing that the partial ORF of pcccs46w30m24 shares 48.9% identity with each of these CCoAOMT sequences. This protein associated with this partial ORF was called CcCCoAOMT-L2 (SEQ ID NO:16).

Figure 10A:
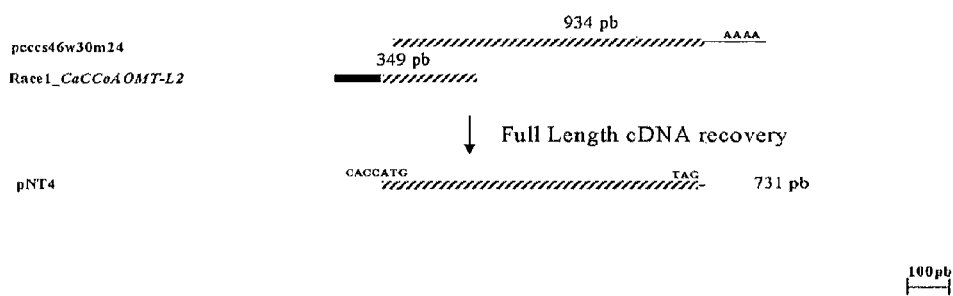
FIG. 10. Isolation and characterization of the complete ORF for CcCCoAOMT-L2 (pNT4) from *coffea canephora*. A) Isolation of a cDNA containing the complete ORF (SEQ ID NO:8) for CCoAOMT-L2 from *C. canephora*. One cDNA fragment (Race1_CaCCoAOMT-L2) (SEQ ID NO:35) was obtained from *Coffea arabica* (Grain, yellow stage) covering the complete 5' end of ORF of *Coffea arabica* CCoAOMT-L2 (SEQ ID NO:8) (see methods in examples). This sequence and the sequence of the insert contained in pcccs46w30m24 (SEQ ID NO:36) were used to design the primers CCoAOMT-L2-FullUp (SEQ ID NO:58) and CCoAOMT-L2-FullLow (SEQ ID NO:59), and these primers were used to amplify a fragment from *Coffea canephora* BP409 (Grain, yellow stage) called CcCCoAOMT-L2 (pNT4) (SEQ ID NO:8). The symbols are the same as for FIGS. 2 and 3. B) The insert sequence (SEQ ID NO:8) of pNT4 was aligned with the cDNA sequences Race1_CaCCoAOMT-L2 (SEQ ID NO:35) and pcccs46w30m24 (SEQ ID NO:36). The alignment was done using the CLUSTALW and manually optimized. Bases in grey match the residue most frequently found for that position.

However, as pcccs46w30m24 (SEQ ID NO:36) encodes a significant part of a predicted *coffea* CCoAOMT-LIKE sequence, this enabled the design of specific primers to isolate the missing 5' end coding sequence of this gene. With cDNA prepared by Method 1 using RNA isolated from *C. arabica* (T-2308) grain at yellow stage, the primers 119560-GSP1 (SEQ ID NO:48) (First round RACE PCR) and 119560-GSP2 (SEQ ID NO:49) (Second round RACE PCR) and the PCR conditions noted in Example 2 and in Table 2, a unique fragment was obtained. This fragment was directly cloned into the pCR4-TOPO vector to give pNT14 and sequenced using the T3 universal primer. The resulting insert sequence (Race1_CaCCoAOMT-L2 (SEQ ID NO:35)) was 349 bp long and, as expected, overlapped the 5' end of the sequence in pcccs46w30m24 (SEQ ID NO:36) (FIG. 10A, with 224 bp of overlapping sequence). This newly isolated *C. arabica* 5' end CCoAOMT-LIKE sequence (Race1_CaCCoAOMT-L2) (SEQ ID NO:35), and the coding sequence in the cDNA pcccs46w30m24 (SEQ ID NO:36), allowed the design of two new primers CCoAOMT-L2-FullUp (SEQ ID NO:58) and CCoAOMT-L2-FullLow (SEQ ID NO:59) (Tables 3 and 4) capable of specifically amplifying the complete ORF sequence of CCoAOMT-L2 (SEQ ID NO:8).

Figure 10B:
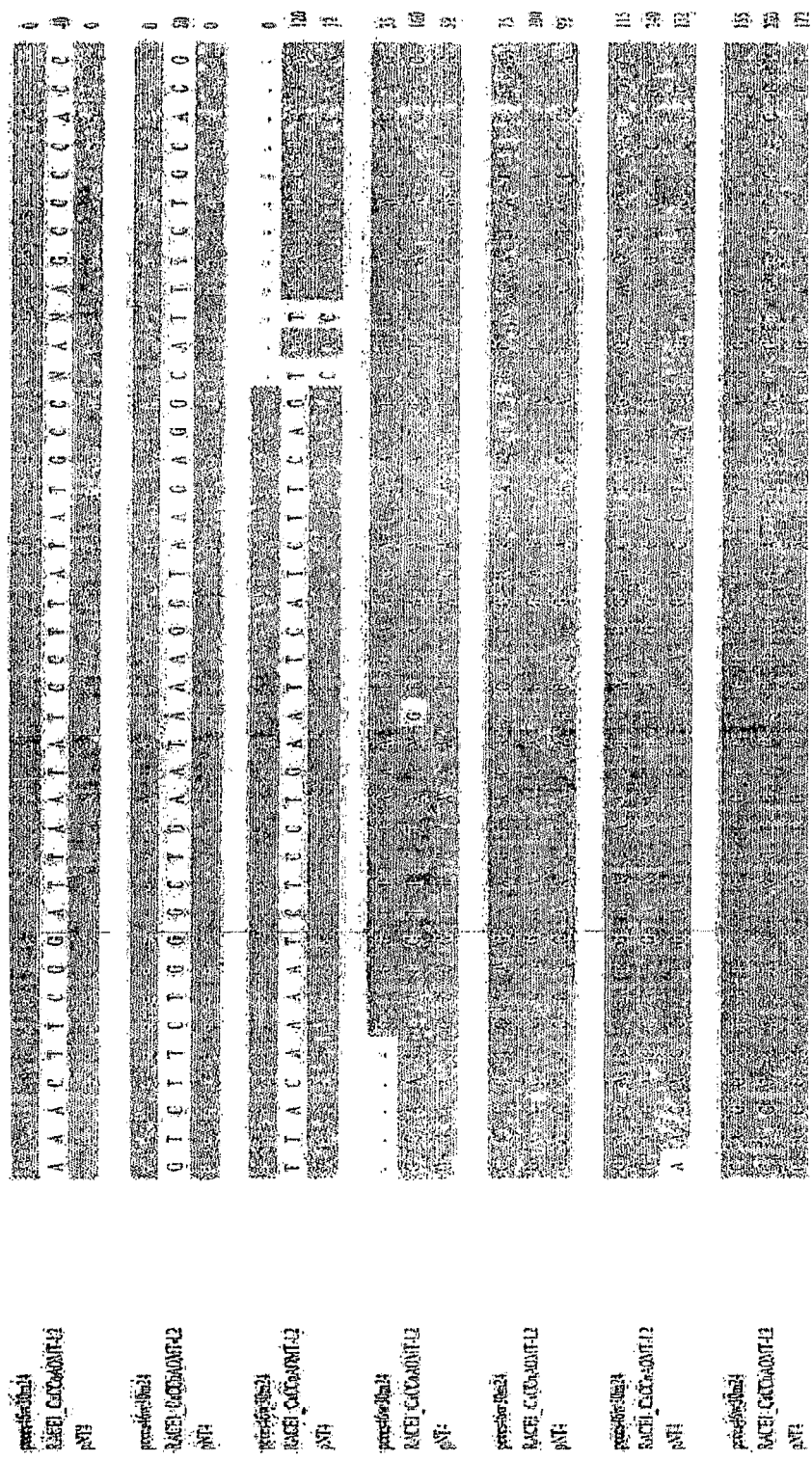

The cDNA used for this experiment to amplify the complete ORF of CCoAMT-L2 was generated by Method 1 using RNA isolated from *C. canephora* (BP-409) grain at yellow stage of development (same cDNA used to make the full length cDNA for HCT, see Table 4). As described in Example 2, the experiment was carried out using Takara LA Taq DNA polymerase (in a final 50 µl volume, as follows: 5 µl of cDNA (Table 4), 5 µL 10×PCR buffer (LA PCR II Mg2+), 800 nM of both specific primers, 200 µM each dNTP, and 0.5 U of Takara LA Taq DNA polymerase (Cambrex Bio Science). The PCR cycling conditions were the same as described in Example 2. This experiment generated a single major PCR product that was directly cloned into the pCR4-TOPO vector as described previously resulting in the plasmid pNT4 (See FIG. 10B for DNA sequence). pNT4 (SEQ ID NO:8) encodes a complete ORF of 717 bp which encodes a polypeptide (SEQ ID NO:16) of 238 amino acids with an estimated molecular weight of 26.30 kDa.

Alignment of complete ORF of the *coffea* CCoAOMT-L2 sequence with the previously characterized *Medicago sativa, Nicotiana tabacum* and *Vitis vinifera* CCoAOMT sequences (noted above) confirms the initial annotation of pcccs46w30m24 (SEQ ID NO:36) partial *coffea* sequence using BLAST as coffee CCoAOMT-LIKE protein (FIG. 12). At the protein level, the coffee CcCCoAOMT-L2 (pNT4) ORF sequence exhibits 46.6% identity with the MsC-CoAOMT, 47% identity with the NtCCoAOMT-1 and 47.8 identity with the VvCCoAOMT protein sequence. The alignment presented in FIG. 11 between the *coffea* CcCoAOMT-L2 sequence (SEQ ID NO:16) and the *coffea* CaCCoAOMT-L1 protein sequence (SEQ ID NO:15) described above and CcCCoAOMT-1 (SEQ ID NO:14) clearly shows that these three protein sequences represent different highly related groups of proteins.

A second alignment performed with all three proteins (ie. the coffee CCoAOMT (SEQ ID NO:14) and the two CCoAOMT-LIKE proteins (SEQ ID NOs:15 and 16)) with the well characterized CCoAOMT proteins in FIG. 12 clearly illustrates that the sequence of the *coffea* CcCCoAOMT-L2 protein (SEQ ID NO:16) is more distantly related to the well-characterized plant CCoAOMT proteins than to the CaCCoAOMT-L1 protein (SEQ ID NO:15). In addition, it is also noted in FIG. 12 that the CcCCoAOMT-L2 protein sequence (SEQ ID NO:16) has several amino acid changes in regions associated with substrate recognition (*Medicago sativa* accession number AAC28973 (SEQ ID NO:37), Ferrer et al., 2005).

EXAMPLE 9

Over-Expression and Characterization of CcCCoAOMT1

The Gateaway technology (Invitrogen) composed of the two vectors: pENTR/D-TOPO and the expression vector pDEST17, was used to over-produce the CcCCoAOMT1 protein (SEQ ID NO:14). The strategy consisted of transferring the ORF of CcCCoAOMT1 (SEQ ID NO:6) into the first vector (pENTR/D-TOPO) in frame with the HisTag sequence. Two specific primers were designed to accomplish this. The first primer (CCoAOMT1-Fullup (SEQ ID NO:54) Table 3) includes the specific sequence for the first few codons of the ORF (beginning with the start codon ATG) and the CACC adaptor necessary to direct cloning in pENTR/D-TOPO is 5' to the ATG codon. The second primer (CCoAOMT1-FullLow, (SEQ ID NO:55) Table 3) contains the stop codon of the ORF and several bases (14 bp) in the 3' UTR.

Then, a PCR reaction was performed with the specific primers described above and Pfu Turbo DNA polymerase (Statagene), which does not generate an adenine in 5' end of the product and allows the direct cloning of CcCCoAOMT1 PCR product into pENTR/D-TOPO. The PCR amplification was carried out in a final 50 µl volume, as follows: 5 µl of pcccl15a11 plasmid (1/50 diluted), 5 µL 10×PCR buffer (cloned Pfu Reaction Buffer), 400 nM of both specific primers, 200 µM each dNTP, and 1.25 U of Pfu Turbo DNA polymerase (Stratagene). The PCR cycling conditions were as follows: 94° C. for 2 min; then 40 cycles at 94° C. for 1 min, annealing temperature 55° C. for 1 min, and 72° C. for 2 min. An additional final step of elongation was done at 72° C. for 7 min. This experiment put the CcCCoAOMT1 ORF into the pENTR/D-TOPO vector to form the plasmid pNT15.

Then, pNT15 was recombined with pDEST17 (ampicillin resistance) according to the protocol GATEWAY suggested by the manufacturer (Invitrogen) to produce pNT16 in which the ORF is in frame in pDEST17. The products of the recombination were transformed into competent cells Top10 (Invitrogen) and clones that were ampicillin resistant. Positive clones were verified to contain the CCoAOMT1 insert by PCR screening with the specific primers CCoAOMT1-FullUp (SEQ ID NO:54) and CCoAOMT1-FullLow (SEQ ID NO:55) described in TABLE 3. After purification, pNT16 was then transformed in competent cells Bl21AI (for protein expression) according to the protocol suggested by the supplier (Invitrogen).

For protein expression, a pre-culture of the Bl12AI cells with pNT16 was grown over night at 37° C. in 5 ml of LB medium containing 100 µg/ml of ampicillin. 200 µl of each pre-culture served to inoculate two cultures (50 ml of LB medium with 100 µg/ml of ampicillin), and the cells were grown up to an $OD_{600nm}=0.6$. The expression of the cloned protein was then induced with 0.2% of L-arabinose and the culture was incubated for a further 6 h at 27° C. A negative control with repression (produced by making another control culture 0.1% glucose) was also carried out.

Then cells were pelleted, harvested and resuspended in two ml of lysis buffer (50 mM Potassium phosphate pH 7.8, 400 mM NaCl, 100 mM KCl, 20 mM β-mercaptoethanol, 10% Glycerol, 0.5% Triton X100, imidazole 10 mM). The lysis is carried out by three cycles of freeze/thaw (−180° C./42° C.) and followed by 3 cycles of sonication (1 minute treatment/one minute cooling) on ice with the power setting of the inserted probe being used at 40% maximum (Vibra-Cell72412, BIOBLOCK Scientific). The lysed cells were then centrifuged (30 min 10,000 g), and the supernatant was incubated with Ni-Nta beads (Qiagen product 1004494) for 1 hour and then the whole mixture was transferred to a chromatography column (Invitrogen # cat number). This column was then washed two times with 4 ml of washing buffer (50 mM Tris HCl pH 7.5, 500 mM NaCL, 20 mM imidazole, 20 mM β-mercaptoethanol, 10% Glycerol, 0.2 mM $MgCl_2$). The his-tagged protein was eluted with five fractions of 0.5 ml of elution buffer ((50 mM Tris HCl pH 7.5, 500 mM NaCL, 0.2 mM $MgCl_2$, 20 mM β-mercaptoethanol, 10% Glycerol, 250 mM imidazole).

Figures 15A, 15B:
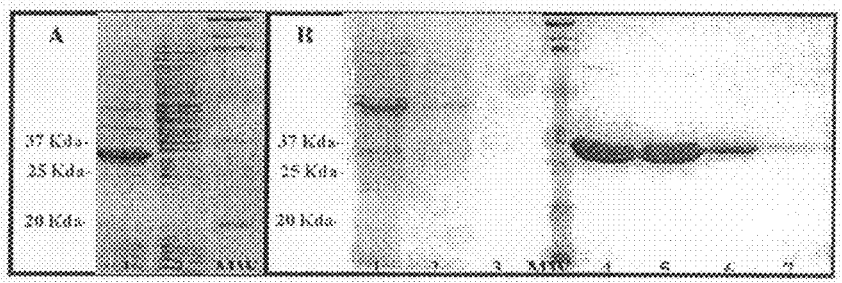
FIG. 15. Analysis of CcCCoAOMT-1 (pNT16) expression and purification. A) The expression of the His-Tag- CcCCoAOMT1 fusion protein was analyzed on a 12% SDS-PAGE gel and stained with coomassie blue. A-Lanes 1. Crude extract of Bl21 recombinant cells containing pNT16 and with expression induction using 0.2% d'arabinose, 2. Crude extract of Bl21 recombinant cells with pNT16 and with expression suppression using 0.1% of glucose. B-Lanes 1. lysate loaded on NiNTA column, 2. First wash fraction: 3. second wash fraction, 4 to 7. fractions 1-4 eluted from the NiNTA column using elution buffer. MW: Molecular weight marker (Precision Plus Prestained All Blue (Biorad #161-0373)).

After pooling the fractions containing protein, this pool was dialysed against the activity buffer (50 mM Tris HCl pH 7.5, 500 mM NaCL, 0.2 mM $MgCl_2$, 20 mM β-mercaptoethanol, 10% Glycerol). The purification of the protein was verified by an analysis on a 12% SDS-PAGE gel (FIG. 15). The induction of recombinant cells caused the accumulation of a large quantity of recombinant protein, with an estimated molecular weight of 30 Kda (FIG. 15A), which corresponds to predicted size of the CcCCoAOMT1 His-Tagged protein. The His-Tagged recombinant protein was mainly found in the first three eluded fractions and the absence of any other significant bands in these eluted fraction show that there is little contamination with non-specific protein, and the gel analysis also demonstrates the absence of recombinant protein degradation (FIG. 15B). This experiment shows that the HisTag chromatography allowed the isolation of a large quantity of His-Tagged CcCCoAOMT1 protein.

Protein quantification was performed using the Bradford standard protocol (Bradford Sigma kit #B6916).

The assay of CcCCoAOMT1 was performed by a protocol related to those used by Inoue et al. 1998. The assay was carried out in a final volume of 200 µL of activity buffer (50 mM Tris HCl pH 7.5, 500 mM NaCL, 0.2 mM $MgCl_2$, 20 mM β-mercaptoethanol, 10% Glycerol) containing 40 µg of protein, 150 µM of SAM and 200 µM of caffeic acid. The reactions were carried out at 30° C., and at indicated times the reaction was stop by adding 9 volumes of stop buffer (0.1% (v/v) formic acid, 5% (v/v) acetonitrile, pH 2.5). These samples were then clarified on 0.22 µM filters and 20 µL of this was injected on the HPLC.

The HPLC analysis was run as follows: column (Machery Nagel Nucleosil 5 C18, 8 µm, 4×250 mm); gradient elution, solvent A (0.1% (v/v) formic acid) and solvent B (5% (v/v)-Acetonitrile): 0-15 min 5% B-50% B, 15-17 min 50% B-70% B, 17-23 min 70% B, 23-25 min 70% B-100% B, 25-30 min 100% B, 30-32 min 100% B-5% B, 32-40 min 5% B, flow rate, 1 mL/min and detection by UV spectrophotometer at 324 nm (Waters 2487).

Figure 18:
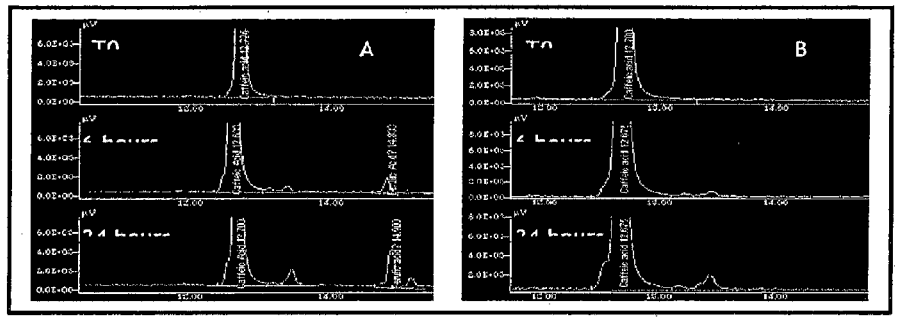
FIG. 18. Activity analysis for the HisTag-CcCCoAOMT1 recombinant protein. Samples of the activity reactions described in the method section were loaded on a HPLC column and the elution profile was measured at 324 nm Panel A HPLC elution profile of reaction samples containing 40 µg of recombinant protein taken at 0, 6, and 24 hours respectively. Panel B HPLC profile of control reaction without enzyme added at the same time points.
Figure 19:
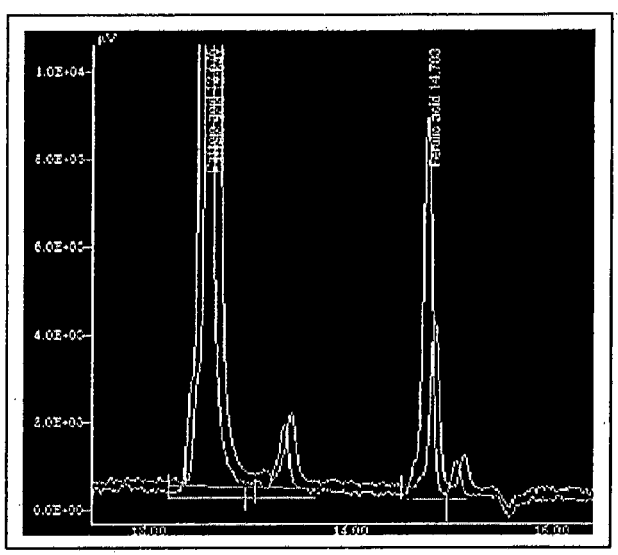
FIG. 19. Identification of the unknown product of the CcCCoAOMT1 protein as ferulic acid. The peak at 14.8 min retention time was identified as ferulic acid by adding a ferulic acid "spike" directly into the 24 hour enzyme sample illustrated in FIG. 18 panel A. The UV absorbance at 324 nm of the 24 hour sample + and – "spike" is presented. The green curve represents the elution profile of the 24 h sample, and the yellow curve represents the elution profile of the 24 hour sample plus the ferulic acid "spike": the unknown product clearly co-elutes with the ferulic acid "spike".

The CcCCoAOMT1 enzyme assay was not carried out with Caffeoyl CoA, the preferred substrate of the enzyme, because this substrate is not available commercially. Instead, caffeic acid, a compound previously used for the *Medicago sativati* recombinant protein, CCoAOMT was used as the substrate. Caffeic acid has a lower specificity. (Inoue et al. 1998; Parvathi et al. 2001) In this assay, the expected product of reaction is the ferulic acid. The comparison of HPLC analysis spectrums from the control and the test reactions are shown in FIGS. 18 A and B. The results obtained demonstrate that a new peak appears at 14.8 min after 6 hours, and this peak is larger at 24 hours. This retention time is identical to a ferulic acid standard. In addition, when the sample was spiked with ferulic acid, the newly added ferulic acid coeluted with the proposed peak of ferulic acid (FIG. 19), confirming the proposal that this CcCCoAOMT1 generated peak is ferulic acid. A second peak can be identified at the retention time of 15.2 min, and because this peak is not in the control sample (no enzyme), it could be either another product generated by CcCCoAOMT1, or a degradation product of ferulic acid. Overall, the data of FIG. 18 demonstrate that the protein encoded by CcCCoAOMT1 has one of the predicted enzymatic activities associated with CcCCoAOMT proteins like MsCCoAOMT and thus CcCCoAOMT1 encodes a coffee caffeoyl CoA O-methyl transferase protein.

EXAMPLE 10

Over-Expression of CaCCoAOMT-L1 and CcCCoAOMT-L2 Proteins

Figures 16A, 16B:
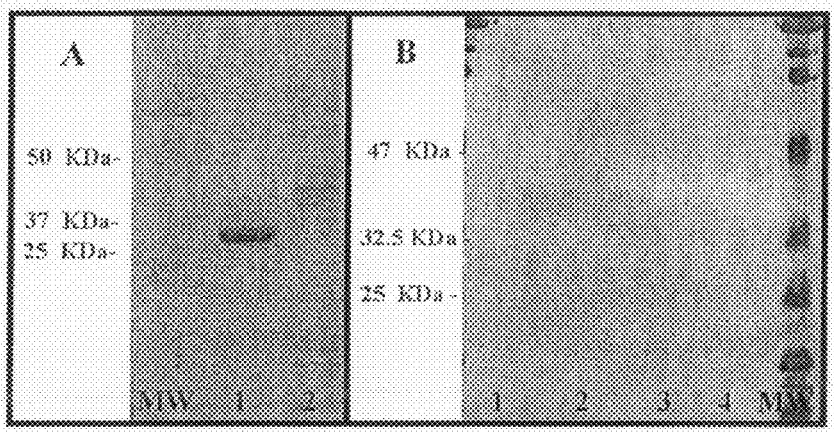
FIG. 16. Analysis of CaCCoAOMT-L1 (pNT12) expression and purification. A) The expression of the His-Tag-CaCCoAOMT-L1 fusion protein was analyzed on a 12% SDS-PAGE gel and stained with coomassie blue. A-Lanes 1. Crude extract of Bl21 recombinant cells containing pNT12 and with expression induction using 0.2% d'arabinose, 2. Crude extract of Bl21 recombinant cells with pNT12 and with expression suppression using 0.1% of glucose MW: Molecular weight marker (Precision Plus Prestained All Blue (Biorad #161-0373)). B-Lanes 1-4 fractions 1-4 eluted from the NiNTA column using elution buffer. MW: Molecular weight marker (Unstained Precision Broad Range (Biorad #161-0362)).

The ORF (SEQ ID NO:7) corresponding to CaCCoAOMT-L1 protein (SEQ ID NO:15) was already present in the entry vector pENTR/D-TOPO (ie. pNT8). In order to over express the CaCCoAOMT-L1 protein (SEQ ID NO:15), this ORF was transferred into pDEST17 as described above for CcCCoAOMT1 (SEQ ID NO:14), yielding the plasmid pNT12. This plasmid was then transformed into BL21-AI cells and the protein was overexpressed and purified as described for CcCCoAOMT1, except that the induction of expression with arabinose was carried out over night at 20° C. FIG. 16 shows the results of this over-expression purification experiment. Panel A (FIG. 16) demonstrates that a good induction of a protein with the approximate expected size (approximately 26 kDa) occurred on induction of the transformed cells. The purification results show that while CaCCoAOMT-L1 is relatively overexpressed, the purification on the HisTag column was not very efficient (FIG. 16, Panel B). It is believed that much of the protein produced was insoluble and this protein would have been lost after the centrifugation step.

Figures 17A, 17B:
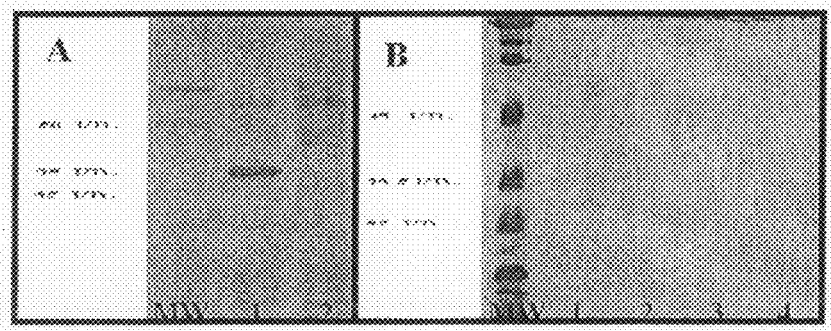
FIG. 17. Analysis of CcCCoAOMT-L2 (pNT17) expression and purification. A) The expression of the His-Tag-CcCCoAOMT-L2 fusion protein was analyzed on a 12% SDS-PAGE gel and stained with coomassie blue. A-Lanes 1. Crude extract of Bl21 recombinant cells containing pNT17 and with expression induction using 0.2% d'arabinose, 2. Crude extract of Bl21 recombinant cells with pNT17 and with expression suppression using 0.1% of glucose, MW: Molecular weight marker (Precision Plus Prestained All Blue (Biorad #161-0373)). B-Lanes 1-4 fractions 1-4 eluted from the NiNTA column using elution buffer. MW: Molecular weight marker (Unstained Precision Broad Range (Biorad #161-0362)).

To overexpress the CcCCoAOMT-L2 protein (SEQ ID NO:16), two primers CCoAOMT-L2-FullUp (SEQ ID NO:58) and CCoAOMT-L2-FullLow (SEQ ID NO:59) (Table 3) were designed to amplify the ORE corresponding to CcCCoAOMT-L2 from the plasmid pNT4. These primers generated a PCR fragment that could be cloned into pENTR/D-TOPO using the same strategy as described for CcCCoAOMT1. The conditions of the PCR using Pfu Turbo DNA polymerase were also the same as for CcCCoAOMT1, and generated pNT10. In order to over express the CcCCoAOMT-L2 protein, the ORF contained in pNT10 was transferred into pDEST17 as described above for CcCCoAOMT1, yielding the plasmid pNT17. This plasmid was then transformed into BL21-AI cells and the protein was overexpressed and purified as described for CcCCoAOMT1 except that the induction of expression with arabinose was carried out over night at 20° C. FIG. 17 shows the results of this over-expression purification experiment. Panel A (FIG. 16) demonstrates that a good induction of a protein with the approximate size expected (approximately 28 kDa) occurred on induction of the transformed cells. The purification results show that while CcCCoAOMT-L2 is relatively overexpressed, the purification on the HisTag column was not very efficient. It is believed that much of the CcCCoAOMT-L2 protein produced was insoluble and thus this protein would have been lost after the centrifugation step.

EXAMPLE 11

Over-Expression and Purification of HCT and HQT Proteins

In order to demonstrate that the proteins encoded by pML1 (CcHCT (SEQ ID NO:1)) and pML2 (CcHQT (SEQ ID NO:3)) could be produced in recombinant forms, these proteins were over-expressed in *E. coli* This was carried out by amplifying each ORF by PCR amplification using the primers noted in Table 7. The 5' end PCR primer had a BamH1 site just before the ATG start codon and the 3' end primer had an Xba1 site just after the stop codon. The PCR reactions were performed with the Phusion Polymerase (FinnZymes) under the conditions specified by the manufacturer. The specific PCR products thus generated were purified on agarose gels and then isolated from the gels using the GeneClean Turbo kit (Q-biogene) according to the manufacturer's protocol. The purified fragments were then digested with BamHI and XbaI restriction enzymes (New England Biolabs).

The expression vector (plasmid pGTPc103a) was also digested with BamHI and XbaI under the same conditions. The gel purified fragments were quantified and then ligated into the digested pGTPc103a vector using T4 DNALigase (New Englands Biolabs), a step which was designed (via the PCR primers used) to put the GST tag encoded by the vector in-frame with the HCT/HQT protein sequence being cloned. DH5a competent cells (Invitrogen) were then transformed with each ligation mixture according the manufacturers protocol. Screening of colonies for those with the appropriate inserts was performed by PCR using the same primers employed to clone the ORE and with enzymatic digestion. Selected plasmids were then purified and the HCT and HQT inserts present were sequenced (to ensure no error during the PCR step). The pGTPc103a plasmid containing the CcHCT sequence was named pGTPc103a_HCT and the pGTPc103a plasmid containing the CcHQT sequence was named pGTPc103a_HQT. Finally, expression competent cells Bl21 (DE3) were transformed with pGTPc103a_HCT or pGTPc103a_HQT in order to over express protein.

In order to over-express the proteins, a pre-culture of each recombinant Bl21 (DE3) cells containing either CcHCT or CcHQT was grown over night at 37° C. in 10 ml of LB medium containing 50 µg/ml of kanamycin. Each pre-culture was then used to inoculate two larger cultures (200 ml of LB medium with 50 µg/ml of kanamycin), and the cells were grown until the OD 600 reached 1. Protein expression was then induced by adding 0.2 mM of IPTG and the cultures were then grown for a further 3 h at 37° C.

After this induction treatment, the cells were pelleted, and then resuspended in 25 ml of lysis buffer (20 mM NaPO4 pH 7.3, 150 mM NaCl, 1% Triton X100, 2 mM EDTA, 0.1% β-mercaptoethanol, 1× protease inhibitor mix). Lysis was carried out by sonication (Vibracel 72.434) on ice during 3 cycles of 10 seconds. The lysed cells were centrifuged (30 min 10,000 g), and the supernatant was applied to a sample of GST-Sepharose 4B media (Amersham) for 2 hour. This mixture was then transferred to a small chromatography column, and washed 3 times with 5 ml of washing buffer (420 mM NaPO4 pH 7.3, 150 mM NaCL, 1× protease inhibitor mix). The GST-tagged protein was eluted in four distinct fractions of 0.5 ml elution buffer (50 mM Tris HCl pH 8, 10 mM reduce gluthatione, 10% glycerol, 1× protease inhibitor mix). The production of the recombinant proteins and purifications of each fraction were followed by analysis on 5-18% SDS-PAGE gradient gel and by western blotting using a specific antibody against the GST Tag (FIGS. 13 and 14).

Figures 13A, 13B:
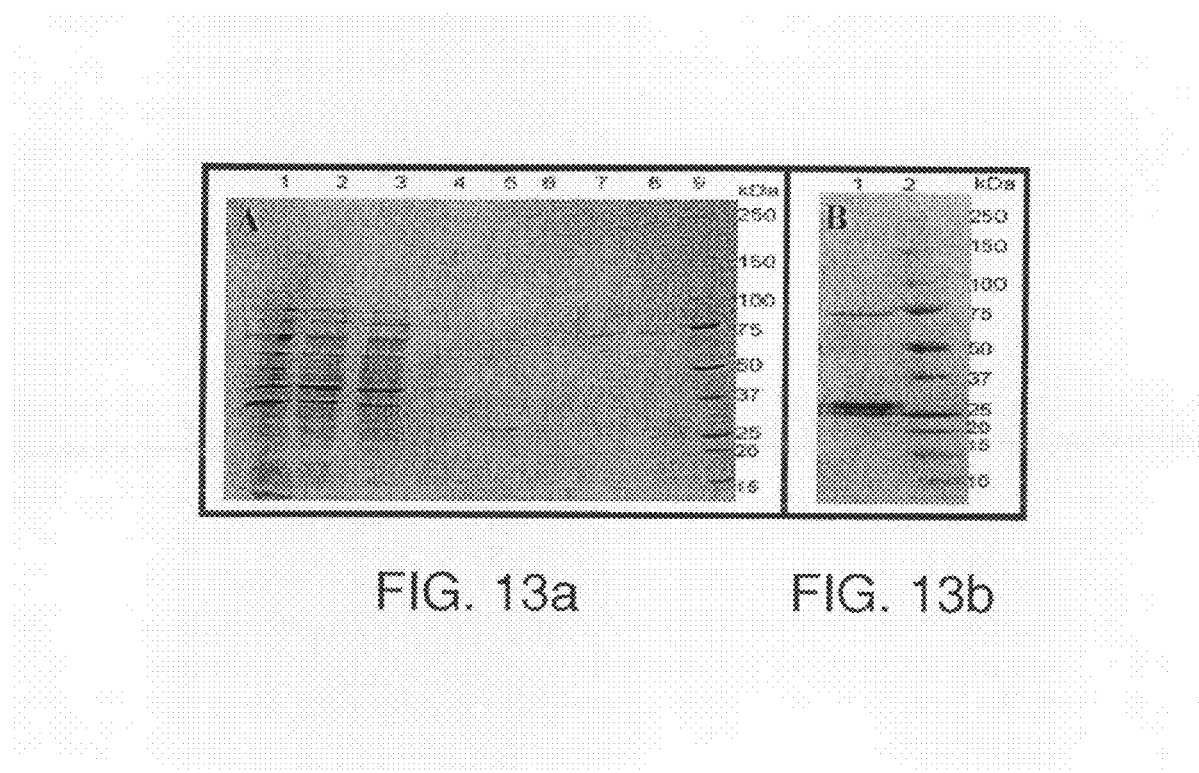
FIG. 13. Expression and purification of the recombinant CcHCT protein. A) Extracts from various stages of the expression and purification of the recombinant GST-CcHCT fusion protein (pGTPc103a_HCT) were analyzed by, A) using 5-18% SDS-PAGE and coomassie blue staining and by B) using western blotting analysis (see methods in examples). Lanes in A; 1. Total lysate of Bl21 recombinant cells containing pGTPc103a_HCT and induced with 0.2 mM IPTG 2. Soluble fraction lysate, 3. Insoluble fraction of lysate, 4. First wash of NiNTA column with wash buffer, 5 to 9 successive fractions eluted from the Ni-NTA column using elution buffer, 9 Weight ladder. Lanes in B; 1. Pooled material eluted from the Ni-NTA column. 2. Weight ladder.
Figures 14A, 14B:
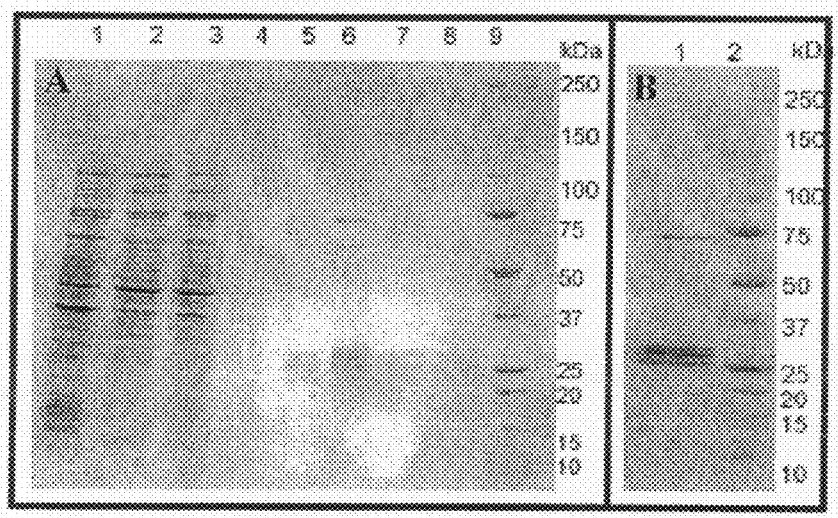
FIG. 14. Expression and purification of the recombinant CcHQT protein. A) Extracts from various stages of the expression and purification of the recombinant GST-CcHQT fusion protein (pGTPc103a_HQT) were analyzed by, A) using 5-18% SDS-PAGE and coomassie blue staining and by B) using western blotting analysis (see methods in examples). Lanes in A; 1. Total lysate of Bl21 recombinant cells containing pGTPc103a_HQT and inducted with 0.2 mM IPTG 2. Soluble fraction lysate, 3. Insoluble fraction of lysate, 4. First wash of NiNTA column with wash buffer, 5 to 9 successive fractions eluted from the Ni-NTA column using elution buffer, 9 Weight ladder. Lanes in B; 1. Pooled material eluted from the Ni-NTA column. 2. Weight ladder.

The results presented in FIG. 13A show that HCT was weakly over-expressed and that this protein could be purified by GST-Tag chromatography. The purified protein preparation (eluted over four fractions) contained two bands in the higher molecular weight range (72.2 and 70 kDa). The 72.2 kDa protein has the closest size to the size expected for the GST-HCT fusion. The 70 kDa protein is not known. The low molecular weight material (approx 28 kDa) corresponds to the GST tag alone. The Western blotting results presented in FIG. 13B demonstrate the 72.2 kDa protein reacts with the antibody against the GST tag as expected for the GST-HCT fusion protein. Similarly, the band at 28 kDa reacts strongly with the antibody against GST, confirming it is the GST protein. The results presented in FIG. 14A show that HQT was weakly over-expressed and that this protein could be purified by GST-Tag chromatography. The purified protein preparation (eluted over first two fractions) contained two bands in the higher molecular weight range (73.1 and 70 kDa). The 73.1 kDa protein the approximate size expected for the GST-HQT fusion. The 70 kDa protein is not known. The low molecular weight material (approx 28 kDa) corresponds to the GST tag alone. The Western blotting results presented in FIG. 14B demonstrate the 73.1 kDa protein reacts with the antibody against the GST tag as expected for the GST-HCT fusion protein. Similarly, the band at 28 kDa reacts strongly with the antibody against GST, confirming it is the GST protein.

TABLE 7

List of specific primers used for the sub-cloning of CcHCT and CcHQT into the plasmid pGTPc103a.

| Gene | Gene Specific primer | Primer sequence | Sequence Identifier No. |
|---|---|---|---|
| CcHCT | 178-HCT-S | 5' TTAATTAATTCGCGGATCCAT GAAAATCGAGGTGAAGGA 3' | 87 |
| | 178-HCT-R | 5' TATATATACTAGTCTAGATCA AATGTCATACAAGAAACTCTGG A 3' | 88 |
| CcHQT | 178-HQT-S | 5' TTTAAATTTCGCGGATCCATG AAGATAACCGTGAAGGAA 3' | 89 |
| | 178-HQT-R | 5' TATATATACTAGTCTAGATCA GAAATCGTACAGGAACCT 3' | 90 |

EXAMPLE 12

Figure 8:
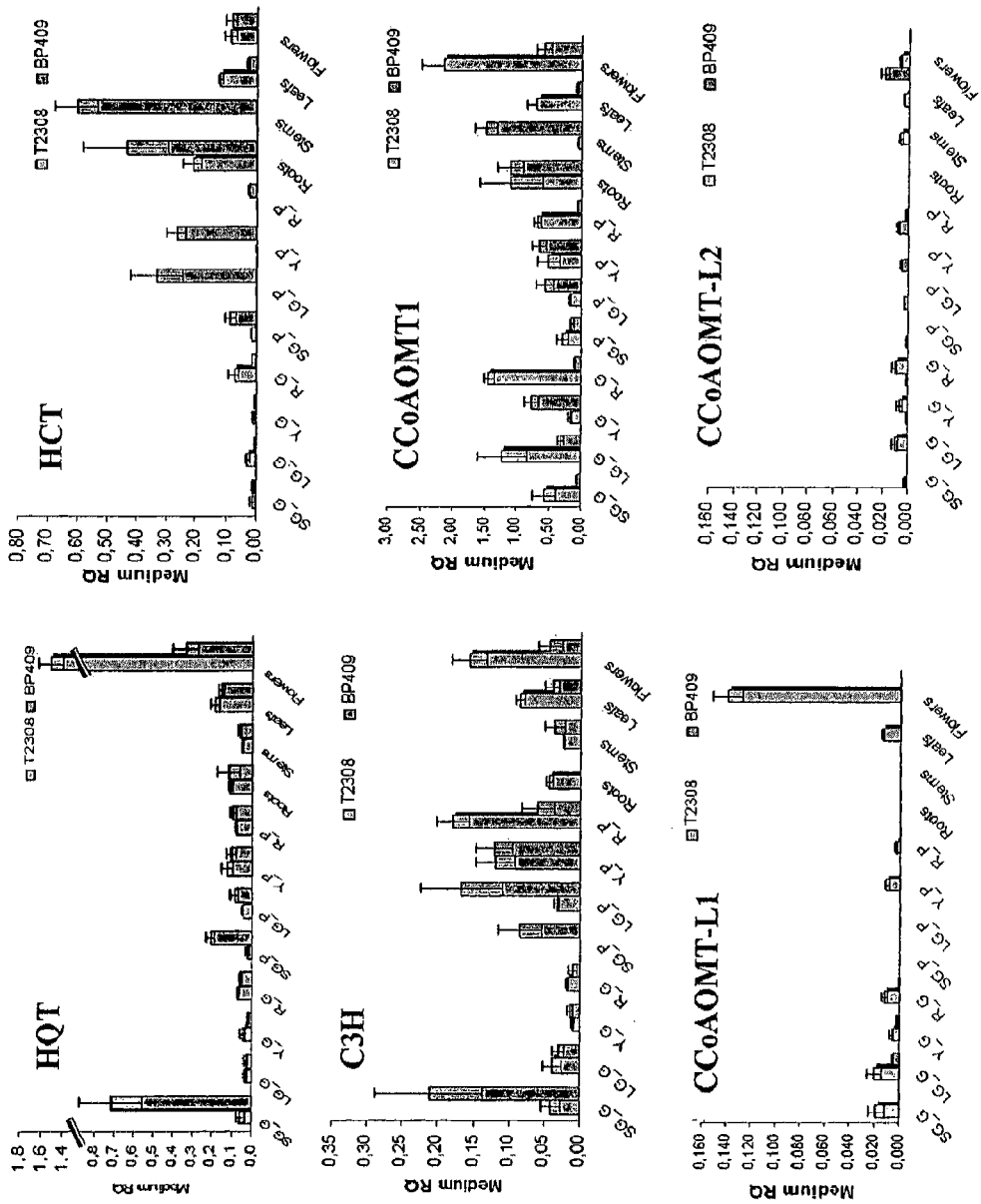
FIG. 8. Quantitative expression analysis of HQT HCT, C3H, CCoAOMT1, CCoAOMT2 and CCoAOMT3 in *C. canephora* (robusta, BP409) and *C. arabica* (arabica, T2308). The expression of each gene was determined by quantitative RT-PCR using TaqMan specific probes as described in the methods. The RQ value for each tissue sample was determined by normalizing the transcript level of the test gene versus the transcript level of the ubiquitously expressed rpl39 gene in each sample analyzed. The data shown represent mean values obtained from three amplification reactions for each sample and the error bars indicate the SD.

Analysis of HQT, HCT, C3H, CCoAOMT-4, CCoAOMT-L1, and CCoAOMT-L2 Gene Expression by Quantitative RT-PCR To precisely measure the expression of each of these genes, the levels of transcripts from the HQT, HCT, C3H, CCoAOMT-1, CCoAOMT-L1 and CCoAOMT-L2 genes were determined for several tissues of the arabica variety C. arabica T2308 and of the robusta variety C. canephora BP 409 using gene specific TaqMan primers/probes (Table 5). The different cDNA for these experiments were prepared by Method 1 with RNA isolated from roots, stems, leaves, flowers, and from the grain and pericarp tissues isolated from 4 different stages of developing arabica and robusta coffee cherries as described in Example 2, above. The results of these experiments are presented in FIG. 8.

Genes encoding HCT and HQT. TaqMan probe and primers were designed for the HQT and HCT genes (see Table 5) and these were then used to measure the transcript levels for each of these genes in several different arabica and robusta coffee tissues (see Example 2). The HQT expression profile (FIG. 8) seen for robusta shows that this gene is expressed at relatively high levels (RQ 0.71) in the grain at the small green stage, and at somewhat lower levels in all the other tissues examined. It is noted that the small green pericarp sample also has a slightly elevated level of HQT relative to the later stages of pericarp development. It has previously been demonstrated by the inventors that this robusta green grain sample has no endosperm specific gene expression (Provisional Application No. 60/696,445). This latter observation leads to the suggestion that the HQT gene may be highly expressed during the early stages of grain and pericarp development, and that the level of this transcript fall to relatively low levels in both tissues concomitant with the beginning of endosperm development.

The levels of HQT expression in the other robusta tissues suggest that this gene is generally expressed in various coffee tissues at constant low levels, suggesting it may have some type of "housekeeping" function. When the levels of HQT are examined in arabica, relatively similar levels were seen to robusta in the roots, stems, and young leaves and in most of the grain and pericarp tissues. This is consistent with the idea this is a potentially important housekeeping type gene. The low levels of HQT in the arabica small green grain and pericarp samples is consistent with the idea that HQT falls when the endosperm specific gene expression is induced because these arabica small green cherries express endosperm specific genes (Provisional Application No. 60/696,445). Finally, it is noted that large differences were also detected for HQT expression in the flowers of arabica and robusta. The differences are likely due to differences in the precise developmental stage of these two flower samples as the expression of several genes has been to seen to be extremely variable between these two flower samples The HCT expression profile seen for robusta indicates that this gene is expressed in relatively high levels in the pericarp at the large green (RQ 0.33), and yellow stages with lower levels seen in the pericarp at small green (RQ 0.09) and red stages. Transcript levels are relatively high in the roots and stems in robusta, while lower levels are seen in the leaves and flowers. Very low levels were also detected in the grain at all the stages studied. A somewhat different pattern of expression is seen in arabica, with no detection of HCT transcripts in the pericarp, except for a low level seen at the small green stage. In addition, no HCT transcripts were detected in the arabica stem tissues. In contrast, slightly higher levels of HCT were detected in the leaves and in the grain at the red stage in arabica relative to robusta. The detection of HCT expression in a limited number of arabica tissue samples eliminates the possibility that the HCT Taqman probe set, which was designed from the robusta sequence, is not recognized in this arabica variety. The HCT levels were similar in the arabica and robusta flower samples.

The higher expression of HCT in the arabica grain versus the robusta grain suggests that differences in the profiles of chlorogenic acids in arabica and robusta could, in part, be due to different levels of HCT expression in the mature coffee grain. Similarly, given the potential involvement of chlorogenic acids in pathogen resistance (Shadle et al. (2003); Niggeweg et al. (2004)), the high expression of HCT in robusta roots and stems could contribute significantly to the elevated pathogen resistance generally associated with robusta versus arabica coffees. It is noted that there is a relatively low expression of HCT in the robusta BP-409 leaf sample. However, considering this leaf sample is from young expanding leaves, it is possible that HCT expression in the mature leaf is significantly higher than in young leaves, perhaps due to the alternative use of CGA for the synthesis of lignin and other structural components during leaf expansion. This explanation for lower than expected HCT transcript levels in young leaves would further support that argument that higher HCT expression is linked to higher pathogen or disease resistance, as this would be an important characteristic for mature leaves.

Genes encoding C3H. Specific primers and TaqMan probes were designed for the C3H gene (see Table 5). This probe set was used to measure the C3H transcript levels in several different arabica and robusta coffee tissues as noted in Example 2. The data shown in FIG. 8 indicates that C3H transcripts can be detected in all the robusta tissues tested. A relatively high level of C3H transcripts is seen in the robusta small green stage grain sample, and relatively high levels of C3H transcripts are also seen in the pericarp (peaking at the large green and yellow stages). Lower levels of C3H transcripts are seen in the robusta stem, leaf and flower samples. Interestingly, no C3H transcripts were detected in the robusta root samples. In arabica, C3H transcript levels were similar in the grain to robusta, except in the small green stage. This latter observation is believed to be linked to the later developmental stage of the arabica sample as noted above. Interestingly, C3H transcript levels in the arabica pericarp samples are undetectable in the small green stage and then rise consistently until the red stage. This is in distinct contrast to the robusta samples, where C3H expression was higher early in development and then decreased at maturity.

Gene encoding CCoAOMT-1. A specific TaqMan probe and two primers were designed for the CCoAOMT1 gene (see Table 5). The quantitative RT-PCR data for this gene are presented in FIG. 8. In robusta grain, CCoAOMT-1 transcripts were very low in the small green stage (RQ 0.05) but higher in the large green (RQ 0.31) and yellow grain stages (RQ 0.76), then fall to a very low level in the mature grain (RQ 0.09). In the pericarp, the levels are low in the small green pericarp (RQ 0.15), slightly higher in the large green (RQ 0.56) and yellow stages (RQ 0.65), and then fall again to a very low level at the red stage (RQ 0.06). In robusta, the CCoAOMT-1 transcript levels were found to be relatively high in the roots (RQ 1.09) and stems (RQ 1.5), moderately high in the flowers (RQ 0.58) and very low in the leaf (RQ 0.06). In comparison to the BP409 robusta sample, in arabica T2308, the levels of CCoAOMT-1 are relatively high in the small green (RQ 0.56) and large green grain (RQ 1.21), and the red grain (RQ 1.43). The unexpected drop in CCoAOMT-1 levels in the yellow grain stage (RQ 0.16) was unexpected and will need to be verified in other arabica samples. The levels of CCoAOMT-1 transcript in the small green, large green, yellow arabica pericarp samples are relatively low.

Gene encoding CCoAOMT-L1. A specific TaqMan probe and two primers were designed for the CCoAMT-L1 gene (see Table 5). Overall, the quantitative RT-PCR results obtained indicate that the level of transcripts for the CCoAOMT-L1 gene is either near, or below, the level of detection in all of the robusta tissues examined. A relatively similar result was obtained for all of the arabica samples, except the flower sample. In this case, CCoAOMT-L1 transcripts were very clearly detected (RQ 0.14), that is, this gene has a 7.8 fold higher level of transcripts than that detected in the arabica small green grain (RQ 0.018). The presence of these transcripts in the arabica flower sample suggests that this gene is specifically expressed in one or more parts of the flower. Furthermore, the absence of CCoAOMT-L1 transcripts in the robusta flowers suggests the arabica and robusta flowers are at different stages of maturity, and thus the expression of CCoAOMT-L1 could be stage specific during flower development. Supporting this latter argument, several other coffee genes have shown widely different expression in the same arabica and robusta flower samples, again indicating these samples are at different stages of maturity.

Gene encoding CCoAOMT-L2. A specific TaqMan probe and two primers were designed for the CCoAOMT-L2 gene (see Table 5). The quantitative RT-PCR results obtained for this gene indicated that, apart from the robusta flower sample, CCoAOMT-L2 expression was not reliably detected in any of the robusta or arabica tissue samples using the experimental conditions described here. It is noted that control experiments have shown that the amplification efficiency of the rpl39 primer/probe set and the efficiency of the CCoAOMT-L2 primer/probe set were similar when tested against their respective plasmids. Thus, it is not likely that the absence of detectable expression for the CCoAOMT-L2 gene in robusta or arabica found here was due to a specific problem with the CCoAOMT-L2 primer/probe set.

EXAMPLE 13

Functional Activity of Recombinant Coffee HCT

Activity was not detected from recombinant GST-tagged HCT and GST-tagged HQT proteins produced in *E. coli*. To determine if the GST tag was hindering the activity of these proteins, the GST tags were removed enzymatically from each protein. The recombinant HCT and HQT protein (without tags) were then reassayed for activity.

AcTEV protease digestion: The recombinant HCT-GST or HQT-GST recombinant proteins, produced and purified as described in Example 11, were digested by AcTEV according to the instructions of the supplier (Invitrogen): 140 µl of recombinant enzyme was digested at 30° C. for 2 h with 7.5 µl of TEV buffer (20× buffer, Invitrogen), 1.5 µl of 0.1 mM DTT, and 2 µl of AcTEV protease (20 units).

Enzyme assay: Modified methods Niggeweg et al, 2004 and Hoffmann et al, 2003 were used. Enzyme activity was determined at 40° C. using the reverse reaction (cleavage of 5-CQA to caffeoyl-CoA and quinic acid). The reaction mixture (200u1 total) was; 100 mM Na-Pi buffer pH 6.5, 1 mM DTT, 5 mM CGA (5-CQA—Sigma), 3.3 mM CoA, and 30 µL AcTEV digested GST-HCT or GST-HQT recombinant enzyme. The reaction was started by addition of the substrate CoA. At each time point; 30 µl of the reaction mixture was stopped by addition of 170 µl of stop buffer (0.1% formic acid, 5% acetonitrile). This material was then filtered using a 0.2 µm filter, and then loaded on the HPLC column.

HPLC method: Reaction products were analyzed by HPLC, using a Waters reverse-phase C18 column (4 µm, 4.6×250 mm) and a (8-50%) gradient of acetonitrile: solvent A was 91% milliQ $H_2O$, 8% $CH_3CN$, and 1% formic acid; solvent B was 49% milliQ $H_2O$, 50% $CH_3CN$, and 1% formic acid, solvents were sparged with 30% helium). The gradient was as follows; at 0 min, 98% A-2% B; at 5 min, 92% A-8% B; at 25 min, 50% A-50% B; at 30 min, 30% A-70% B; at 35 min, 30% A-70% B; then from 37-45 minutes, 98% A-2% B.

The compounds eluted were detected at 325 nm. The compounds were characterized by their elution times and their UV absorption spectra, and their identities were confirmed by standards when available.

Results:

The treatment of GST-tagged HCT and GST-tagged HQT proteins with AcTEV protein was shown by SDS PAGE gel electorphoresis and coomassie staining to generate a smaller polypeptide with the expected molecular weight of the full length proteins from each of the GST-tagged "precursor" proteins. This observation demonstrates that the AvTEV protease successfully released the GST-Tag from the GST-HCT and GST-HQT proteins and thus produced the normal full length HCT and HQT polypeptides.

Figure 20:
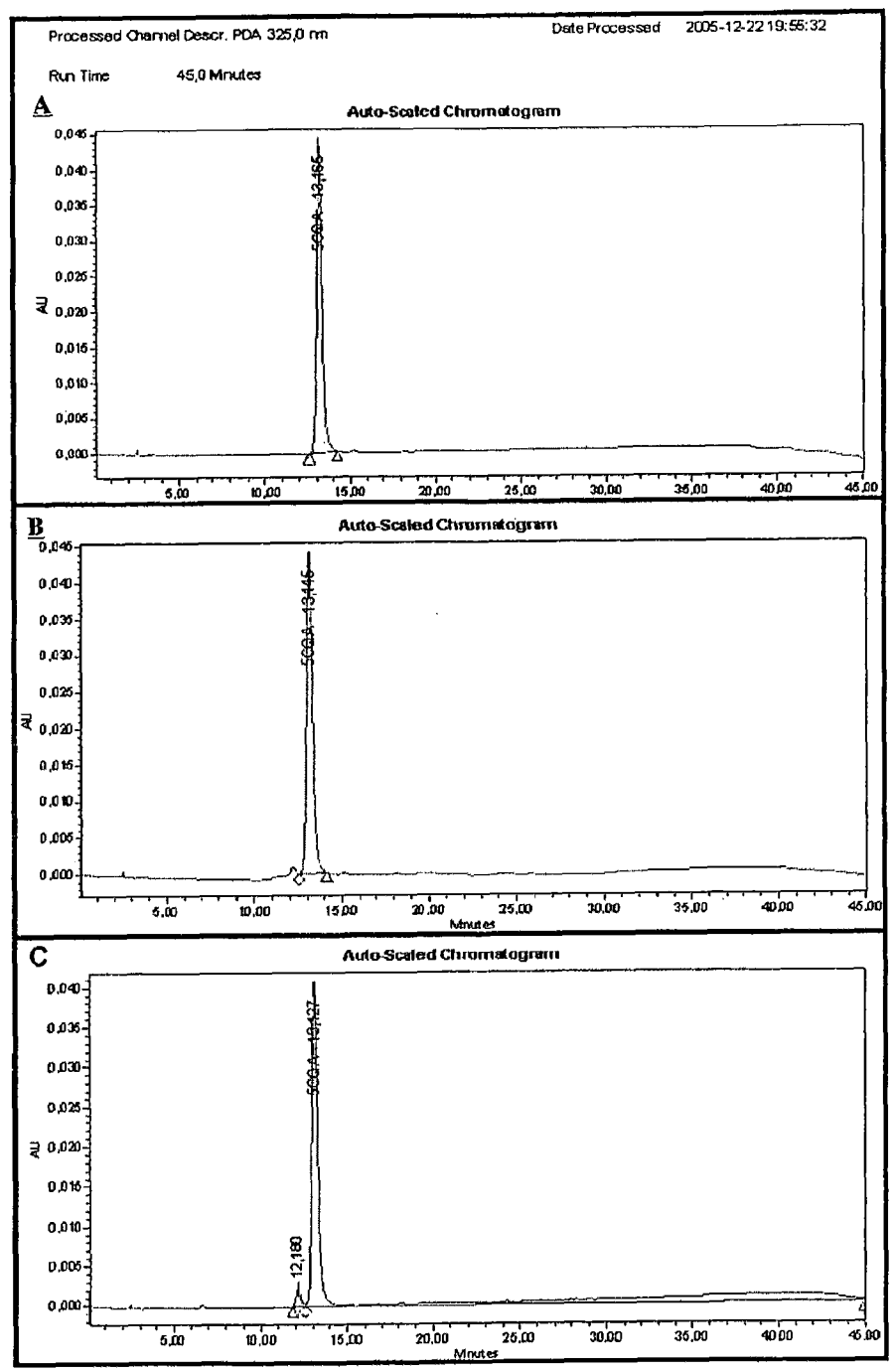
FIG. 20. HPLC elution profile of 5CQA sample at 40° C. in activity buffer (negative control). A: T=0 HPLC spectrum, B: T2 hour HPLC spectrum. C: T4 hour HPLC spectrum.

FIG. 20 shows the control reaction for HCT/HQT activity (5-CQA cleaved to caffeoyl-CoA and quinic acid). That reaction contained all the reactants, but with no enzyme added. The results shown in FIG. 20 demonstrate that under the conditions employed, chlorogenic acid (5-CQA) is stable; the CGA peak is only slightly lower at T=4 hours versus the peak size at T=0, and only one very small peak appears at 12.1 minutes.

Figure 21:
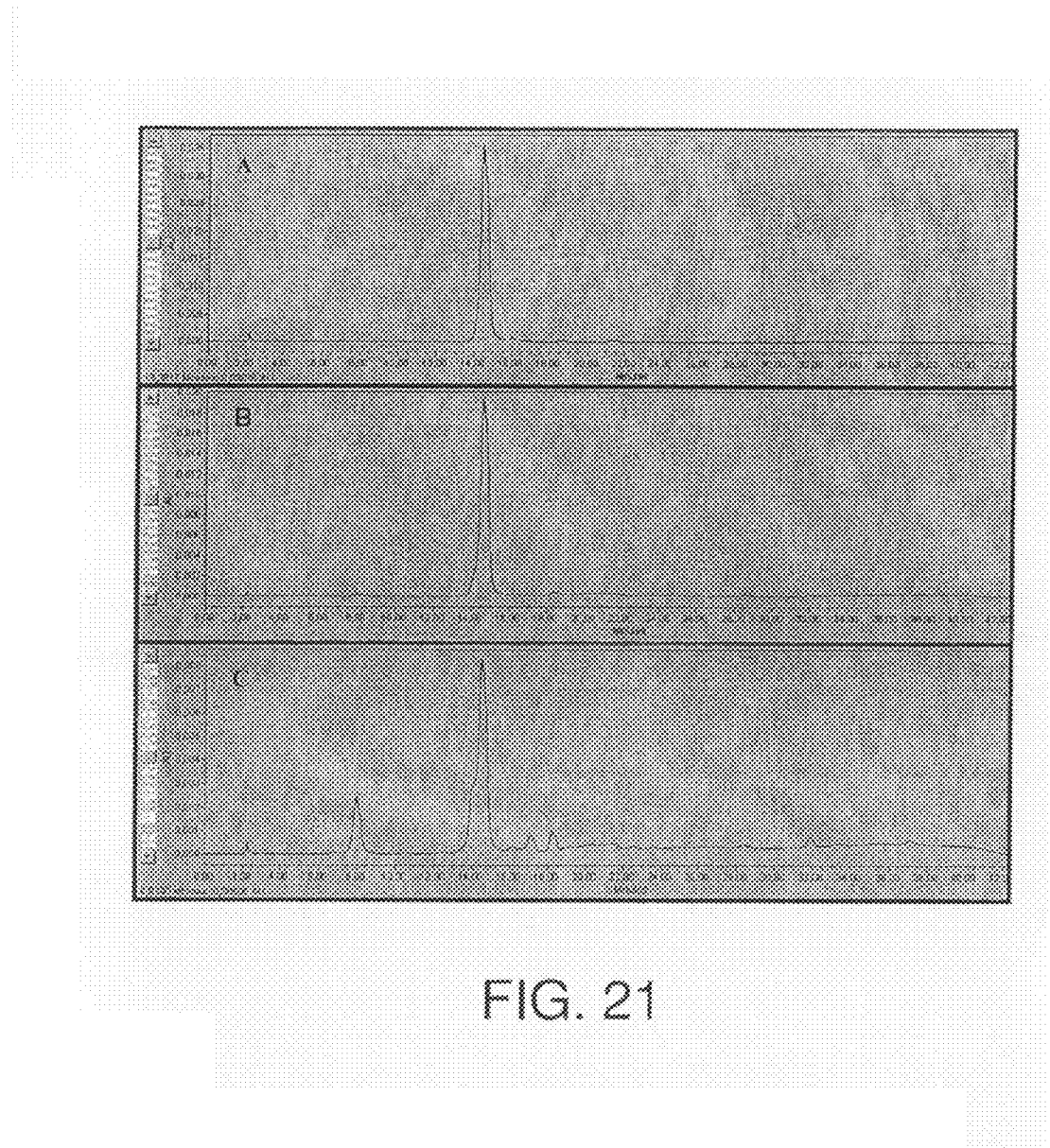
FIG. 21. HPLC elution profile of samples taken from reaction with recombinant HCT (released after cleavage with AcTEV protease) and 5CQA substrate. A: HPLC profile of sample at T=0, B: HPLC profile of sample after 4 h incubation at 40° C. C: HPLC profile of sample after 24 h incubation at 40° C. The peak at retention time of approximately 14.4 min has been identified as 5CQA by comparison of standard injection. Similarly, the peak at 2 min has been identified as Coenzyme A.

In contrast, FIG. 21 shows that the CGA peak in the reaction with AvTEV treated GST-HCT protein was reduced significantly (from approximately 0.035 at T=0 to approximately 0.02 at T=4 hours). The reduction of the CGA peak is accompanied by the appearance of several new peaks. The new peaks are at approximately 8 minutes, 17.1 minutes and 18.3 minutes respectively, in addition to the development of a significant shoulder on the CGA peak. Because under these elution conditions, caffeic acid elutes very close to the 5-CQA peak, the addition of the recombinant coffee HCT polypeptide causes the accumulation of caffeic acid. While the product expected from this reaction was caffeoyl-CoA, it is likely that this molecule was unstable in the buffer used and rapidly degraded, forming the caffeic acid observed. In agreement with this argument, it is likely that one of the peaks at 17.1 minutes and 18.3 minutes is actually caffeoyl-CoA.

References

Altschul S. F., Madden T. L., Schaffer A. A., Zhang J., Zhang Z., Miller W., Lipman D. J. (1997) Gapped BLAST and PSI-BLAST: a new generation of protein database search programs. *Nucleic Acids Res.* 25: 3389-3402.

Ben Amor M. and McCarthy J. (2003) Modulation of coffee flavour precursor levels in green coffee grains. European Patent EPC/03394056.0.

Clifford M. N. (1985) Chlorogenic acids, in *Coffee* 1. *Chemistry*, Ed by Clarke R J and Macrae R. Elsevier Applied Science, London, pp 153-202.

Clifford M. N., Walker R (1987) Chlorogenic acids—confounders of coffee±serum cholesterol relationships. *Food Chem* 24: 77-80.

Clifford M. N. (1998) The nature of chlorogenic acids—are they advantageous compounds in coffee?, in *Dix-septième Colloque Scientifque International sur le Café*. ASIC, Paris, pp 79-91.

Clifford M. N. (1999) Chlorogenic acids and other cinnamates—nature, occurrence and dietary burden. *J Sci Food Agric* 79: 362-372.

Clifford M. N. (2000) Chlorogenic acids and other cinnamates—nature, occurrence, dietary burden, absorption and metabolism *J Sci Food Agric* 80: 1033-1043.

Crouzillat D., Lerceteau E., Petiard V., Morera J., Rodriguez H., Walker D., Philips W. R. R., Schnell J., Osei J. and Fritz P. (1996). *Theobroma cacao* L.: a genetic linkage map and quantitative trait loci analysis. *Theor Appl Genet.* 93: 205-214.

Ferrer J L, Zubieta C, Dixon R A, Noel J P (2005) Crystal structures of alfalfa caffeoyl coenzyme A 3-O-methyltransferase. *Plant Physiol* 137: 1009-1017.

Gang D., Wang J., Dudareva N., Hee Nam K, Simon J., Lewinsohn E., Pichersky E (2001) An Investigation of the Storage and Biosynthesis of Phenylpropenes in Sweet Basil *Plant physiol.* 125: 539-555.

Grace S. C., Logan B. A. (2000) Energy dissipation and radical scavenging by the plant phenylpropanoid pathway *Phil. Trans. R. Soc. Lond. B*. 355:1499-1510.

Hoffmann L., Maury S., Martz F., Geoffroy P., Legrand M. (2003) Purification, Cloning, and Properties of an Acyltransferase Controlling Shikimate and Quinate Ester Intermediates in Phenylpropanoid Metabolism *J. Bio. Chem.* 278(1): 95-103.

Hoffmann L., Besseau S., Geoffroy P, Ritzenthaler C., Meyer D. Lapierre C, Pollet B. Legrand M (2004) Silencing of Hydroxycinnamoyl-Coenzyme A Shikimate/Quinate Hydroxycinnamoyltransferase Affects Phenylpropanoid Biosynthesis *Plant Cell* 16: 1446-1465.

Hollman P. C. H. (2001) Evidence for health benefits of plant phenols: local or systemic effects? *J. Sci. Food Agric.* 81:842-852.

Inoue K, Sewalt V J, Murray G B, Ni W, Sturzer C, Dixon R A (1998) Developmental expression and substrate specificities of alfalfa caffeic acid 3-O-methyltransferase and caffeoyl coenzyme A 3-O-methyltransferase in relation to lignification. *Plant Physiol* 117: 761-770.

Ky C.-L., Louarn J., Dussert S., Guyot B., Hamon S., Noirot M. (2001) Caffeine, trigonelline, chlorogenic acids and sucrose diversityin wild *Coffea arabica* L. and *C. canephora* P. accessions *Food Chemistry* 75: 223-230.

Lee C. Y., Jaworski A. (1987) Phenolic compounds in white grapes grown in New York. Am. Enol. & Viticul. 38: 277-281.

Leloup V., Louvrier A., Liardon R. (1995) Degradation mecanisms of chlorogenic acids during roasting. *Compte-rendus du Seizième Colloque de l'ASIC (Association Scientifique Internationale sur le Café)* ASIC Kyoto pp 192-198.

Maher E. A., Bate N. J., Ni W., Elkind Y., Dixon R. A., Lamb C. J. (1994) Increased disease susceptibility of transgenic tobacco plants with suppressed levels of preformed phenylpropanoid products. *Proc. Natl. Acad. Sci. USA* 91:7802-7806.

Marraccini P., Deshayes A., Petiard V. and Rogers W. J. 1999. Molecular cloning of the complete 11S seed storage protein gene of *Coffea arabica* and promoter analysis in the transgenic tobacco plants. *Plant Physiol. Biochem.* 37:273-282.

Maury, S., Geoffroy, P., Legrand, M. (1999) Tobacco O-methyltransferases involved in phenylpropanoid metabolism.

The different caffeoyl-coenzyme A/5-hydroxyferuloyl-coenzyme A 3/5-O-methyltransferase and caffeic acid/5-hydroxyferulic acid 3/5-O-methyltransferase classes have distinct substrate specificities and expression patterns. *Plant Physiol.* 121: 215-224.

Mitchell H. J., Hall S. A., Stratford R., Hall J. L., Barber M. S. (1999). Differential induction of cinnamyl alcohol dehydrogenase during defensive lignification in wheat (*Triticum aestivum* L.): characterisation of the major inducible form. *Planta* 208: 31-37.

Montavon P., Duruz E., Rumo G., Pratz G. (2003a) Evolution of Green Coffee Protein Profiles with Maturation and Relationship to Coffee Cup Quality *J. Agric. Food Chem.* 51: 2328-2334

Montavon P., Mauron A. F. Duruz E. (2003b) Changes in Green Coffee Protein Profiles during Roasting *Food Chem.* 51: 2335-2343.

Nair R., Xia Q., Kartha C., Kurylo E., Hirji R., Datla R., Selvaraj G. (2002) *Arabidopsis* CYP98A3 Mediating Aromatic 3-Hydroxylation. Developmental Regulation of the Gene, and Expression in Yeast *Plant physiol.* 130: 210-220.

Natella F., Nardini M., Giannetti I., Datillo C., Scaccini C. (2002) Coffee Drinking Influences Plasma Antioxidant Capacity in Humans *J. Agric. Food Chem.* 50: 6211-6216.

Niggeweg R., Michael A., Martin C. (2004) Engineering plants with increased levels of the antioxydant chlorogenic acid *Nature Biotech.* 22(6): 746-54.

Ohnishi M., Morishita H., Iwahasi H., Toda S., Shirataki Y., Kimura M., Kido R. (1994) Inhibitory effects of chlorogenic acids on linoleic acid peroxidation and haemolysis. *Phytochemistry* 36:579-584.

Olthof M. R., Hollman P. C. H., Katan M. B. (2001) Chlorogenic acid and caffeic acid are absorbed in humans. *J. Nutr.* 131:66-71.

Parvathi K, Chen F, Guo D J, Blount J W, Dixon R A (2001) Substrate preferences of O-methyltransferases in alfalfa suggest new pathways for 3-O-methylation of monolignols. *Plant Journal* 25: 193-202.

Rice-Evans C. A., Miller M. J., Paganga G. (1996) Structure-antioxidant activity relationships of flavonoids and phenolic acids. *Free Rad. Biol. Med.* 20:933-956.

Rogers J., Michaux S., Bastin M., Bucheli P. (1999) Changes to the content of sugars, sugar alcohols, myo-inositol, carboxylic acids and inorganic anions in developing grains from different varieties of Robusta (*Coffea canephora*) and Arabica (*C. arabica*) coffees *Plant Science.* 149: 115-123.

Schoch G., Goepfert S., Morant M., Hehn A., Meyer D., Ullmann P., Werck-Reichhart D. (2001) CYP98A3 from *Arabidopsis thaliana* Is a 3-Hydroxylase of Phenolic Esters, a Missing Link in the Phenylpropanoid Pathway. *J. Bio. Chem.* 266(39): 36566-36574.

Shadle G., Wesley V., Korth K., Chen F., Lamb C., Dixon R. (2003) Phenylpropanoid compounds and disease resistance in transgenic tobacco with altered expression of 1-phenylalanine ammonia-lyase *Phytochemistry* 64: 153-161.

Shibata H., Sakamoto Y., Oka M., Kono Y. (1999) Natural antioxidant, chlorogenic acid, protects against DNA breakage caused by monochloramine. *Biosci. Biotechnol. Biochem.* 63:1295-1297.

Tamagnone T, Merida A., Stacey N., Plaskitt K., Parr A., Chang C. F., Lynn D., Dow M., Roberts K., Martin C. (1998) Inhibition of Phenolic Acid Metabolism Results in Precocious Cell Death and Altered Cell Morphology in Leaves of Transgenic Tobacco Plants *Plant Cell* 10: 1801-1816.

Voilley, A., Sauvageot, F., Durand, D. (1977). Influence sur l'amertume d'un café boisson de quelques paramètres d'extraction. *Compte-Rendus du Huitième Colloque de l'ASIC (Association Scientifique International sur le Café)*, ASIC pp 192-198251-259.

Zhong R, III W, Negrel J, Ye Z H (1998) Dual methylation pathways in lignin biosynthesis. *Plant Cell* 1998 December; 10(12):2033-46.

---

What is claimed is:

1. A nucleic acid molecule isolated from coffee (*Coffea* spp.), comprising a coding sequence that encodes a hydroxycinnamoyl-CoA shikimate/quinate hydroxycinnamoyltransferase having at least 95% sequence identity to the amino acid sequence of SEQ ID NO: 9 or 10.

2. The nucleic acid molecule of claim 1, wherein the coding sequence is an open reading frame of a gene, or a mRNA molecule, or a cDNA molecule.

3. The coding sequence of the nucleic acid molecule of claim 1, contained in a vector.

4. The vector of claim 3, which is an expression vector selected from the group of vectors consisting of plasmid, phagemid, cosmid, baculovirus, bacmid, bacterial, yeast and viral vectors.

5. The vector of claim 3, wherein the coding sequence of the nucleic acid molecule is operably linked to a constitutive promoter, or an inducible promoter, or a tissue-specific promoter.

6. The vector of claim 5, wherein the tissue specific promoter is a seed specific promoter.

7. The vector of claim 6, wherein the seed specific promoter is a coffee seed specific promoter.

8. A host cell transformed with the vector of claim 3.

9. The host cell of claim 8, which is a plant cell selected from the group of plants consisting of coffee, tobacco, *Arabidopsis*, maize, wheat, rice, soybean barley, rye, oats, sorghum, alfalfa, clover, canola, safflower, sunflower, peanut, cacao, tomatillo, potato, pepper, eggplant, sugar beet, carrot, cucumber, lettuce, pea, aster, begonia, chrysanthemum, delphinium, zinnia, and turfgrasses.

10. A method of modulating flavor or aroma of coffee beans, the method comprising performing a transformation and thereby modulating production or activity of hydroxycinnamoyl-CoA shikimate/quinate hydroxycinnamoyltransferase comprising an amino acid sequence at least 95% identical to SEQ ID NO: 9 or 10.

11. The method of claim 10, comprising increasing production or activity of the hydroxycinnamoyl-CoA shikimate/quinate hydroxycinnamoyltransferase.

12. The method of claim 10, comprising decreasing production or activity of the hydroxycinnamoyl-CoA shikimate/quinate hydroxycinnamoyltransferase.

* * * * *